US012637722B2

(12) United States Patent
Mueller et al.

(10) Patent No.: US 12,637,722 B2
(45) Date of Patent: May 26, 2026

(54) METHOD FOR CONFIRMING THE IDENTITY OF A PRODUCT BY MEANS OF A MICROBIAL DNA TAG

(71) Applicant: Natural Trace PTE. LTD., Singapore (SG)

(72) Inventors: Lukas A. Mueller, Ithaca, NY (US); Chantal Roth, Kallnach (CH)

(73) Assignee: Natural Trace Pte. Ltd., Singapore (SG)

( * ) Notice: Subject to any disclaimer, the term of this patent is extended or adjusted under 35 U.S.C. 154(b) by 0 days.

(21) Appl. No.: 18/724,919

(22) PCT Filed: Jan. 10, 2023

(86) PCT No.: PCT/US2023/060343
§ 371 (c)(1),
(2) Date: Jun. 27, 2024

(87) PCT Pub. No.: WO2023/147213
PCT Pub. Date: Aug. 3, 2023

(65) Prior Publication Data
US 2024/0417814 A1    Dec. 19, 2024

Related U.S. Application Data

(60) Provisional application No. 63/297,963, filed on Jan. 10, 2022.

(51) Int. Cl.
| | |
|---|---|
| *C12Q 1/68* | (2018.01) |
| *C12Q 1/6811* | (2018.01) |
| *C12Q 1/689* | (2018.01) |
| *G16B 30/10* | (2019.01) |
| *G16B 50/30* | (2019.01) |

(52) U.S. Cl.
CPC ........... *C12Q 1/689* (2013.01); *C12Q 1/6811* (2013.01); *G16B 30/10* (2019.02); *G16B 50/30* (2019.02)

(58) Field of Classification Search
None
See application file for complete search history.

(56) References Cited

U.S. PATENT DOCUMENTS

| | | | |
|---|---|---|---|
| 6,312,911 | B1 | 11/2001 | Bancroft et al. |
| 6,647,649 | B2 | 11/2003 | Hunt et al. |
| 7,781,224 | B2 | 8/2010 | Martin et al. |
| 8,293,535 | B2 | 10/2012 | Farquar et al. |
| 8,835,178 | B2 | 9/2014 | Farquar et al. |
| 9,023,650 | B2 | 5/2015 | Farquar et al. |
| 9,243,283 | B2 | 1/2016 | Schwartz et al. |
| 9,262,738 | B2 | 2/2016 | Glazer |
| 9,290,810 | B2 | 3/2016 | Farquar et al. |
| 9,617,598 | B2 | 4/2017 | Xie et al. |
| 9,810,659 | B2 | 11/2017 | Alocilja |

| | | | | |
|---|---|---|---|---|
| 9,850,531 | B2 | 12/2017 | Grass et al. | |
| 9,912,512 | B2 * | 3/2018 | Zhao | H04L 27/2331 |
| 9,919,512 | B2 | 3/2018 | Jung et al. | |
| 10,302,614 | B2 * | 5/2019 | Zografos | G01N 33/02 |
| 10,451,579 | B2 | 10/2019 | Alocilja | |
| 10,501,786 | B2 | 12/2019 | Anderson et al. | |
| 10,513,735 | B2 | 12/2019 | Swartz et al. | |
| 10,870,879 | B2 | 12/2020 | Drukker et al. | |
| 10,926,264 | B2 * | 2/2021 | Zografos | B01L 3/527 |
| 10,962,512 | B2 * | 3/2021 | Zografos | G01N 33/025 |
| 11,200,383 | B2 * | 12/2021 | Zografos | G06K 7/10366 |
| 11,692,988 | B2 * | 7/2023 | Zografos | G01N 33/02 426/531 |
| 11,699,045 | B2 * | 7/2023 | Zografos | G06K 7/12 235/440 |

(Continued)

FOREIGN PATENT DOCUMENTS

| | | | | |
|---|---|---|---|---|
| WO | WO-2014193909 A1 * | 12/2014 | ............... | C12Q 1/68 |
| WO | WO-2015026254 A1 * | 2/2015 | ............... | C12Q 1/68 |

(Continued)

OTHER PUBLICATIONS

Sun et al. (2011). Tag-Encoded FLX Amplicon Pyrosequencing for the Elucidation of Microbial and Functional Gene Diversity in Any Environment. Methods in Molecular Biology, Humana Press, vol. 733. Chapter 9, High-Throughput Next Generation Sequencing, pp. 129-141. (Year: 2011).*

Casey, M.G., Isolini, D., Amrein, R., Wechsler, D. and Berthoud, H., 2008. Naturally occurring genetic markers in lactobacilli and their use to verify the authenticity of Swiss Emmental PDO cheese. Dairy science & technology, 88(4), pp. 457-466. (Year: 2008).*

Ludin et al., 2016. Lactic acid bacteria as markers for the authentication of Swiss Cheeses. Chimia, 70(5), pp. 349-349. (Year: 2016).*

English Translation document of WO2015-026254A1, pub. Feb. 26, 2015 (Year: 2015).*

Ray et al., 2012. Nanomaterials for targeted detection and photothermal killing of bacteria. Chemical Society Reviews, 41(8), pp. 3193-3209. (Year: 2012).*

(Continued)

*Primary Examiner* — Gary Benzion
*Assistant Examiner* — Olayinka A Oyeyemi
(74) *Attorney, Agent, or Firm* — Renner, Kenner, Greive, Bobak, Taylor & Weber Co., LPA

(57) ABSTRACT

The present invention is directed to methods for confirming the identity of an item or product using a segment of DNA present in a killed microorganism as a tag. In some embodiments, a food compatible microorganism containing a target nucleotide sequences not present in the item to be tagged is selected to serve as a tag and an identity unique identifier and/or other metadata for of the item is then saved for that tag in a database. The microorganism is killed to create a tag with the target nucleotide sequence and the tag is added to the item. The identity of the item can later be confirmed by extracting the DNA in the item and amplifying the target nucleotide sequence or sequences using PCR techniques, sequencing each amplified target nucleotide sequence; and then comparing them to the nucleotide sequence saved for the target nucleotide sequence.

27 Claims, 26 Drawing Sheets

Specification includes a Sequence Listing.

(56)     References Cited

U.S. PATENT DOCUMENTS

| | | | | |
|---|---|---|---|---|
| 11,801,512 | B2 * | 10/2023 | Zografos | B01L 3/527 |
| 11,853,832 | B2 * | 12/2023 | Zografos | G06K 7/12 |
| 12,487,214 | B2 * | 12/2025 | Zografos | A61L 2/28 |
| 2004/0166520 | A1 | 8/2004 | Connolly | |
| 2004/0219533 | A1 | 11/2004 | Davis et al. | |
| 2005/0026181 | A1 | 2/2005 | Davis et al. | |
| 2009/0197251 | A1 | 8/2009 | Melchior et al. | |
| 2011/0207125 | A1 | 8/2011 | Jacob et al. | |
| 2014/0220576 | A1 | 8/2014 | Macula | |
| 2014/0272097 | A1 | 9/2014 | Jung et al. | |
| 2014/0356858 | A1 * | 12/2014 | Harman | C12Q 1/68 |
| | | | | 435/6.12 |
| 2015/0322426 | A1 * | 11/2015 | Zografos | C12N 15/1065 |
| | | | | 426/531 |
| 2017/0038353 | A1 * | 2/2017 | Zografos | G01N 31/226 |
| 2018/0357365 | A1 | 12/2018 | Meadow et al. | |
| 2019/0211324 | A1 * | 7/2019 | Zografos | B05B 12/1418 |
| 2019/0241982 | A1 * | 8/2019 | Hogan | C12Q 1/6895 |
| 2019/0285602 | A1 * | 9/2019 | Zografos | C12Q 1/686 |
| 2019/0300948 | A1 | 10/2019 | Cuppens | |
| 2020/0074124 | A1 * | 3/2020 | Zografos | G06K 7/0004 |
| 2021/0019973 | A1 | 1/2021 | Yin et al. | |
| 2021/0108192 | A1 | 4/2021 | Mattei | |
| 2021/0181169 | A1 * | 6/2021 | Zografos | A61L 2/28 |
| 2021/0205815 | A1 * | 7/2021 | Zografos | B01L 3/527 |
| 2022/0245367 | A1 * | 8/2022 | Zografos | G16B 50/10 |
| 2023/0121172 | A1 * | 4/2023 | Zografos | G06K 7/12 |
| | | | | 235/440 |
| 2023/0366866 | A1 * | 11/2023 | Zografos | G01N 33/02 |
| 2024/0417814 | A1 * | 12/2024 | Mueller | G16B 50/30 |

FOREIGN PATENT DOCUMENTS

| | | | | | |
|---|---|---|---|---|---|
| WO | WO-2016114808 | A1 * | 7/2016 | | C12Q 1/686 |
| WO | WO-2017023431 | A1 * | 2/2017 | | C07H 21/04 |
| WO | 2018142131 | A1 | 8/2018 | | |
| WO | WO-2019140101 | A1 * | 7/2019 | | B05B 7/2494 |
| WO | 2019157227 | A1 | 8/2019 | | |
| WO | WO-2020028955 | A1 * | 2/2020 | | G06Q 30/0185 |
| WO | 2021102579 | A1 | 6/2021 | | |
| WO | WO-2021173156 | A1 * | 9/2021 | | C12Q 1/68 |
| WO | WO-2023147213 | A2 * | 8/2023 | | C12Q 1/6811 |

OTHER PUBLICATIONS

Poltronieri et al., 2008. DNA arrays and membrane hybridization methods for screening of six Lactobacillus species common in food products. Food Analytical Methods, 1(3), pp. 171-180. (Year: 2008).*

Galimberti et al., 2014. DNA barcoding for minor crops and food traceability. Advances in Agriculture, 2014(1), 831875, pp. 1-pp. 8. (Year: 2014).*

Behjati S, et al. "What is next generation sequencing?" Arch Dis Child Educ Pract Ed 2013;98:236-238. doi:10.1136.

Ludin, P et al. "Lactic Acid Bacteria as Markers for the Authentication of Swiss Cheeses" Chimia, 2016, 70950; 349-353.

Meagan Phelan. "Barcoded Microbes Could Track Sources of Food Contamination" 1-5. American Association for the Advancement of Science (AAAS). Web. Jun. 5, 2020.

* cited by examiner

Control
Untreated        90°C; 10 min        80°C; 20 min        121°C; 15 min

METHOD FOR CONFIRMING THE IDENTITY OF A PRODUCT BY MEANS OF A MICROBIAL DNA TAG

CROSS REFERENCE TO RELATED APPLICATIONS

This application claims the benefit of U.S. provisional patent application Ser. No. 62/297,963 entitled "Method for Confirming the Identity of a Product by Means of a Microbial DNA Tag," filed Jan. 10, 2021, and incorporated herein by reference in its entirety.

SEQUENCE LISTING

The Sequence Listing file entitled "NTRPWO0001SL" having a size of 41,445 bytes and creation date of Jan. 9, 2023, that was electronically filed with the patent application is incorporated herein by reference in its entirety.

FIELD OF THE INVENTION

One or more embodiments of the present invention relates to a method for to the tracking of products, such as food, agricultural, personal care, cosmetics, and pharmaceutical products. In certain embodiments, the invention relates to various methods of tracking of products, such as food, agricultural, personal care, cosmetics, and pharmaceutical products in a supply chain using microorganisms killed by heat, irradiation, or other food-grade killing methods as markers and related methods for detection of such markers.

BACKGROUND OF THE INVENTION

As supply chains have become larger and global in scope, precise tracking of the provenance of shipments is necessary to assure the authenticity and integrity of items or products. The ability to assure the authenticity and integrity is particularly important for products that are ingested, inhaled, or applied onto the skin of humans and animals. This is generally true for food and feed and even more so in countries where transgenic foods are prohibited, or where special food regimens are predominant, such as halal and kosher foods.

While containers can be marked with barcodes or RFID tags and other means to track and trace, the authenticity and integrity of the product contained within cannot be assured, as they could have been swapped out or adulterated during transport or storage. Accordingly, numerous attempts have been made to try to tag the product itself.

Different schemes have been proposed that involve tagging using DNA to code the origin of a product; but these have been found to have severe limitations. The problem with most currently available proposals is that the DNA is not natural in origin and requires encapsulation that can be detrimental in key applications, the range of unique identifiers is limited, they do not allow detection of multiple tags in one product and/or the signal to noise ratio is too high.

What is needed in the art is a safe, food-compatible (e.g., GRAS), natural, and stable tagging system scalable to permit the tagging with a large number of unique identifiers, allowing lot-level identification of products, and detection of multiple tags in a single product.

SUMMARY OF THE INVENTION

In one or more embodiments, the present invention provides a safe, food-compatible, natural, and stable tagging system scalable to allow tagging using a large number of unique identifiers, allowing lot-level identification of products and detection of multiple tags in a single product. Microorganisms provide an almost unlimited amount of variation in their genomic DNA sequences. This diversity, if suitably characterized, can be used to define unique identifiers, based on sequences unique to a microorganism that are not naturally present in the product, which enable a product or shipment lot to be tracked and traced. The strain identifier and the sequence of the tag, among other things, are stored in a database for later comparison. If necessary, more sequence diversity can be generated by using a natural and food-compatible (e.g., GRAS) induction natural sequence variation process.

Since microorganisms have an active metabolism that might have a detrimental effect on the item or product, however, it is essential to kill the microorganisms before their addition to the item or product. As will be apparent, the microorganisms are killed without destroying the DNA of the microorganism that will serve as a tag. Many microorganisms have strong cell walls that protect the microorganism's cell, including the DNA contained in the cells. In some embodiments, the procedures described herein for killing the microorganisms, have been found to reliably kill between 70 and 100% of the cells, while leaving some or all of the cell walls in place to protect the DNA in the cell. (See U.S. Patent Application publication No. 2005/0180962 A1, the disclosure of which is incorporated herein by reference in its entirety).

The genome nucleotide sequences of these killed microorganisms, which have been characterized and are known, are compared to one or more databases of other known genomic nucleotide sequences to identify unique nucleotide sequences or in any event, sequences that are different from those present in the item or product being tagged. These sequences, generally referred to herein as "target sequences," serve as unique tags and are recorded and saved in a database, spreadsheet, ledger, block chain or other similar system, and are linked therein to identifying and/or other information that is to be represented by the tag. As will be apparent, each of these tags can be used to identify any aspect of an item or its provenance in this way. In various embodiments, a target sequence "tag" may be associated with different types of metadata, including, without limitation, such things as an assigned unique identifier number (UID), the name and location of the producer of manufacturer, shipment information (origin, itinerary, destination information), shipment metadata (temperature, packaging, etc.), lot numbers, production date, expiry date, source, the name and location of distributor or distributors, production methods, the name and location of the licensee or licensees, critical quality parameters, critical process parameters, manufacture or growth conditions, geographical origin/provenance, climate information, environmental information, the use of pesticides and other agricultural practices, other grower metadata, the allergen-free status, the halal/kosher/organic status, the GMO-free status, the fair trade status, the regulatory approval status (e.g., USDA or FDA approval status), other customer information, and combinations thereof. The killed microorganism containing the "tag" is then added to the item or product and can be later retrieved and detected using PCR and/or DNA sequencing, to ascertain the identity of the item or particular product tagged.

Moreover, the process allows for detection of multiple markers simultaneously in a product, allowing tracking of the provenance of many ingredients of a compounded product simultaneously. This allows the user to detecting crossbatch contamination and is particularly useful for tracking and tracing consumer products where the original product undergoes multiple compounding steps and trace the individual ingredients in the compounded product independently.

BRIEF DESCRIPTION OF THE DRAWINGS

For a more complete understanding of the features and advantages of the present invention, reference is now made to the detailed description of the invention along with the accompanying figures in which:

FIG. 2A is a micrograph showing live *Bifidobacterium longum* bacteria as seen in an electron microscopic preparation; FIG. 2B is a micrograph showing bacteria killed by heating at 80° C. for 20 minutes, which resulted in zero colonies in a dilution series in petri dish assay (See FIG. 4) (note that the cell structures are still intact); and FIG. 2C is a micrograph showing heat killed samples 4 weeks after the same heat treatment. Even after this aging step, the cell structures still appear intact.

Figures 7A, 7B:
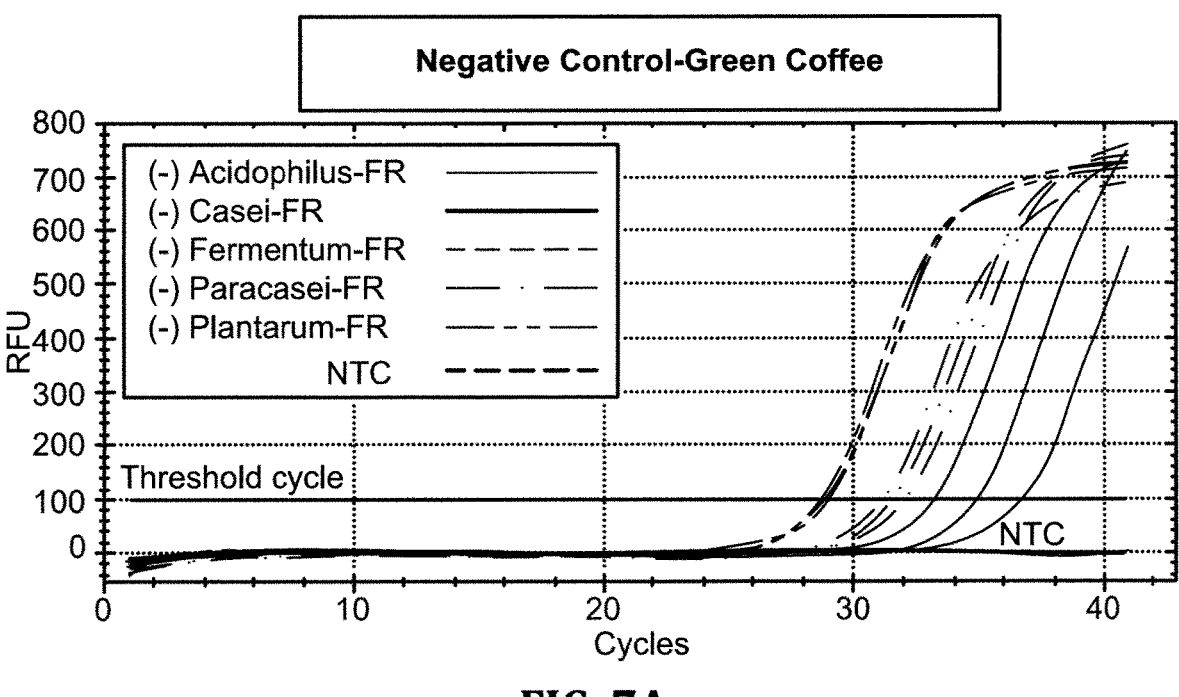
Figure 7C:
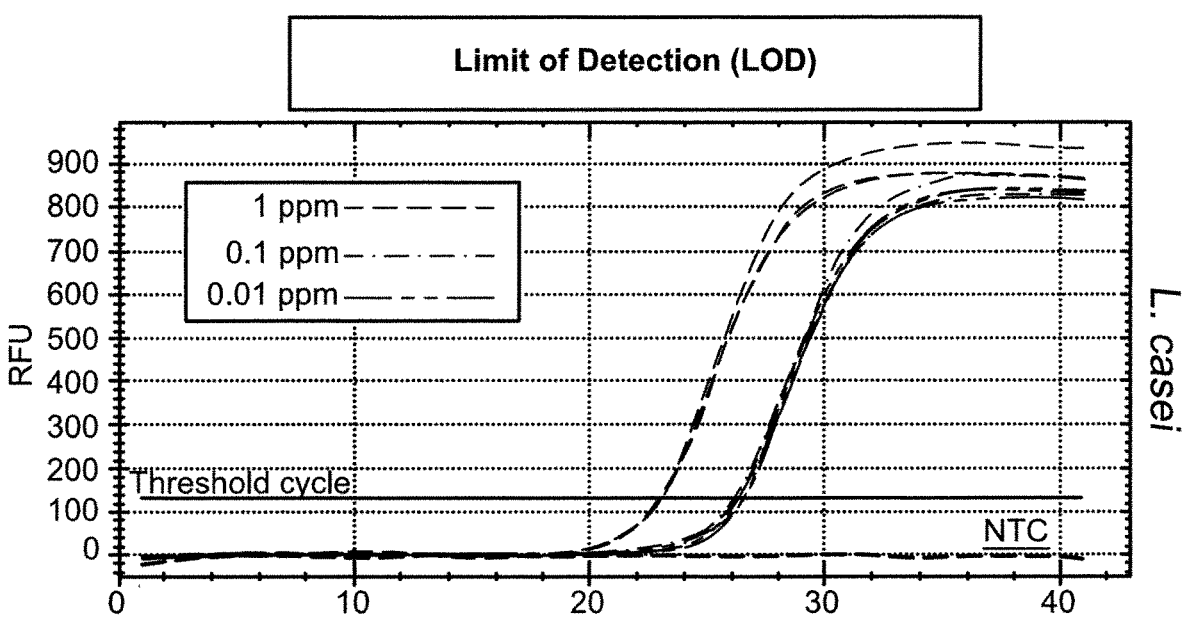

FIGS. 7A-C are real time PCR readouts (Relative Fluorescence Units (RFU) v. Cycles) of tag containing samples with tag concentrations of 10 ppm, 1 ppm, and 0.1 ppm in green coffee including a negative control for *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014) and *Limosilactobacillus fermentum* (ATCC 23271) in green coffee (FIG. 7A); *L. acidophilus* tags in concentrations of 10 ppm, 1 ppm, and 0.1 ppm in green coffee (FIG. 7B); and *L. casei* tags in concentrations of 10 ppm, 1 ppm, and 0.1 ppm in green coffee (FIG. 7C). The x-axis represents the number of cycles, and the y-axis represents the RFUs, or Relative Fluorescence Units, which are proportional to double stranded DNA concentration.

Figure 8A:
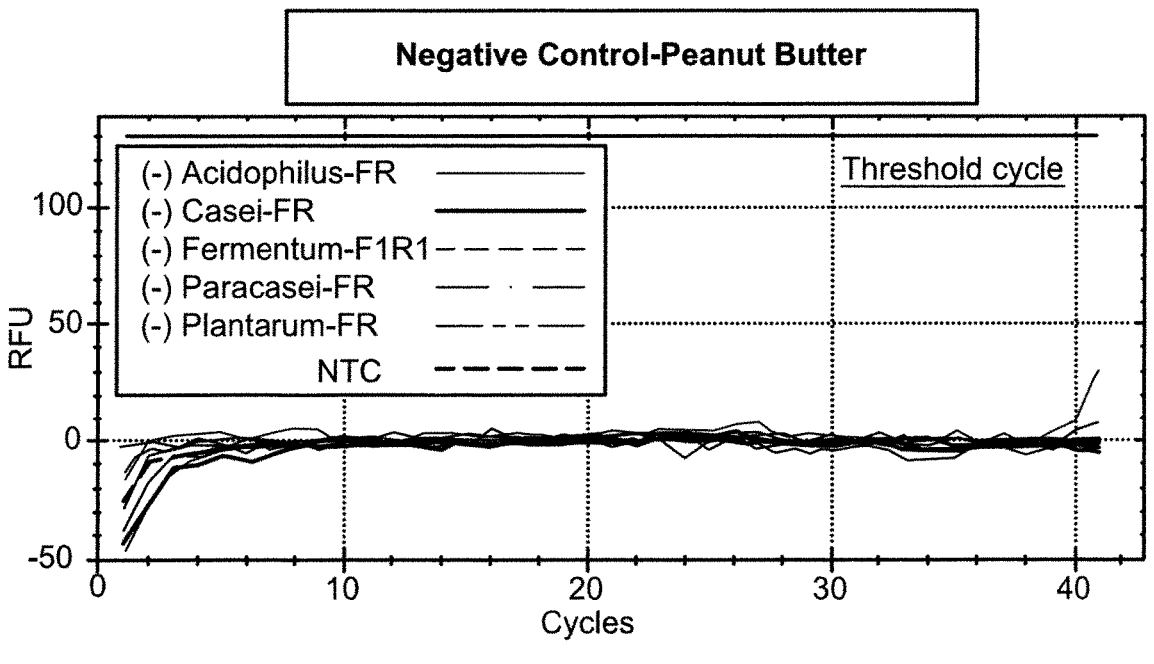
Figure 8B:
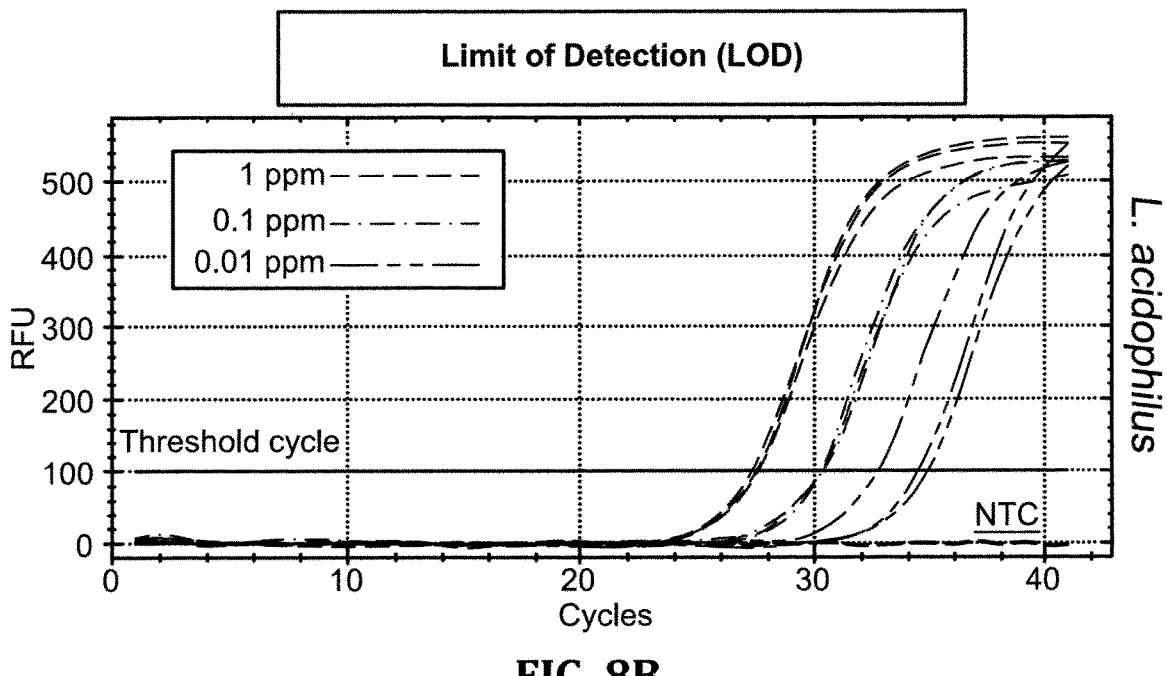
Figure 8C:
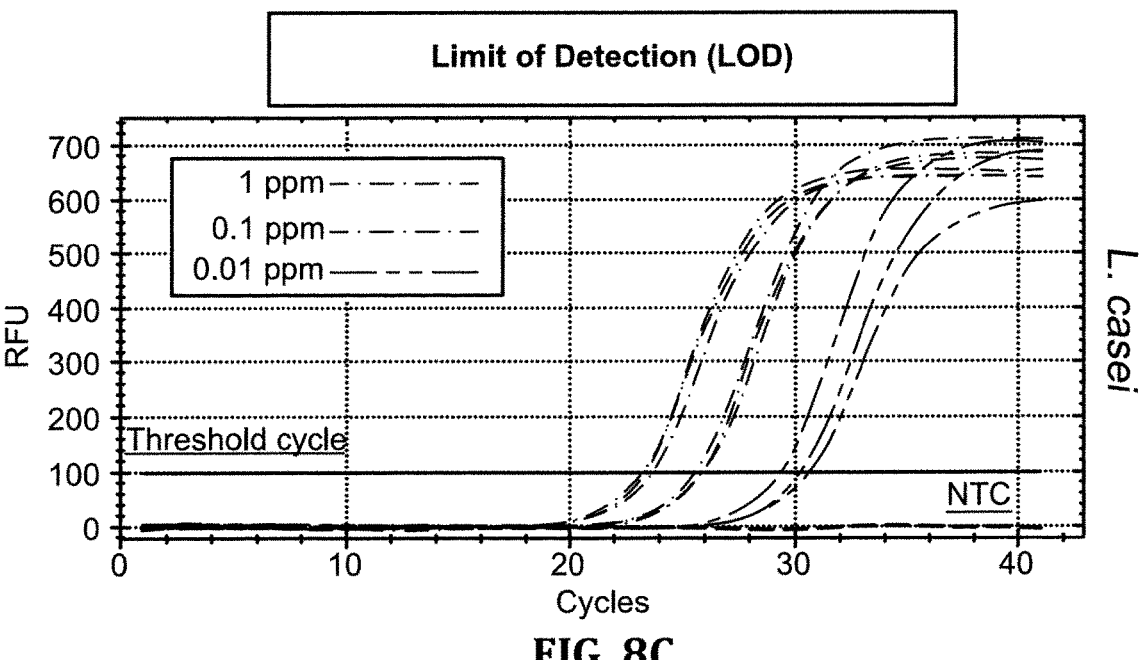
Figure 8D:
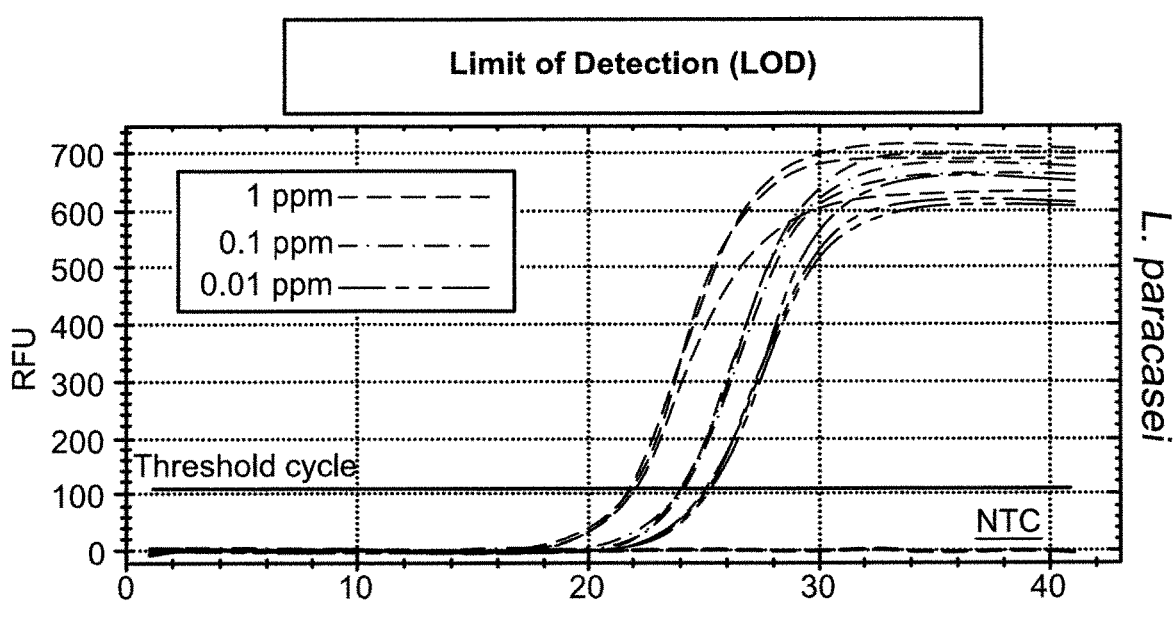
Figure 8E:
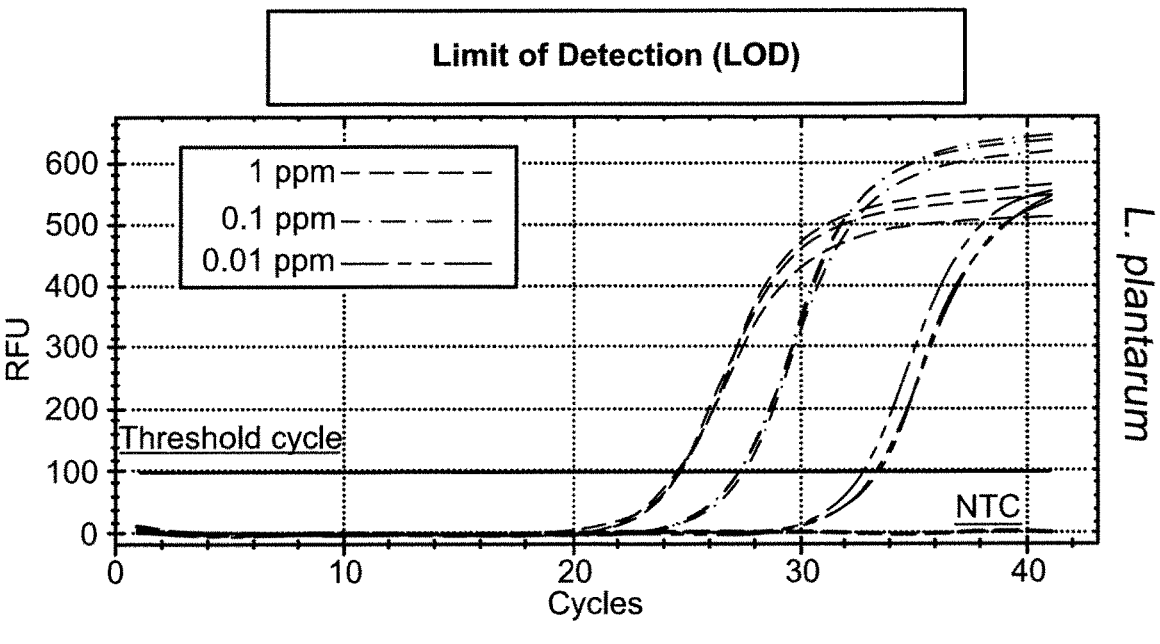

FIGS. 8A-E are real time PCR readouts (Relative Fluorescence Units (RFU) v. Cycles) of tag containing samples with tag concentrations of 10 ppm, 1 ppm, and 0.1 ppm in peanut butter including a negative control for *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014); and *Limosilactobacillus fermentum* (ATCC 23271) in peanut butter (FIG. 8A); *L. acidophilus* tags in concentrations of 10 ppm, 1 ppm, and 0.1 ppm in peanut butter (FIG. 8B); *L. casei* tags in concentrations of 10 ppm, 1 ppm, and 0.1 ppm in peanut butter (FIG. 8C); *L. paracasei* tags in concentrations of 10 ppm, 1 ppm, and 0.1 ppm in peanut butter (FIG. 8D); and *L. plantarum* tags in concentrations of 10 ppm, 1 ppm, and 0.1 ppm in peanut butter (FIG. 8E). The x-axis represents the number of cycles, and the y-axis represents the RFUs, or Relative Fluorescence Units, which are proportional to double stranded DNA concentration.

Figure 9A:
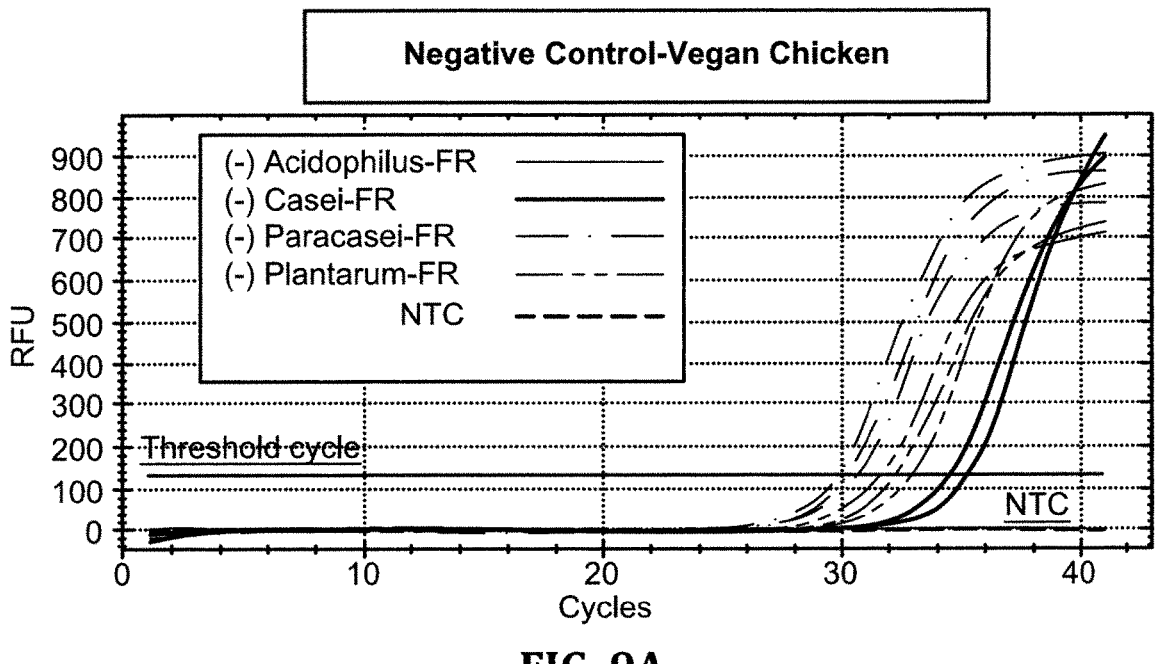
Figure 9B:
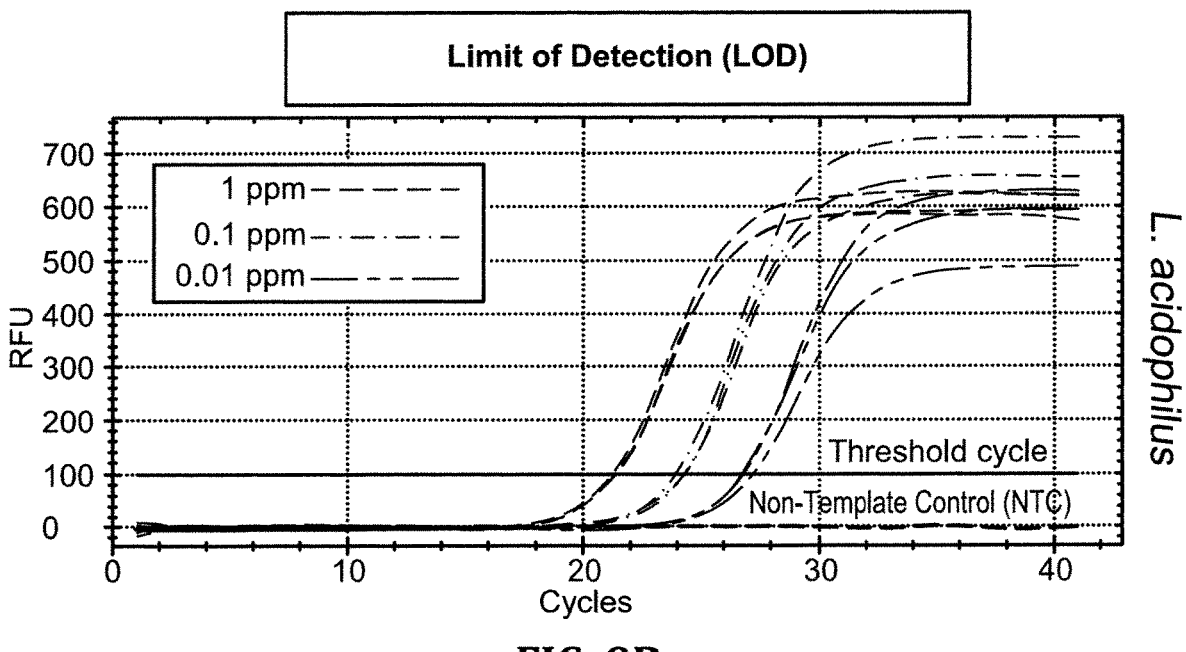

FIGS. 9A-B are real time PCR readouts (Relative Fluorescence Units (RFU) v. Cycles) of tag containing samples with tag concentrations of 10 ppm, 1 ppm, and 0.1 ppm vegan chicken including a negative control for *Lactobacillus acidophilus* (ATCC 4356), *Lactocaseibacillus casei* (ATCC 393), *Lactocaseibacillus paracasei* (DSM 5622), and *Lactiplantibacillus plantarum* (ATCC 8014); in vegan chicken (FIG. 9A) and *L. acidophilus* tags in concentrations of 10 ppm, 1 ppm, and 0.1 ppm in vegan chicken (FIG. 9B). The x-axis represents the number of cycles, and the y-axis represents the RFUs, or Relative Fluorescence Units, which are proportional to double stranded DNA concentration.

Figure 10A:
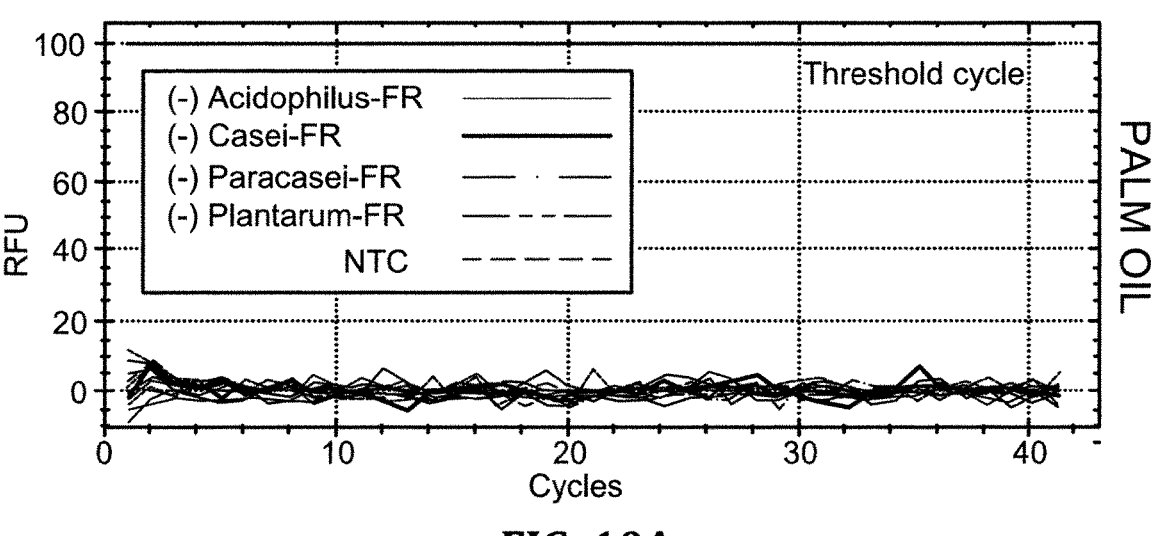
Figure 10B:
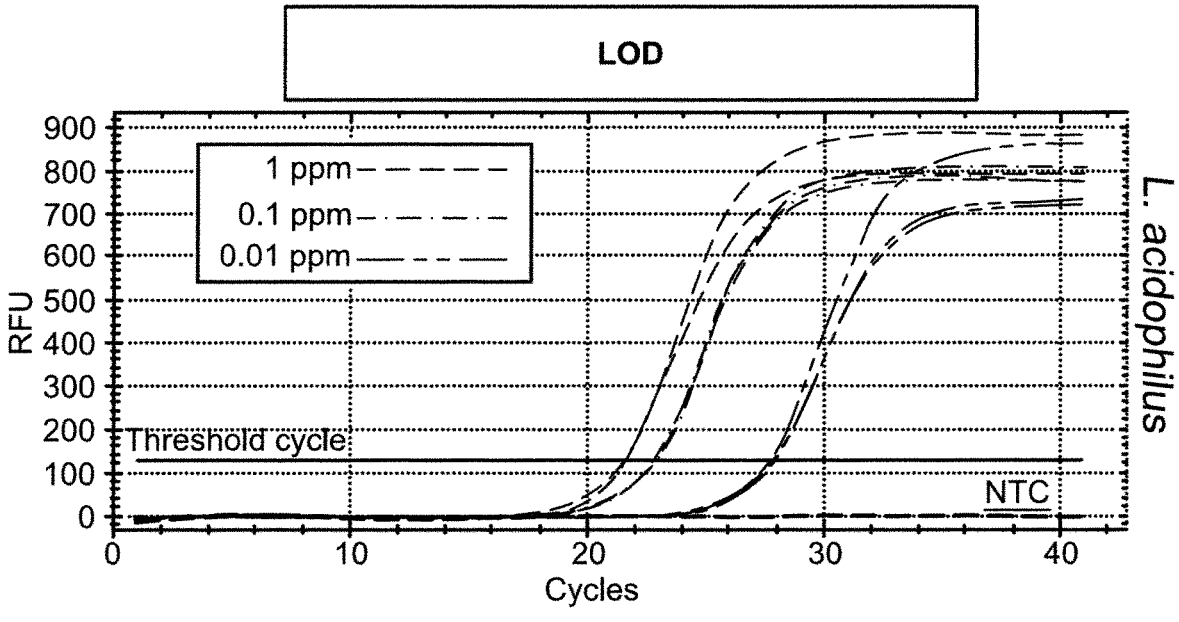
Figure 10C:
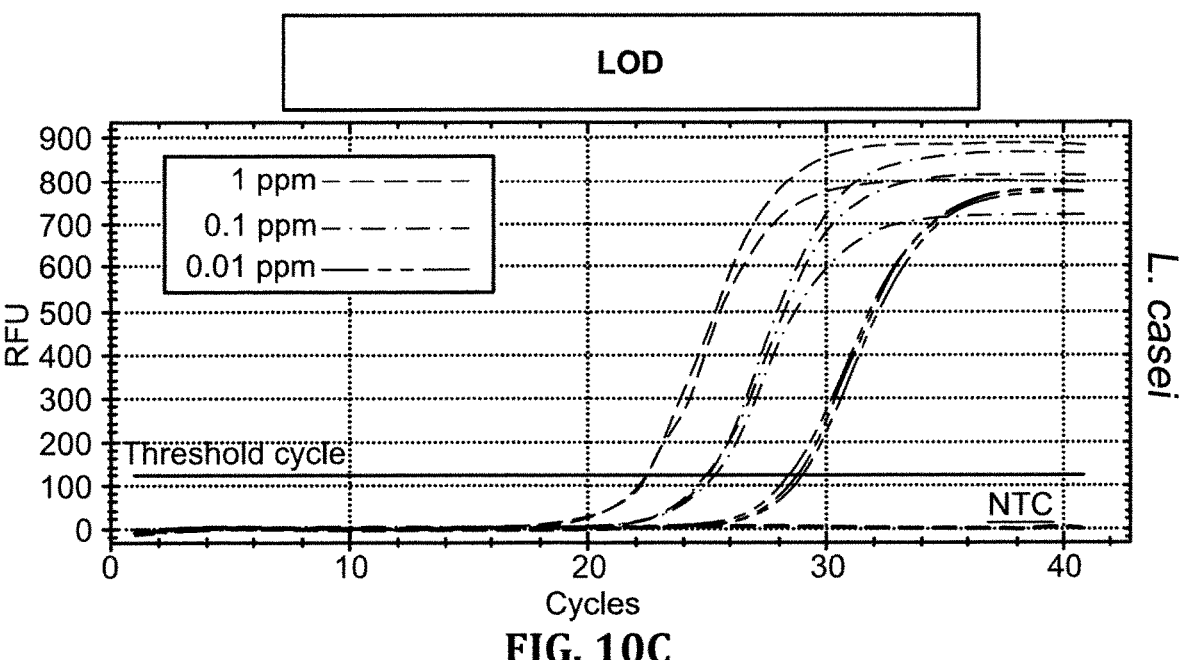
Figure 10D:
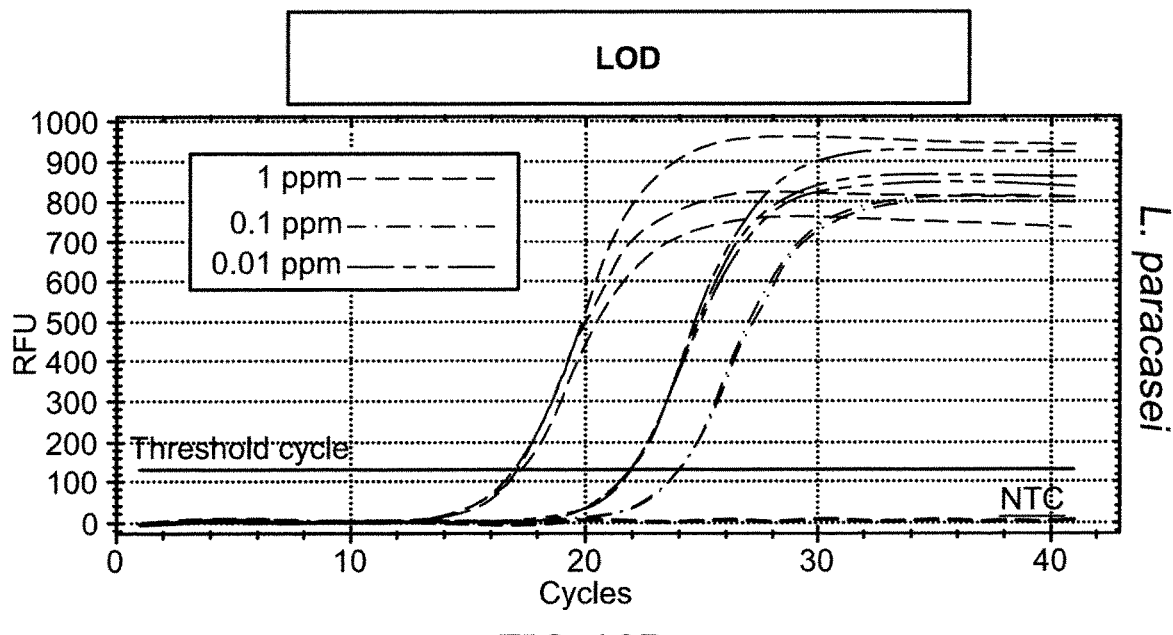
Figure 10E:
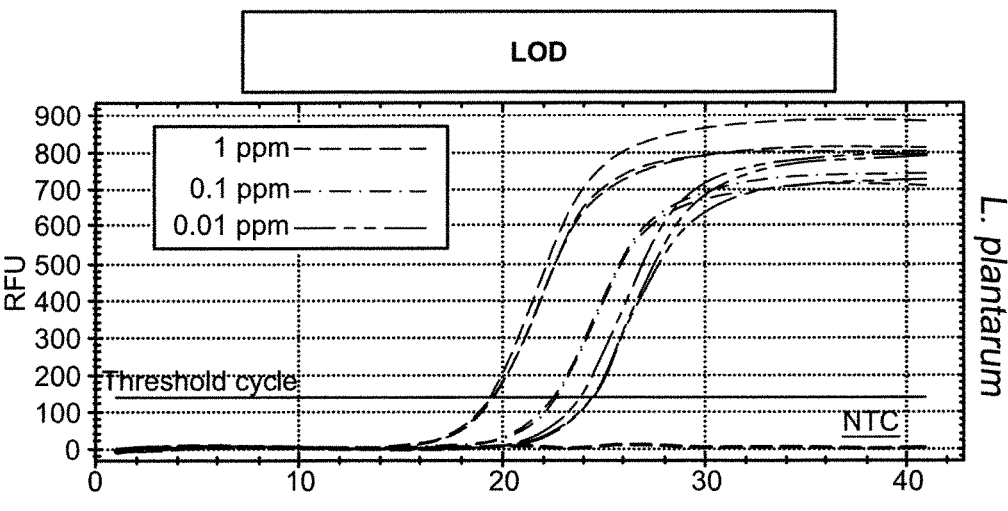

FIGS. 10A-E are real time PCR readouts (Relative Fluorescence Units (RFU) v. Cycles) of tag containing samples with tag concentrations of 10 ppm, 1 ppm, and 0.1 ppm in palm oil including a negative control for *Lactobacillus acidophilus* (ATCC 4356), *Lactocaseibacillus casei* (ATCC 393), *Lactocaseibacillus paracasei* (DSM 5622), and *Lactiplantibacillus plantarum* (ATCC 8014) in palm oil (FIG. 10A); *L. acidophilus* tags in concentrations of 10 ppm, 1 ppm, and 0.1 ppm in palm oil (FIG. 10B); *L. casei* tags in concentrations of 10 ppm, 1 ppm, and 0.1 ppm in palm oil (FIG. 10C); *L. paracasei* tags in concentrations of 10 ppm, 1 ppm, and 0.1 ppm in palm oil (FIG. 10D); and *L. plantarum* tags in concentrations of 10 ppm, 1 ppm, and 0.1 ppm in palm oil (FIG. 10E). The x-axis represents the number of cycles, and the y-axis represents the RFUs, or Relative Fluorescence Units, which are proportional to double stranded DNA concentration.

Figure 11A:
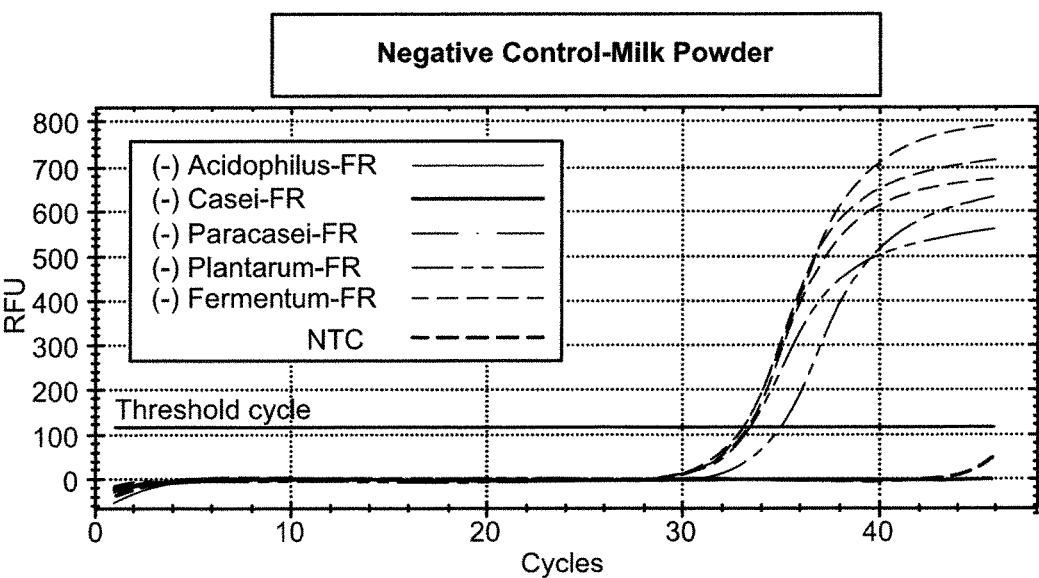
Figure 11B:
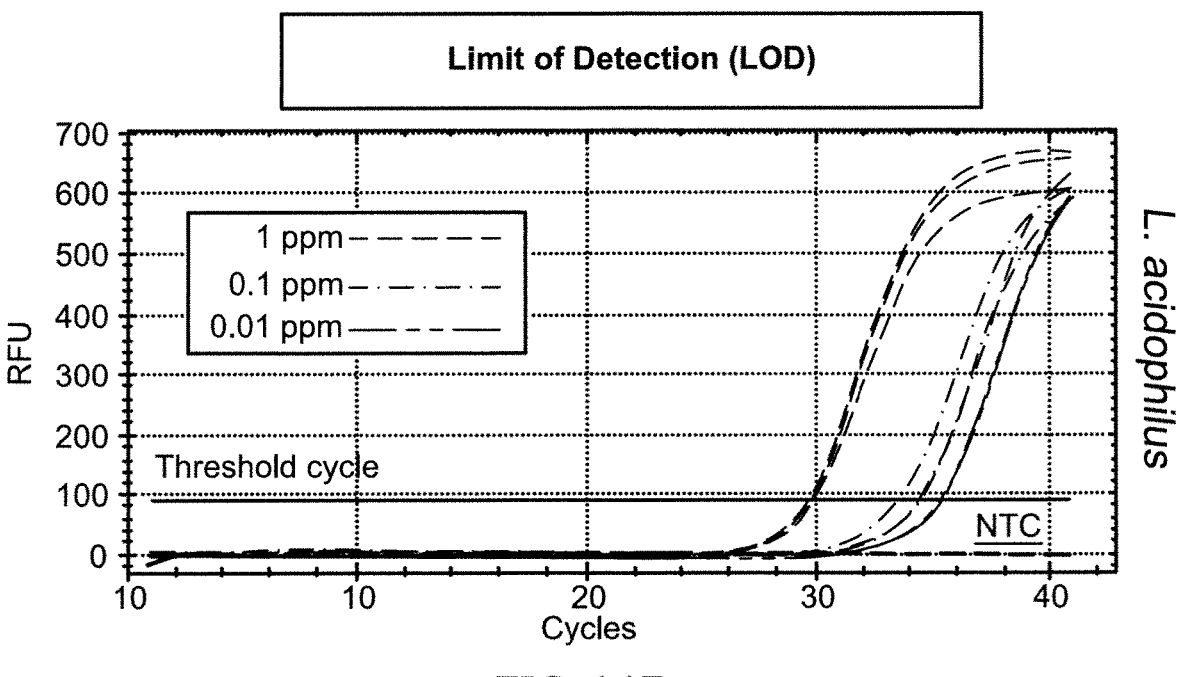
Figure 11C:
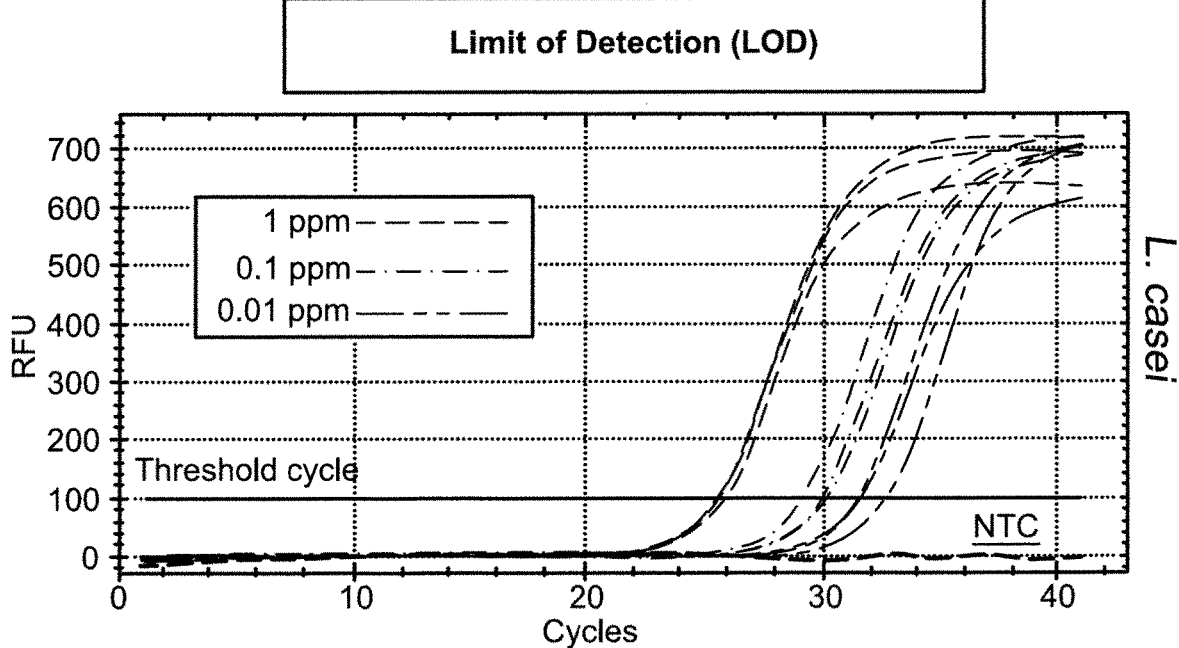
Figure 11D:
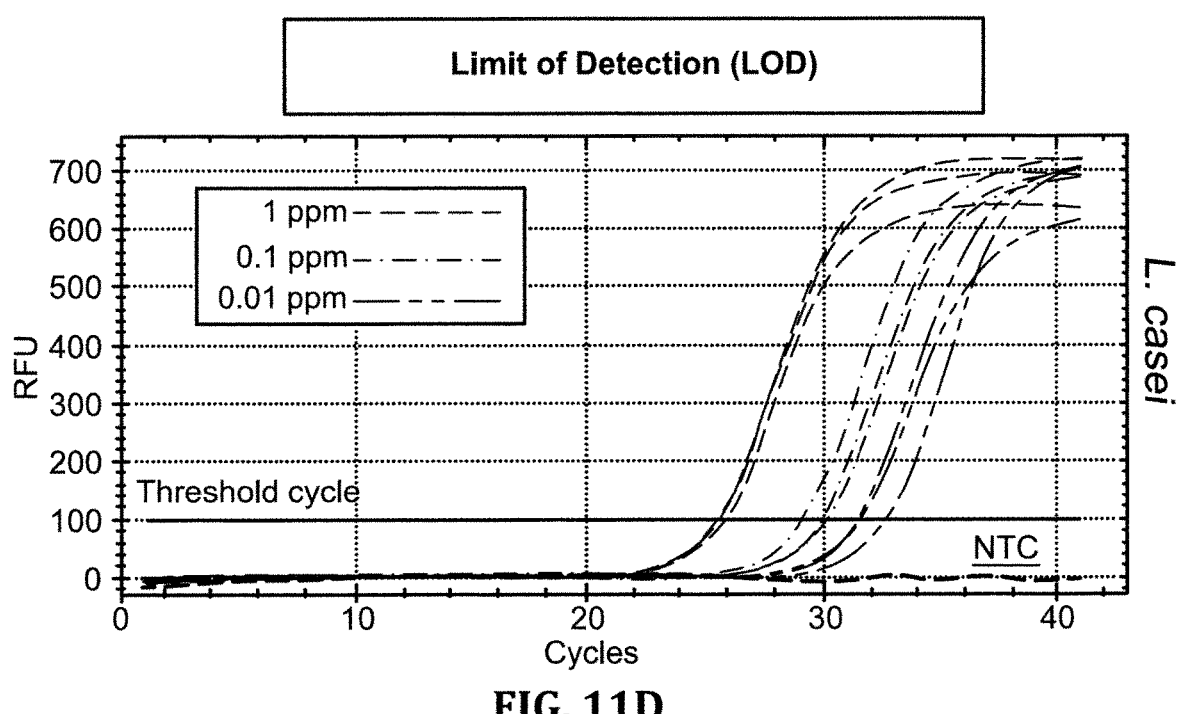

FIGS. 11A-D are real time PCR readouts (Relative Fluorescence Units (RFU) v. Cycles) of tag containing samples with tag concentrations of 10 ppm, 1 ppm, and 0.1 ppm in milk powder including a negative control for *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014); and *Limosilactobacillus fermentum* (ATCC 23271) in milk powder (FIG. 11A); *L. acidophilus* tags in concentrations of 10 ppm, 1 ppm, and 0.1 ppm in milk powder (FIG. 11B); *L. casei* tags in concentrations of 10 ppm, 1 ppm, and 0.1 ppm in milk powder (FIG. 11C); and *L. paracasei* tags in concentrations of 10 ppm, 1 ppm, and 0.1 ppm in milk powder (FIG. 11D). The x-axis represents the number of cycles, and the y-axis represents the RFUs, or Relative Fluorescence Units, which are proportional to double stranded DNA concentration.

Figure 12A:
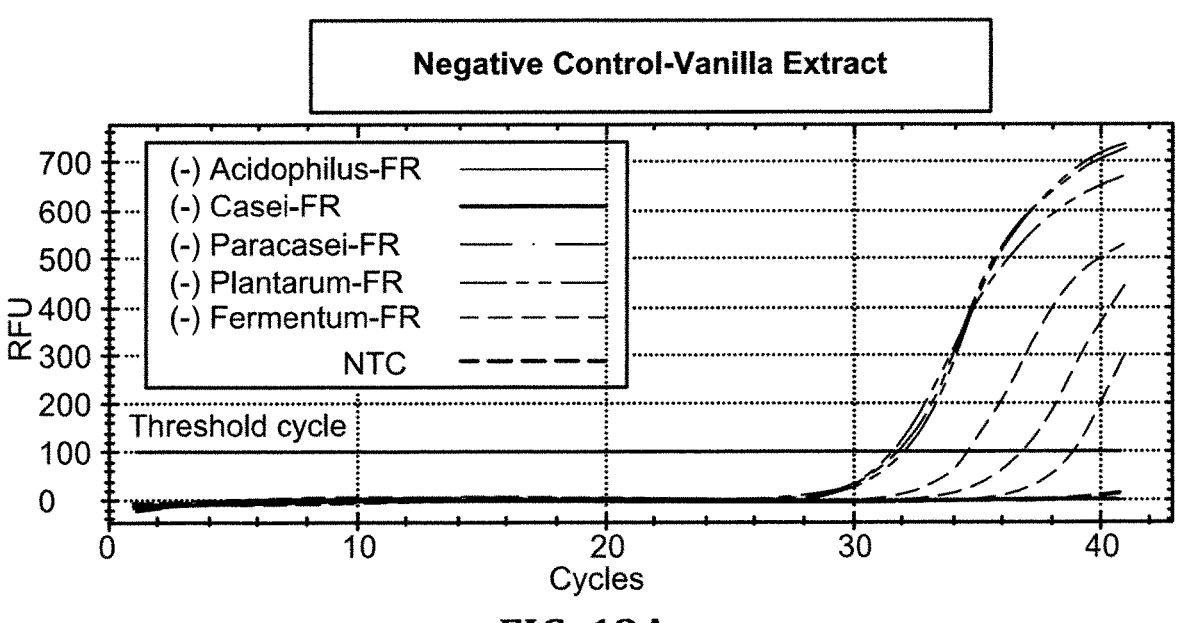
Figure 12B:
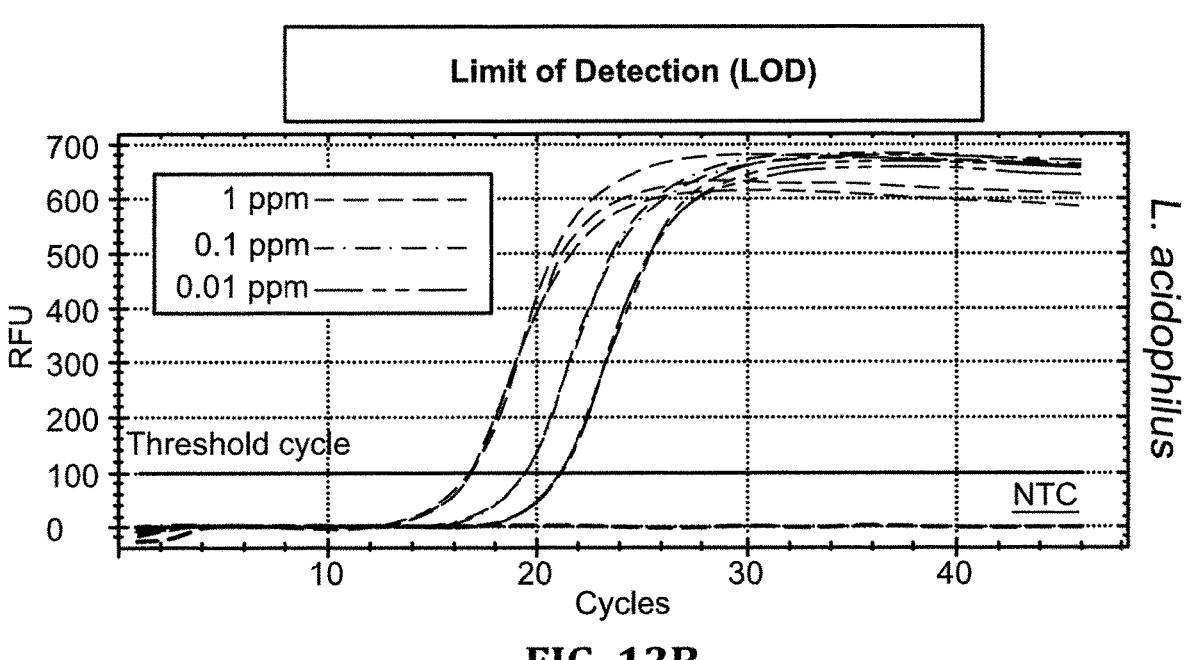
Figure 12C:
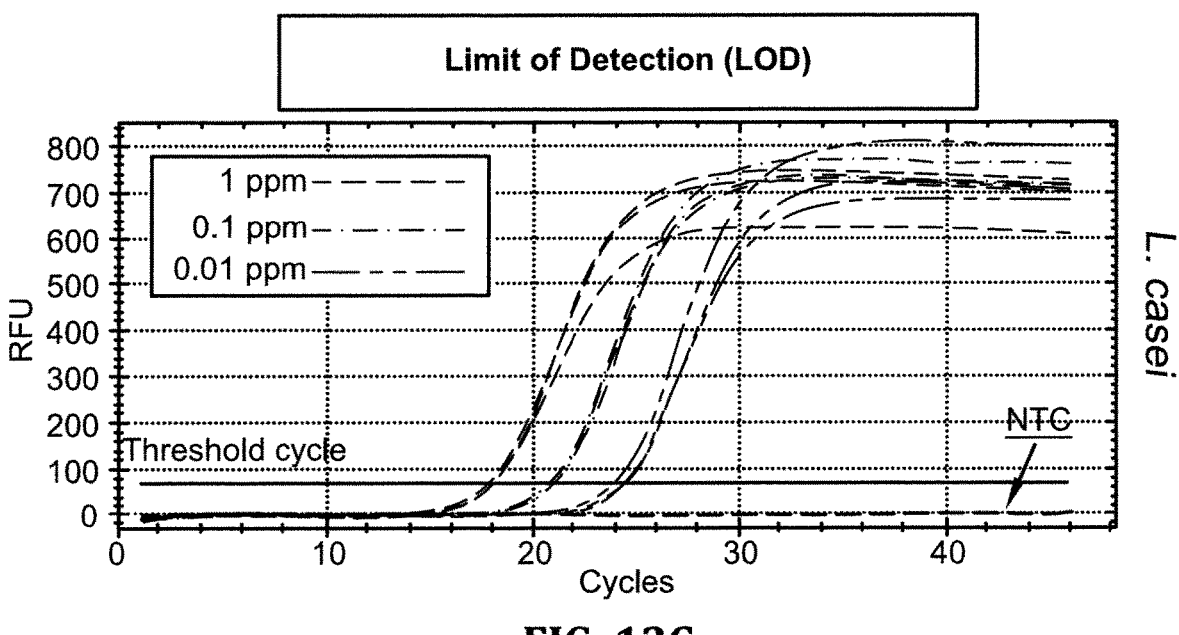
Figure 12D:
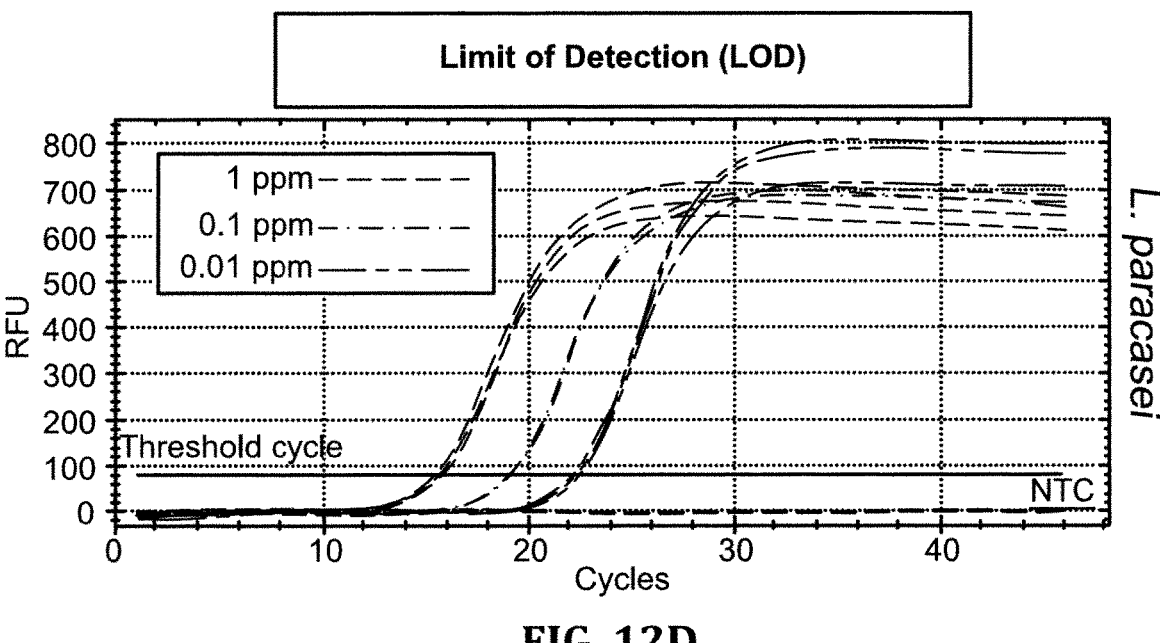

FIGS. 12A-D are real time PCR readouts (Relative Fluorescence Units (RFU) v. Cycles) of tag containing samples with tag concentrations of 10 ppm, 1 ppm, and 0.1 ppm in vanilla extract including a negative control for *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014); and *Limosilactobacillus fermentum* (ATCC 23271) in vanilla extract (FIG. 12A); *L. acidophilus* tags in concentrations of 10 ppm, 1 ppm, and 0.1 ppm in vanilla extract (FIG. 12B); *L. casei* tags in concentrations of 10 ppm, 1 ppm, and 0.1 ppm in vanilla extract (FIG. 12C); and *L. paracasei* tags in concentrations of 10 ppm, 1 ppm, and 0.1 ppm in vanilla extract (FIG. 12D).

The x-axis represents the number of cycles, and the y-axis represents the RFUs, or Relative Fluorescence Units, which are proportional to double stranded DNA concentration.

Figure 13A:
Figure 13A:
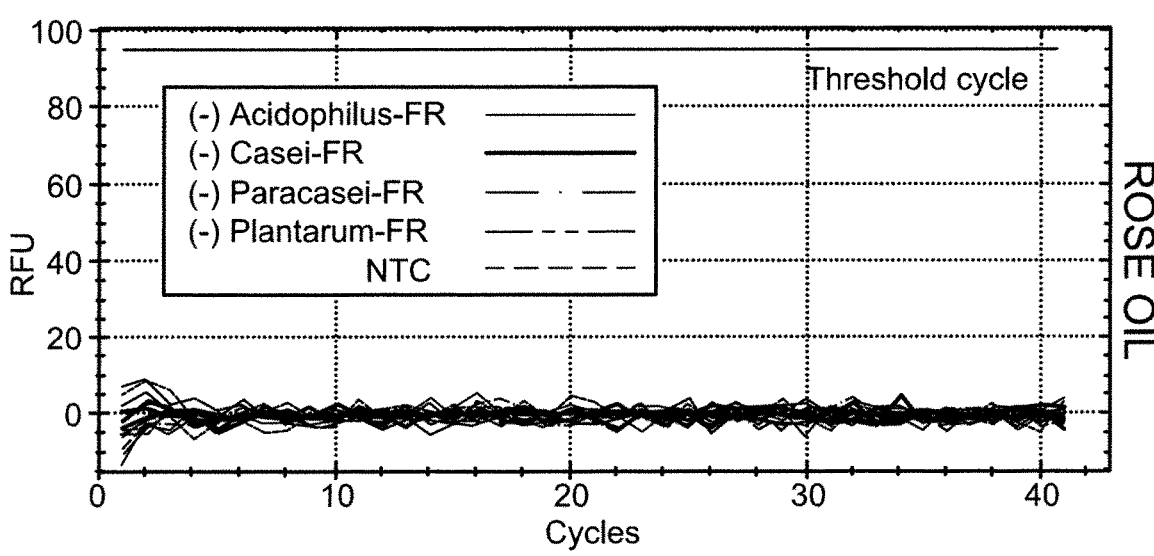
Figure 13B:
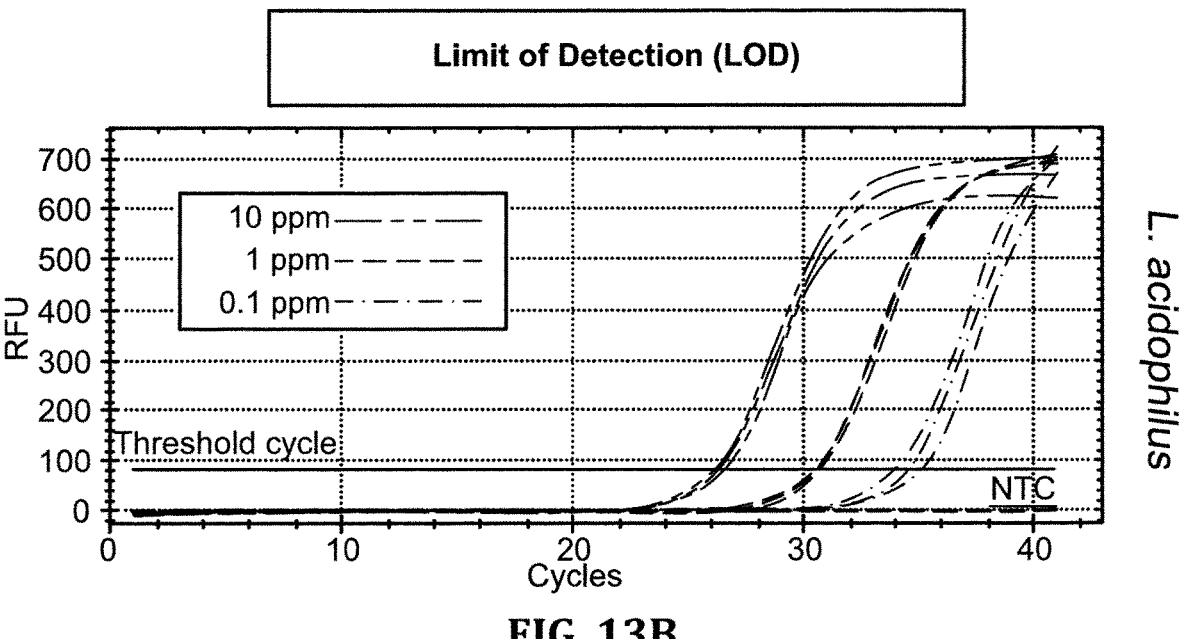
Figure 13C:
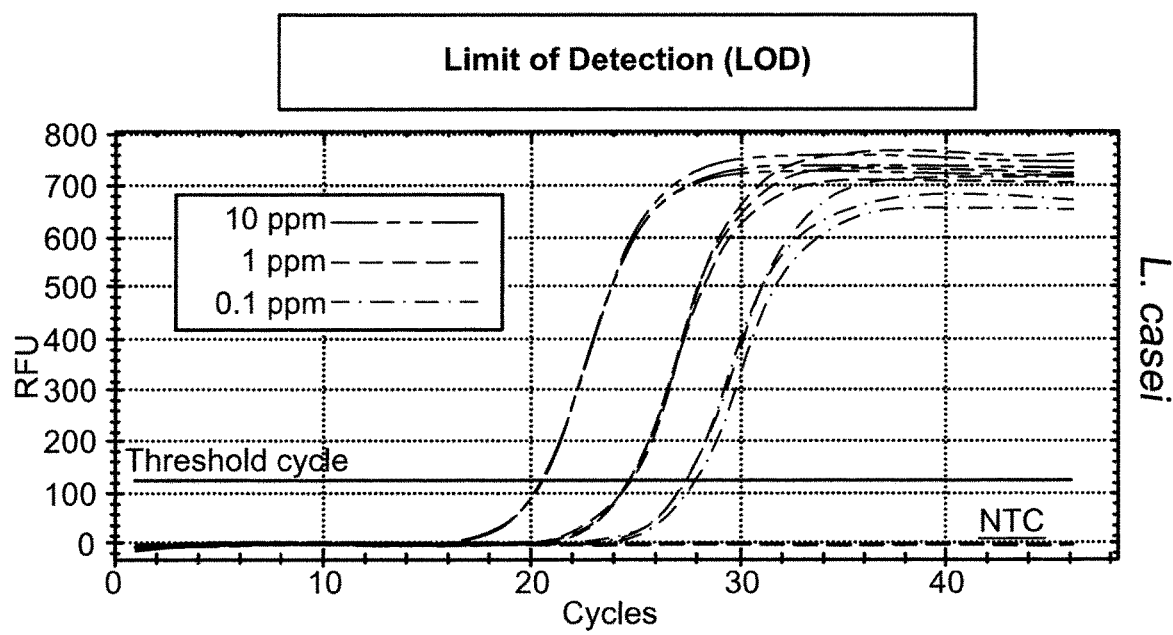
Figures 13D, 13E:
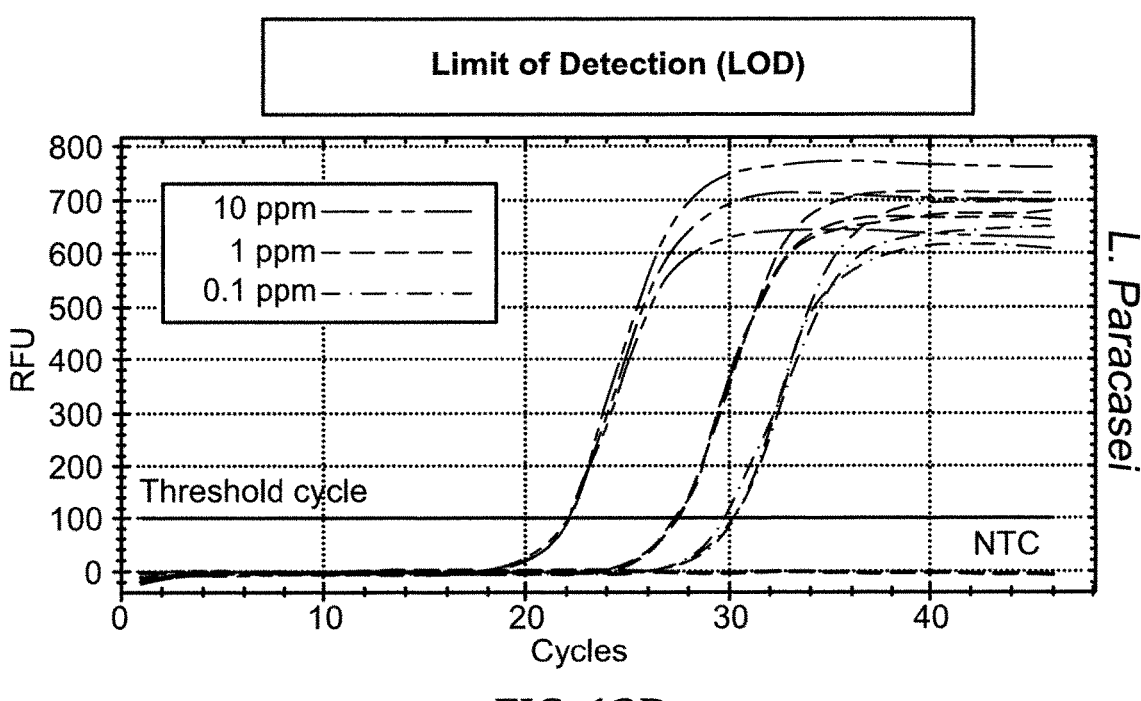

FIGS. 13A-E are real time PCR readouts (Relative Fluorescence Units (RFU) v. Cycles) of tag containing samples with tag concentrations of 10 ppm, 1 ppm, and 0.1 ppm in rose oil including a negative control for *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014); and *Limosilactobacillus fermentum* (ATCC 23271) in rose oil (FIG. 13A); *L. acidophilus* tags in concentrations of 10 ppm, 1 ppm, and 0.1 ppm in rose oil (FIG. 13B); *L. casei* tags in concentrations of 10 ppm, 1 ppm, and 0.1 ppm in rose oil (FIG. 13C); *L. paracasei* tags in concentrations of 10 ppm, 1 ppm, and 0.1 ppm in rose oil (FIG. 13D); and *L. plantarum* tags in concentrations of 10 ppm, 1 ppm, and 0.1 ppm in rose oil (FIG. 13E). The x-axis represents the number of cycles, and the y-axis represents the RFUs, or Relative Fluorescence Units, which are proportional to double stranded DNA concentration.

Figure 14A:
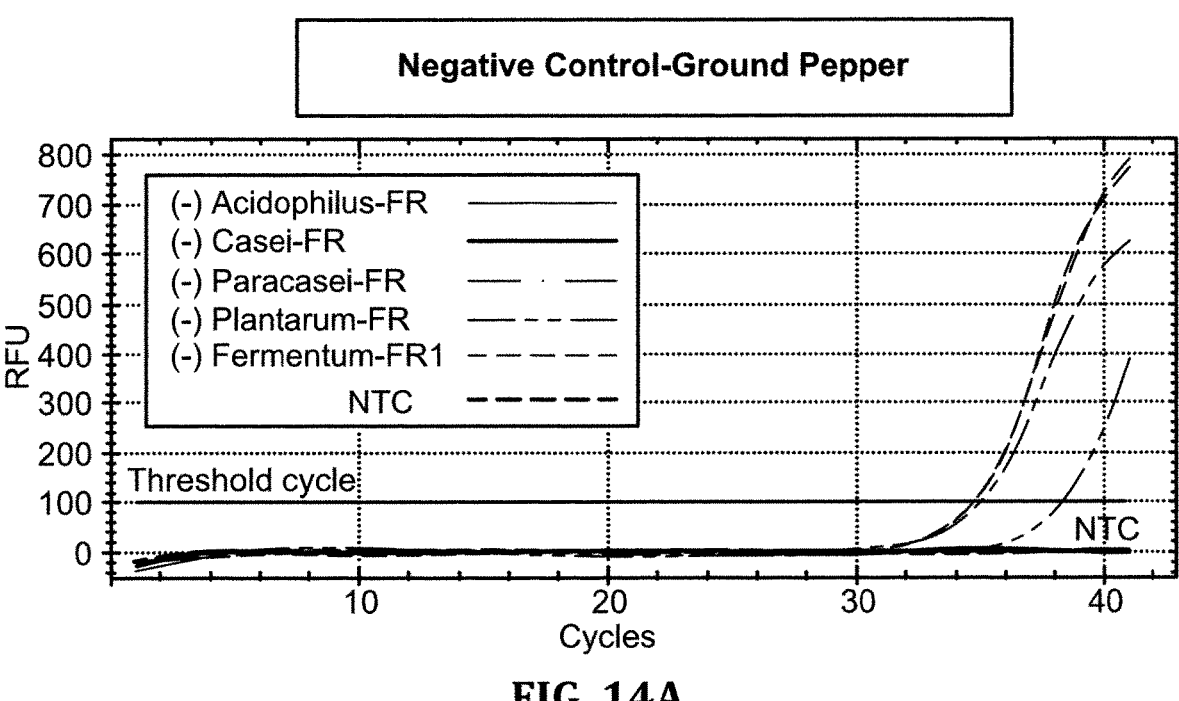
Figure 14B:
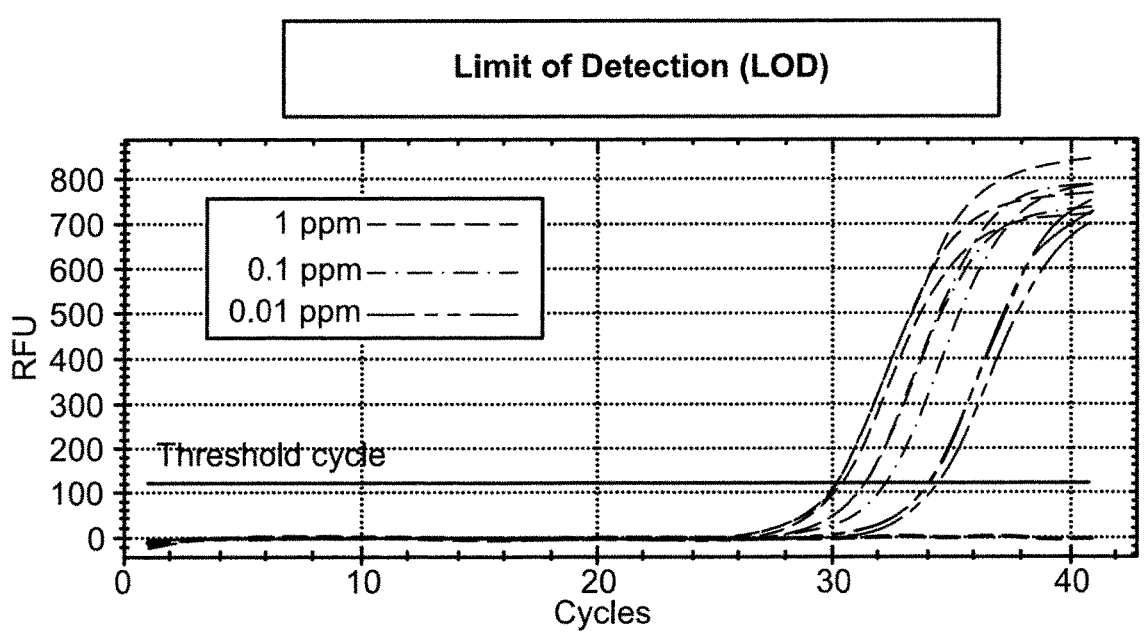
Figure 14C:
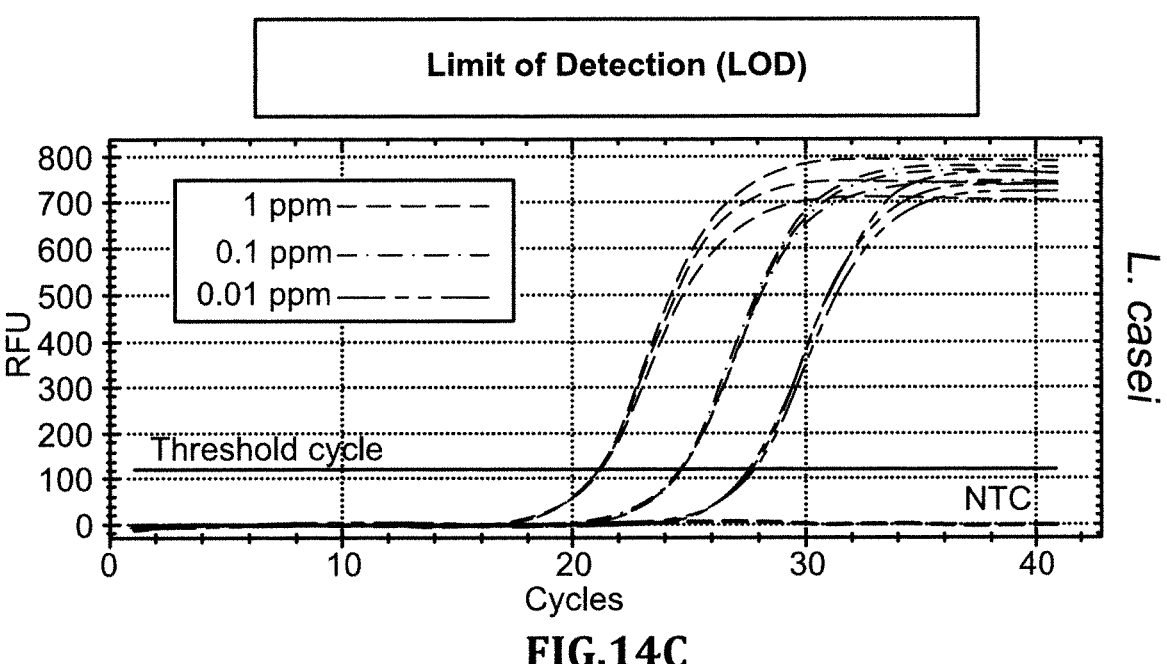
Figure 14D:
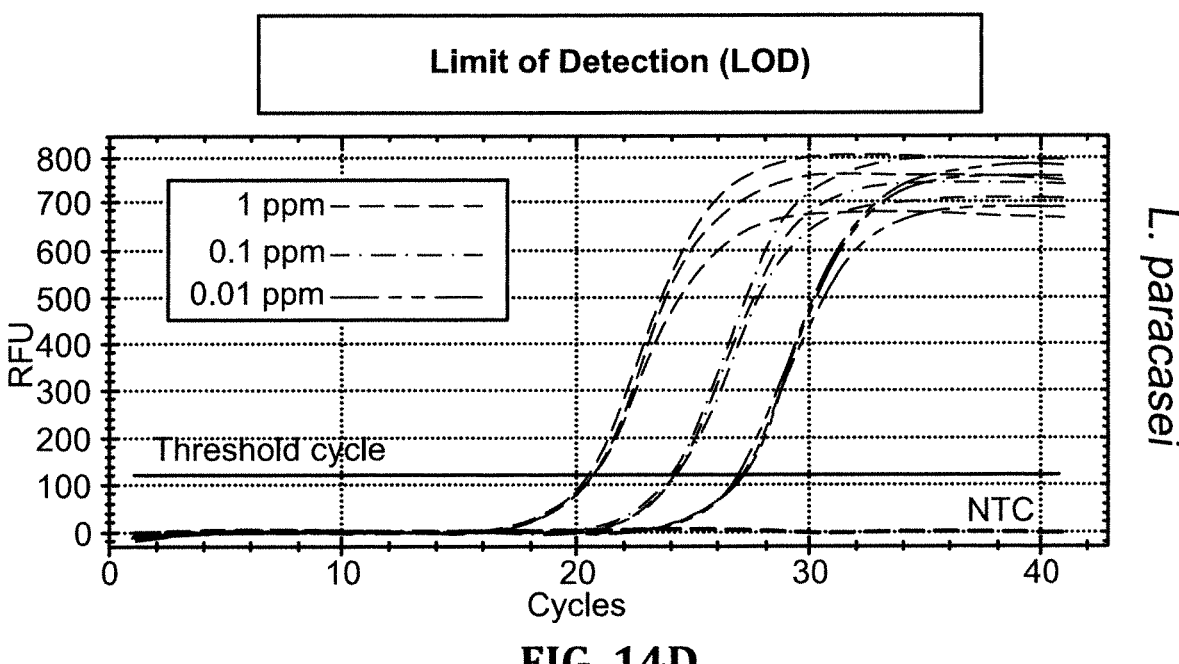

FIGS. 14A-D are real time PCR readouts (Relative Fluorescence Units (RFU) v. Cycles) of tag containing samples with tag concentrations of 10 ppm, 1 ppm, and 0.1 ppm in ground pepper including a negative control for *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014); and *Limosilactobacillus fermentum* (ATCC 23271) in ground pepper (FIG. 14A); *L. acidophilus* tags in concentrations of 10 ppm, 1 ppm, and 0.1 ppm in ground pepper (FIG. 14B); *L. casei* tags in concentrations of 10 ppm, 1 ppm, and 0.1 ppm in ground pepper (FIG. 14C); and *L. paracasei* tags in concentrations of 10 ppm, 1 ppm, and 0.1 ppm in ground pepper (FIG. 14D). The x-axis represents the number of cycles, and the y-axis represents the RFUs, or Relative Fluorescence Units, which are proportional to double stranded DNA concentration.

Figure 15A:
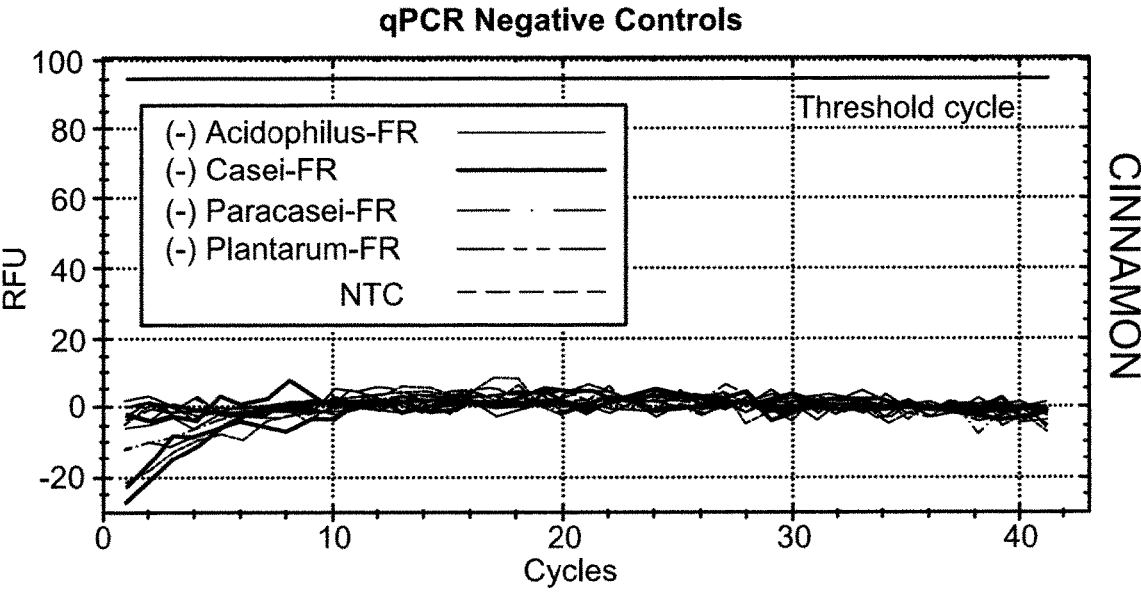
Figure 15B:
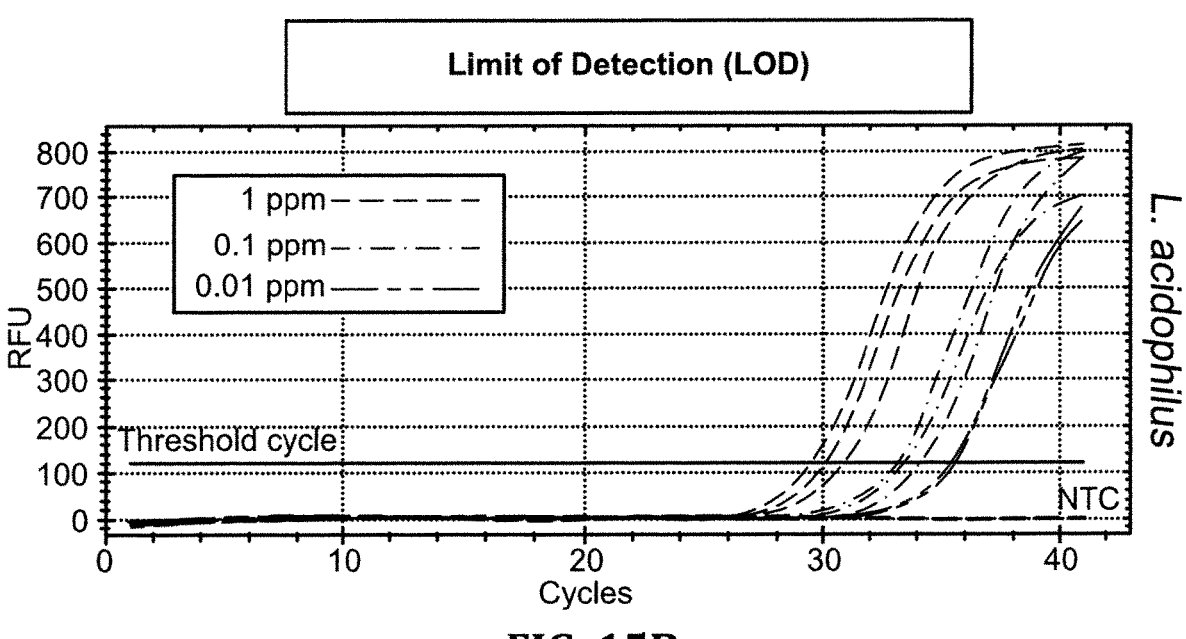
Figure 15C:
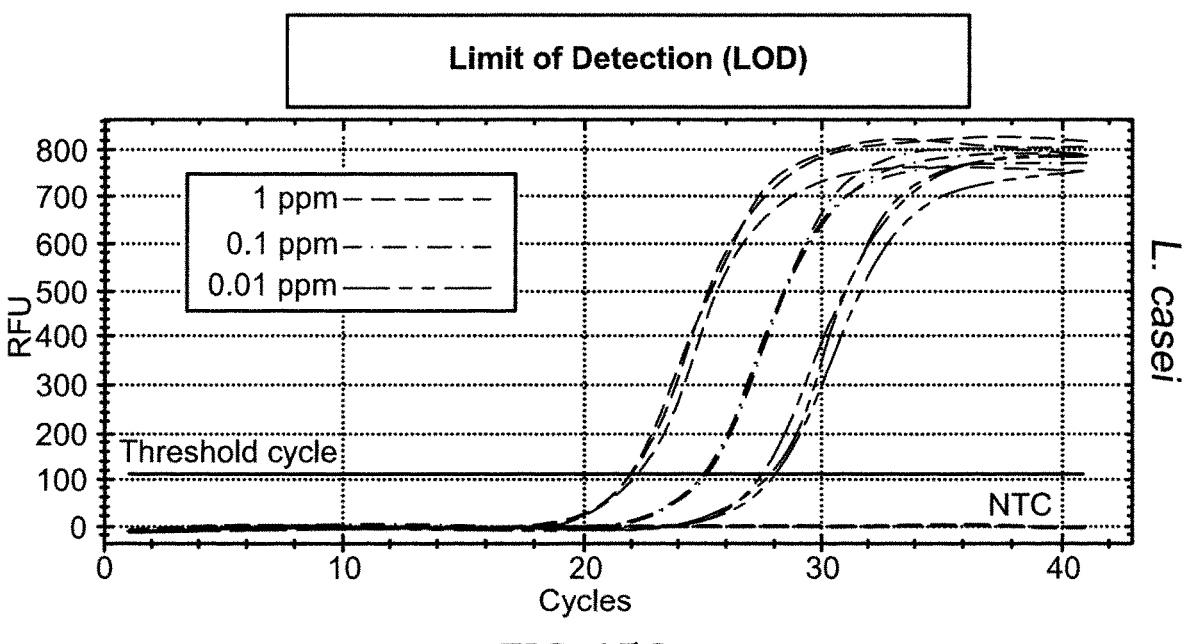
Figure 15D:
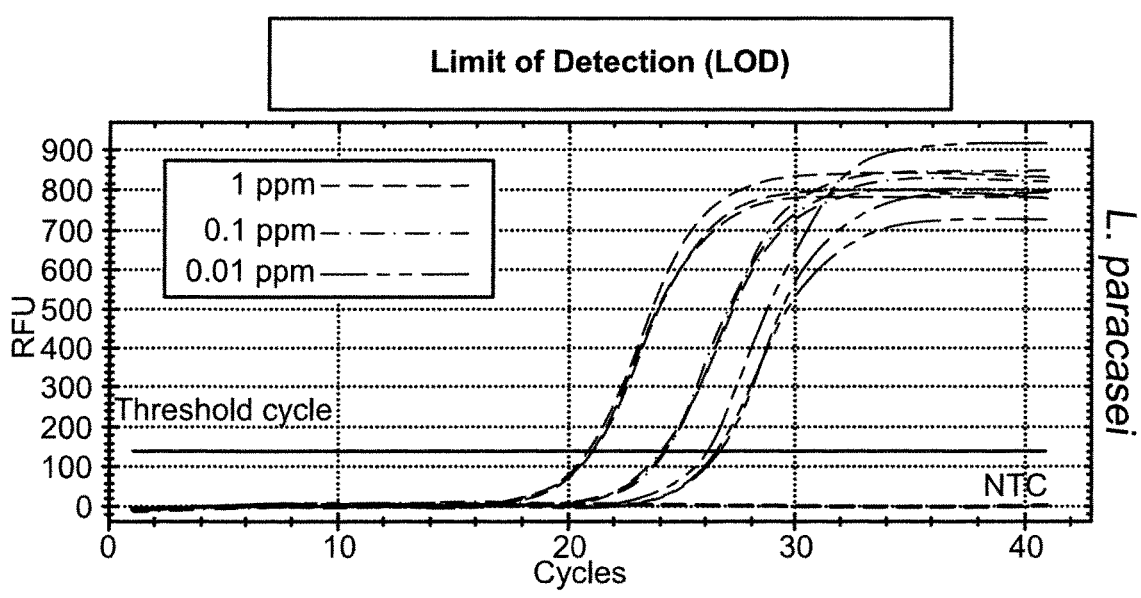
Figure 15E:
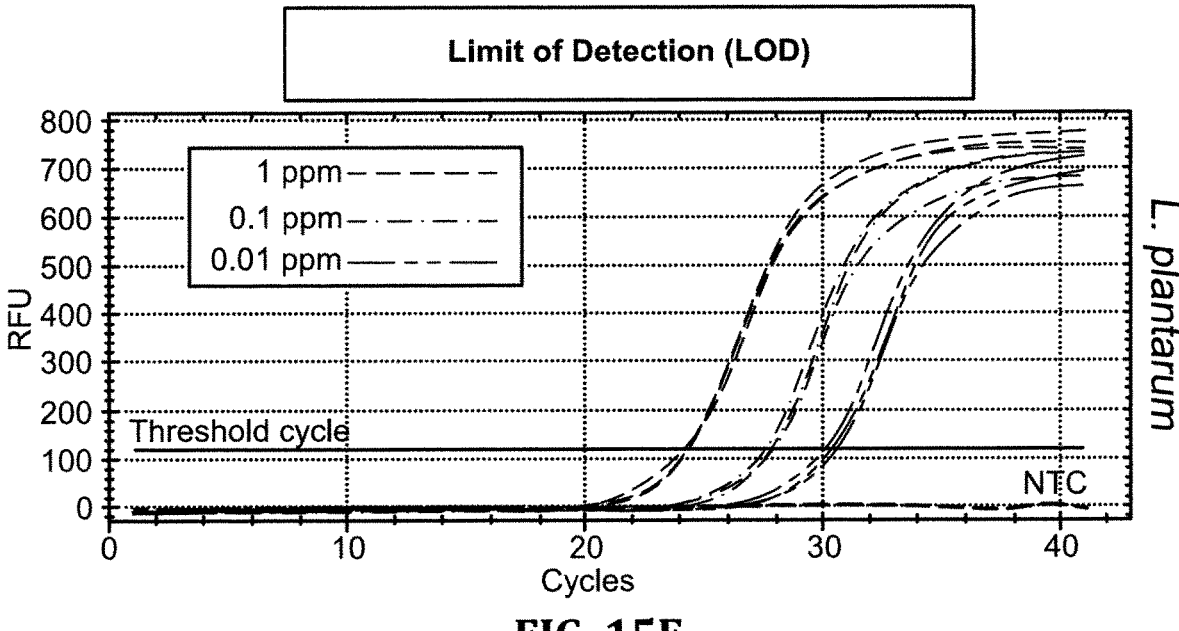

FIGS. 15A-E are real time PCR readouts (Relative Fluorescence Units (RFU) v. Cycles) of tag containing samples with tag concentrations of 10 ppm, 1 ppm, and 0.1 ppm in cinnamon including a negative control for *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014); and *Limosilactobacillus fermentum* (ATCC 23271) in cinnamon (FIG. 15A); *L. acidophilus* tags in concentrations of 10 ppm, 1 ppm, and 0.1 ppm in cinnamon (FIG. 15B); *L. casei* tags in concentrations of 10 ppm, 1 ppm, and 0.1 ppm in cinnamon (FIG. 15); *L. paracasei* tags in concentrations of 10 ppm, 1 ppm, and 0.1 ppm in cinnamon (FIG. 15D); and *L. plantarum* tags in concentrations of 10 ppm, 1 ppm, and 0.1 ppm in cinnamon (FIG. 15E). The x-axis represents the number of cycles, and the y-axis represents the RFUs, or Relative Fluorescence Units, which are proportional to double stranded DNA concentration.

DETAILED DESCRIPTION OF THE ILLUSTRATIVE EMBODIMENTS

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the disclosure herein is for describing specific embodiments only and is not intended to be limiting of the disclosure.

As set forth above, the present invention is directed to a safe, food-compatible (e.g., GRAS), natural, and stable microbial DNA based tagging system scalable to allow tagging using a large number of unique identifiers, allowing lot-level identification of products. The microbial DNA based tagging system uses the unique target nucleotide sequences found in food safe probiotic single cell microorganisms, preferably food-safe probiotic bacteria, to generate one or more unique "tags." Since the active metabolism of some of these microorganisms could have a detrimental effect on the item or product tagged, it is essential to kill the microorganisms before their addition to the product. As will be apparent, the microorganisms are killed without damaging the DNA of the microorganism that will serve as a tag. Moreover, many microorganisms have strong cell walls that protect the microorganism's cell, including the DNA contained in the cells. In some embodiments, the procedures described herein for killing the microorganisms, have been found to reliably kill 100% of the cells, preferably without significantly damaging their DNA or rupturing their cell walls, leaving at least some portion of the cell walls in place to protect the DNA in the cell. The presence of the cell wall, while preferred, is not necessary for practicing the invention and in some embodiments, some or all of the cell wall may be destroyed when the cell is killed.

The genome nucleotide sequences of these killed microorganisms, which have been characterized and are known, are compared to one or more databases of other known genomic nucleotide sequences to identify one or more unique nucleotide sequences, or in any event, one or more sequences that are not naturally present in the item or product being tagged. Each of these sequences, generally referred to herein as "target sequences" or "target nucleotide sequences" may serve as a tag to uniquely identify the item or product. Before their use as a tag, these target nucleotide sequences are recorded and saved in a database, spreadsheet, ledger, block chain, or other similar data management system, and are linked therein to identifying and/or other information that is to be represented by the tag. The terms "tag" and "microbial tag" are used herein interchangeably to refer to a particular target sequence that serves as a unique identifier for a product or other piece of information. Each tag is linked to an entry in a database, spreadsheet, ledger or other similar data management system such that recovery of that that target sequence (i.e., tag) in a product provides information about the product to the user.

In some embodiments, each tag will be assigned a unique identifier number (UID) in a database. In some of these embodiments, the tag may be linked to information in one or more other databases via its UID. In this way, proprietary and other sensitive information and metadata that may be in the database need not be shared with the parties recovering the tags, such as a third-party laboratory conducting the sample analysis. The party or parties recovering the tags only need to have knowledge of the UID linking to the tag sequence, and the linked information or metadata is retained and safeguarded by another entity, such as a corporation offering the tracking services.

As will be apparent, each of these tags can be used to identify any aspect of an item or its provenance in this way. Virtually any feature or aspect of the tagged product may be identified and/or traced by saving it in a field in the database linked to the target sequence "tag" or its UID. In various embodiments, a tag may represent, without limitation, such things as an assigned unique identifier number (UID), the name and location of the producer of manufacturer, shipment information (origin, itinerary, destination information), shipment metadata (temperature, packaging, etc.), lot numbers, production date, expiry date, source, the name and location of distributor or distributors, production methods, the name and location of the licensee or licensees, critical quality parameters, critical process parameters, manufacture or growth conditions, geographical origin/provenance, climate information, environmental information, the use of pesticides and other agricultural practices, other grower metadata, the allergen-free status, the halal/kosher/organic status, the GMO-free status, the fair trade status, the regulatory approval status (e.g., USDA or FDA approval status), other customer information, and combinations thereof.

The killed microorganism containing the "tag" is then added to the product and can be later retrieved and detected using PCR and/or DNA sequencing, to ascertain the identity of the item or specific product tagged. In some embodiments, for example, a food processing company will be able to confirm that the shipment of palm oil it received is actually the RSPO (Roundtable on Sustainable Palm Oil) certified palm oil that it has been represented to be. In some other embodiments, a person or company that has received a defective item or shipment may use the methods of the present invention to determine the source and production lot of the defective product and avoid those products in the future. In still other embodiments, a consumer who has purchased a vanilla latte could analyze the contents of the product and make sure that the product corresponds to his nutritional and ethical consumer preferences. Here and elsewhere, the process allows for detection of multiple markers simultaneously in a product, for example, allowing tracking of the provenance of many ingredients of a final compounded product simultaneously.

The following terms may have meanings ascribed to them below, unless specified otherwise. As used herein, the terms "comprising" "to comprise" and the like do not exclude the presence of further elements or steps in addition to those listed in a claim. Similarly, the terms "a," "an" or "the" before an element or feature does not exclude the presence of a plurality of these elements or features, unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term "about."

It should be also understood that the ranges provided herein are a shorthand for all of the values within the range and, further, that the individual range values presented herein can be combined to form additional non-disclosed ranges. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Further, as used herein, the term "probiotic" refers to live microorganisms that are intended to have health benefits when consumed or applied to the body. As used herein, the term "food compatible" is used refer to a microorganism or other object that is generally considered to be safe consumed by humans and animals and can be used in and around food. As used herein with respect to microorganisms, the term "non-toxic" means that contact with or consumption of the microorganism in question will not adversely affect a human at the concentrations being used. As used herein to refer to a microorganism, food additive, or pharmaceutical additive, the term "generally regarded as safe" means that based upon the scientific literature and/or common usage, the item is not pathogenic, does not produce toxic substances, or is otherwise harmful to humans or pets and is generally understood by those of skill in the art to be safe to use as intended. In one or more embodiments, these items will be listed as "generally regarded as safe" (GRAS) by one or more government regulatory agency, but this need not be the case.

As used herein, the terms "genomic DNA" and "chromosomal DNA" are used interchangeably refer to the deoxyribonucleic acid (DNA) that encodes the genome of an organism. Further, as used herein, the term "plasmid DNA" refer to a small, extrachromosomal deoxyribonucleic acid (DNA) molecule within a cell that is physically separated from chromosomal DNA and can replicate independently. Plasmids are primarily found as small circular, double-stranded DNA molecules in bacteria, but are sometimes present in archaea and eukaryotic organisms.

As used herein, the term "next generation sequencing" (NGS) is used to refer to a group of related high throughput massive parallel sequencing techniques such as sequencing using Illumina (San Diego, CA) HiSeq and related systems, Oxford Nanopore (Oxford, Great Britain) or Pacific Biosystems (Palo Alto, CA) sequencers, Thermo Fisher Scientific (Waltham, MA, USA) (Ion Torrent) among others. Similarly, the term "targeted next generation sequencing" (tNGS) is used to refer to using NGS technology to sequence specific and defined regions of a genome.

All publications, patent applications, patents, and other references mentioned herein are expressly incorporated by reference in their entirety, which means that they should be read and considered by the reader as part of this text. That the document, reference, patent application, or patent cited in this text is not repeated in this text is merely for reasons of conciseness. In the case of conflict between these references and the present disclosure, the present disclosure, including definitions, will control. All technical and scientific terms used herein have the same meaning.

Further, any compositions or methods provided herein can be combined with one or more of any of the other compositions and methods provided herein. The fact that given features, elements or components are cited in different dependent claims does not exclude that at least some of these features, elements or components maybe used in combination together.

In various embodiments, the present invention is directed to a method for confirming the identity of an item or product by means of a microbial DNA tag generally comprising the steps of: identifying a probiotic bacteria or other probiotic microorganism having a cell wall and genomic DNA, wherein said genomic DNA comprises one or more target nucleotide sequences of at least 10 base pairs in length, said target nucleotide sequence not being present in the item to be tagged; selecting at least one of said one or more target nucleotide sequences to serve as a tag, and saving the target nucleotide sequence or sequences selected to serve as a tag and the identity (or any other fact tracked) of the item to be tagged in a database; killing said probiotic bacteria, preferably without extensively damaging or destroying the cell wall or a significant amount of the genomic DNA, to create at least one tag comprising the target nucleotide sequence or sequences selected to serve as a tag, substantially surrounded by the cell wall of the dead probiotic bacteria (although applications where the cell wall is no longer present are also possible); adding one or more of said at least one tag to an item. In various embodiments, the identity of the item tagged is later confirmed by: extracting the DNA from said item and adding primers for each target nucleotide sequence or sequences as recorded in the database; amplifying each of said target nucleotide sequence or sequences using polymerase chain reaction (PCR) techniques; sequencing each amplified target nucleotide sequence; and comparing the nucleotide sequence, using basic local alignment search tools (BLAST) or a similar algorithm, of each amplified target nucleotide sequence generated to the nucleotide sequence saved for the target nucleotide sequence and confirming that they match, thereby confirming the identity of the product.

In some embodiments, the present invention is directed to a method for confirming the identity of an item or product by means of a bacterial tag comprising: adding one or more tags to a product, each of the one or more tags comprising dead bacteria cells having at least one nucleotide sequence comprising a target sequence not otherwise present in the product; recording the identity of the product and the target sequence for later reference; and confirming the identity of the tagged product by: extracting the nucleotide sequence from the product; and adding primers for the target sequence and amplifying the target sequence using polymerase chain reaction (PCR) techniques; sequencing the amplified target sequence; and comparing that sequence to the target nucleotide sequence recorded for the product to confirm the identity of the product.

In some other embodiments, the present invention is directed to a method for confirming the identity of an item or product by means of a bacterial tag comprising: adding one or more tags to a product, where each of the one or more tags comprising dead bacteria cells having at least one nucleotide sequence comprising a target sequence not otherwise present in the product; recording the identity of the product and the target sequence in a database for later reference; and confirming the identity of the tagged product by: extracting and sequencing the DNA found in the tagged product using NGS or other sequencing techniques; and comparing the DNA sequences generated to the target nucleotide sequence recorded for the product to confirm the identity of the product.

The item or product to be tagged is not particularly limited but should be capable of receiving and containing the microbial tag of the present invention in the concentrations necessary for tagging the product without any noticeable change in the item's properties, performance, or function. To ensure that the tags will be available to later confirm the identity or other property of the item or product tagged, the tags are preferably well distributed throughout the item, product, or portion of the product or item that is being tagged. Accordingly, the item or product being tagged will preferably be in a liquid, gel, powder, paste, or similar state at the time the tags are added to permit the easy distribution of the tags throughout the item. This is not, however, required and while not preferred, the item to be tagged may in some embodiments be a solid at the time the tags are applied. In some of these embodiments, the tags are applied topically onto the product embedded in a suitable, food-grade matrix.

In various embodiments, the item may be a commercial product or an ingredient or portion of a commercial product. In one or more embodiments, the tagged item may be a food product, agricultural product, cosmetic product, personal care product, or a pharmaceutical product. In some embodiments, a product may contain a single tag identifying the product. In other embodiments, a commercial product or other item may have more than one tag, each tag identifying something different about the product and its provenance, or its various components.

Figure 1:
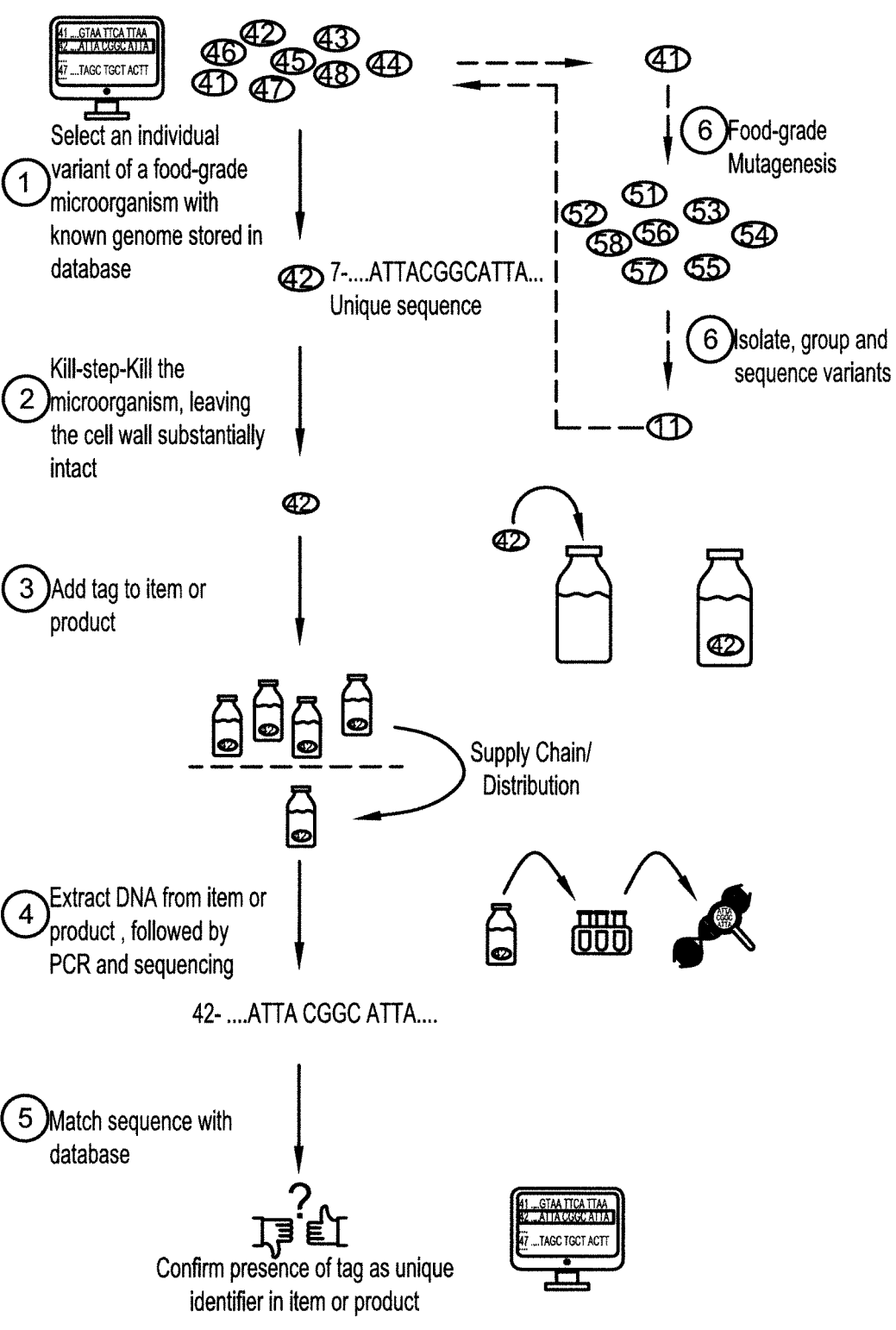
FIG. 1 is a schematic diagram outlining a method of the practicing one or more embodiments of the present invention.

One embodiment of the method of the present invention is outlined in FIG. 1. In the first step, in individual variant of a food-compatible microorganism having a known genome is selected and one or more DNA segments which are unique to that variant of the microorganism are chosen to form the tag.

The microorganisms used to form the tags in the present invention are preferably probiotic or food-compatible bacteria, although probiotic or food-compatible yeasts and other single celled microorganisms may be used in some embodiments. These microorganisms will have a cell wall and genomic, extrachromosomal or plasmid DNA. As will be apparent, the microorganism chosen to serve as the tag should not already be present in the item to be tagged. As will be understood by those of skill in the art, probiotic and/or food-compatible bacteria, like all bacteria, are prokaryotic organisms having diverse but relatively simple structures. Bacteria contain a cell wall but lack a proper nucleus. The genomic or chromosomal DNA, including extrachromosomal DNA and plasmid DNA, in bacteria cells contains the basic genetic code for the bacteria and is found in an area of the cytoplasm generally referred to as the nucleoid. It generally consists of one or more circular chromosomes. In addition to the genomic DNA, the cytoplasm of many bacteria may also contain one or more plasmids, which are relatively short circular segments of DNA, which replicate independently of the genomic DNA.

In one or more embodiments, the tags of the present invention may be derived from either genomic or plasmid DNA, but are preferably derived from the genomic DNA of the probiotic bacterial used.

In addition to chromosomal locations of tags, sequences located in plasmids can be used as tags, if they fulfill the same constraints as the chromosomal sequences in terms of uniqueness described above. For food applications, only naturally occurring plasmid sequences can be used.

The probiotic microorganisms used in the present invention have a cell wall surrounding and protecting the cell. Certain bacterial cell walls consist of complex peptidoglycans (polysaccharides linked to proteins) that form a rigid shell around bacterial cells, protecting the cells from various physio-chemical stresses such as osmotic shock, toxic chemicals, and physical forces such as shearing and pressure, which affords the enclosed DNA a certain level of protection from degradation not otherwise available.

While the microorganisms used to form the tags are killed before insertion into the product tagged, the microorganisms used are preferably probiotic and, in any event, should not be pathogenic, produce toxic substances, allergenic, or otherwise harmful to humans or animals. Particularly for applications in the food industry, the microorganisms used in the present invention will be food compatible, non-toxic, and generally understood to be safe for consumption. In one or more embodiments, the microorganisms used in the present invention will be identified or confirmed by the United States Food and Drug Administration (FDA) as food additives that are generally regarded as safe (GRAS) under applicable statutes. In some embodiments, the microorganisms used in the present invention will be identified or confirmed by comparable European regulatory bodies as food additives that are generally regarded as safe (GRAS) under applicable statutes. In one or more embodiments, the microorganisms, and their source where applicable, will be compatible with vegetarian, vegan, halal, kosher, and other common food regimes.

As set forth above, in some embodiments, the microorganisms used to form the tags are probiotic bacteria. Suitable probiotic bacteria may include, without limitation, Firmicutes (lactobacillus), actinobacteria (bifidobacteria), and combinations thereof. In one or more embodiments, the microorganisms used to form the tags will be probiotic bacteria such as Bifidobacterium animalis subsp. Lactis (BB12), Bifidobacterium bifidum (LMG 11041), Bifidobacterium longum (ATCC 15708), Bifidobacterium longum subsp. Infantis (LMG 8811), Enterococcus faecium (ATCC 6057), Lactobacillus acidophilus ATCC 4356), Lactocaseibacillus casei (ATCC 393), Lb. delbrueckii subsp. Bulgaricus (ATCC 11842), Lactocaseibacillus paracasei DSM 5622), Lactiplantibacillus plantarum (ATCC 8014), Lactocaseibacillus rhamnosus (ATCC 53103), Ligilactobacillus salivarius (ATCC 11741), Lactococcus lactis (ATCC 19435), Lactobacillus reuteri (LMG 9213), Lactobacillus helveticus (ATCC 15807), and/or a combination thereof.

In some other embodiments, the microorganisms used to form the tags will be Streptococcus salivarius subsp. Thermophilus Str. thermophilus (LMG 6896). In some other embodiments, the microorganisms used to form the tags will be Bifidobacterium longum IM 937 (ATCC 15708).

As set forth above, the genomic DNA of the microorganism used to form the tags of the present invention will have one or more DNA segments which are not found in the products to be tagged. In some embodiments, the genomic DNA used to form the tags of the present invention will have one or more DNA segments which are unique to that microorganism. In some other embodiments, however, the genomic DNA used to form the tags need not have one or more DNA segments which are globally unique, provided that it contains one or more segments that are not present in the item being tagged and can be used to form the tag. In various embodiments, these DNA segments may include coding or non-coding DNA sequences. In some embodiments, these DNA segments will be non-coding DNA sequences. In various embodiments, each tag will comprise a target nucleotide sequence isolated from one or more of these DNA segments.

As there are a finite number of naturally occurring unique nucleotide sequences, additional genetic diversity in potential target sequences may, in some embodiments, be added by inducing natural sequence variation as shown in steps 6 and 7 of FIG. 1. (See also, Example 11, below). In these embodiments, the probiotic bacteria or other microorganisms being used to form the tags are subjected to a level of radiation necessary to stimulate mutations in their genomic DNA. In one or more of these embodiments, the probiotic bacteria are subjected to X-ray radiation, UV light (sunlight for 10 to 600 min or light at a wavelength of 254 nm for several seconds up to 5 minutes), or chemical treatment, when the cell cultures reach an OD of approximately 0.4 at 600 nm. (See, e.g. Example 3 and 4).

In one or more embodiments, prior to UV treatment, 2 mL of overnight cultures of the tag strain are washed three times with sterile saline solution and mixed with 18 mL of saline solution. Induction of natural sequence variation by UV is then carried out by exposure of overnight cultures to UV light (254 nm) 1.5 or 6 min, depending on the nature of the strain. In some of these embodiments, the distance between the UV light and tubes with culture is about 35 cm. Serial dilutions of treated cultures are then plated on MRS agar. In these embodiments, the plates are then incubated at 37° C. for 48 h, in the dark. Single colonies are stored in MRS broth with 30% glycerol at −80° C. Later they are tested for survival in simulated gastric and intestinal juice as described previously in Seme et al., "Generation of *Lactobacillus plantarum* strains with improved potential to target gastrointestinal disorders related to sugar malabsorption" Food Res Int. 2017 April; 94:45-53. (doi: 10.1016/j.foodres.2017.01.022. Epub 2017 Jan. 27), the disclosure of which is incorporated herein by reference in its entirety.

As will be apparent, these processes will cause a small number of mutations in the genomic DNA of the bacterial cells. (See, e.g., Tables 12-16 in Appendix 1) The level and/or duration of radiation should not be such that the bacteria cells are killed or rendered unable to divide and grow. In various embodiments, the protocol is adjusted such that the number of mutations induced is on the order of 10-100 per cell, such that the probability of detecting a mutation in a target region of several kilobases is about 10%. After irradiation, the mutated bacteria are isolated and grown and then sequenced to determine whether there have been mutations that create unique sections of DNA that can be used to create one or more tags. If not, the radiation may be repeated as often as necessary to achieve the desired diversity. In this way, a great many additional unique sequences may be created for use as tags in the present invention. Preferably, these mutations will not contain changes in the part of the DNA to which the primers will attach and the same primers may be used with these sequences. In some embodiments, however, new primers may need to be generated for these sequences.

The nucleotide sequences for the genomic DNA of many bacteria and yeast are known and publicly available and if not, can be readily ascertained using conventional methods, including, but not limited to Sanger sequencing, tNGS sequencing, or whole genome sequencing. To identify segments of this DNA that are unique or, in any event, not present in the item being tagged, the genomic DNA of the microorganism in question is compared to various DNA databases, such as Genbank, SwissProt, or EMBL, using basic local alignment search tools (BLAST), BLASTn, FASTA, FAST-N, Smith-Waterman algorithm, or similar techniques. BLAST is publicly available from National Center for Biotechnology Information (NCBI) at https://blast.ncbi.nlm.nih.gov/Blast.cgi. The FASTA package is available from the University of Virginia at https://fasta-.bioch.virginia.edu/fasta_www2/fasta_list2.shtml and the European Bioinformatics Institute (EMBL-EBI) at https://www.ebi.ac.uk/Tools/sss/fasta/.

In addition, in some embodiments where the tag sequences and primers used are well known, it may be inferred that the sequence amplified by the primers used are the tag sequences without sequencing those nucleotide sequences for confirmation. In embodiments where genetic variation has been introduced into the bacterial or microbial genome, however, it will likely be necessary to sequence the nucleotide sequences amplified by the primers being used to confirm that sequence being amplified is the tag sequence.

To identify unique DNA sequences, the microorganism genomes to be used as tags will be downloaded from GenBank or similar databases, or, if unavailable, sequenced using NGS sequencing and assembled. The resulting genome sequences may then be aligned with various methods, including but not limited to BLAST https://blast.ncbi.nlm.nih.gov/Blast.cgi, Mummer (https://mummer4.github.io/), Muscle (https://pubmed.ncbi.nlm.nih.gov/15034147/), and dot plot algorithms. The alignments will be parsed to identify unique regions (sections of the alignments that have a sequence depth of 1). These potentially unique sequences are blasted against various databases to ascertain their global uniqueness and their aptness for certain applications. Primers for these unique sequences may be designed using tools such as Primer3 (https://primer3.org/), and the strain identifiers, sequence positions, nucleotide sequences, primers, expected PCR product sizes, etc. may be stored in a database for use as tags.

From these unique sequence numerous target sequences can be identified for potential use as a tag. While the length of a target sequence is not per se limited, it should be long enough as to be sufficiently distinctive to serve as a tag, but not so long as to make later sequencing more difficult or unduly limit the number of unique tags that can be developed from a particular type of bacteria, yeast, or any other microorganism.

In various embodiments, these target sequences will be from 10 base pairs to several thousand base pairs in length. In one or more embodiments, the target sequences will be from about 10 base pairs to about 5,000 base pairs in length. In some embodiments, the target sequences will be from about 20 base pairs to about 4,000 base pairs, in other embodiments, from about 50 base pairs to about 4,000, base pairs in other embodiments, from about 100 base pairs to about 4,000 base pairs, in other embodiments, from about 500 base pairs to about 4,000 base pairs, in other embodiments, from about 1,000 base pairs to about 4,000 base pairs, in other embodiments, from about 2,000 base pairs to about 4,000 base pairs, in other embodiments, from about 20 base pairs to about 3,000 base pairs, in other embodiments, from about 20 base pairs to about 2,000 base pairs, in other embodiments, from about 20 base pairs to about 1,000 base pairs, in other embodiments, from about 20 base pairs to about 500 base pairs, in other embodiments, from about 20 base pairs to about 400 base pairs, in other embodiments, from about 20 base pairs to about 300 base pairs, and in other embodiments, from about 20 base pairs to about 200 base pairs in length. In one or more embodiments, the target sequences will be from about 100 base pairs to about 1,000 base pairs in length. In some other embodiments, the target sequences will be from about 1500 base pairs to about 4,000 base pairs in length.

In some embodiments, the target nucleotide sequence will comprise all or substantially all of said genomic DNA. A target sequence will be understood to comprise substantially all of the genomic DNA if it contains 50% or more of the genomic DNA. In some embodiments, the various target sequences will typically comprise from about 0.001% to about 10% of said genomic DNA.

Once one or more target sequences have been developed, they are compared to the DNA present in the product or item to be tagged and potential target sequences present in the item to be tagged are excluded for use as a tag with that product. In various embodiments, this may be done in two steps: (1) using a bioinformatics step based on the composition of the product (for example, if the product is wheat based, it will be blasted against all available wheat genomes, and matches against the wheat genome will be discarded for this application, and (2), the primers are verified to yield a negative result on the matrix alone (without the tag). One or more target sequence may be selected to serve as a tag for that item.

In some embodiments, the tags may be selected and created as follows. As set forth above, the tags consist of a suitable microbe, in which a specific, unique DNA segment, or polymorphism through induced natural variation, has been identified, which can be specifically amplified using PCR. In one embodiment, the tags are created in silico from readily available sequencing information, either from reference databases such as Genbank, or from sequence produced for the strains with induced variation. In other embodiments, the sequencing data will have to be produced with methods such as next generation sequencing approaches, for specific, desirable microbes to be used as tags. A thorough quality control procedure, based on in vitro experiments, based on technologies such as PCR and sequencing, at the end of the design phase, is required to guarantee proper functioning of a tag in the matrices it will be used with. The matrix here is defined as the product to be tagged, which could contain other microbes or DNA sources that interfere with the assay.

To design the tags, the full genome sequences of suitable microbes, such as those listed in Table 1, are aligned to each other, using bioinformatics tools such as MUMMER (https://github.com/mummer4/mummer), different approaches involving the BLAST algorithm (https://blast.ncbi.nlm.nih.gov/Blast.cgi) such as reciprocal BLAST, alignment software such as bowtie2 (https://bowtie-bio-.sourceforge.net/bowtie2/index.shtml), and multiple alignment software such as Muscle (https://pubmed.ncbi.nlm-.nih.gov/15034147/) or ClustalW (https://pubmed.ncbi.nlm.nih.gov/17846036/), are used to identify unique sequences in a group of microbes. In one embodiment, the all the genome sequences of a group of microbes to be used as tags are split up into suitably sized n-mers (n ranging typically from 8 to 32), and the n-mers aligned to a candidate genome. Sequences in the candidate that also occur in the other genomes will have an alignment depth of greater than zero, whereas unique regions in the candidate genome will have a coverage of 0 n-mers. These latter regions will serve as candidate regions for specific PCR amplification. The PCR primers can be automatically designed using tools such as Primer3, which takes a candidate sequence, the desired amplified length, and the desired melting temperatures as inputs, and outputs suitable PCR primers, optimized for melting temperature and low secondary structure.

The quality control phase tests the tags vis-a-vis other tags, to test tag specificity, as well as the product to be tagged as a negative control, to ensure that no bands are amplified without the addition of a tag.

Once the target nucleotide sequence or sequences have been selected to serve as a tag, the target nucleotide sequence or sequences and identifying information about the product being tagged are recorded and saved for later retrieval. The identifying information about the product being tagged is not particularly limited and will vary depending upon the particular item and/or product being tagged and the particular application for which the invention is being used. Almost any relevant information regarding the tag or the product can be stored in a database for later retrieval. In some embodiments, the target nucleotide sequence or sequences selected to serve as a tag and the identity of the item to be tagged are saved and linked in non-transitory computer memory in a local or cloud-based computer database or spreadsheet. In various embodiments, identifying information saved in the database may include, without limitation, such things as an assigned unique identifier number (UID), the name and location of the producer of manufacturer, shipment information (origin, itinerary, destination information), shipment metadata (temperature, packaging, etc.), lot numbers, production date, expiry date, source, the name and location of distributor or distributors, production methods, the name and location of the licensee or licensees, critical quality parameters, critical process parameters, manufacture or growth conditions, geographical origin/provenance, climate information, environmental information, the use of pesticides and other agricultural practices, other grower metadata, the allergen-free status, the halal/kosher/organic status, the GMO-free status, the fair trade status, the regulatory approval status (e.g., USDA or FDA approval status), other customer information, and combinations thereof, as set forth above. In various embodiments, the database would be expected to include the name and relevant identifying information for the bacteria used to form the tag (e.g., the corresponding GenBank accession numbers for the sequenced genome, the American Type Culture Collection (ATTC) numbers and other popular identifiers and names of the strain), in addition to the specific target sequence, sequence coordinates in the reference genome, or sequences to serve as the tag, but the database may also include additional useful information such the corresponding primer sequences for PCR, PCR protocols, PCR conditions, and expected PCR product sizes. As will be apparent, the target nucleotide sequence or sequences selected to serve as a tag and information regarding the identity of the item to be tagged will be saved and linked together in the database.

In one or more embodiments, a database of tags may be implemented in a relational database system, no-SQL database, blockchain, or other type of database system, and contain the strain identifier, primer sequences, genome reference sequences, genomic coordinates of selected tags, meta information on uniqueness of the tags, protocols and assay conditions, expected PCR product sizes, and other meta data. It may also link to a database of tagged samples, including, without limitation, such things as an assigned unique identifier number (UID), the name and location of the producer of manufacturer, shipment information (origin, itinerary, destination information), shipment metadata (temperature, packaging, etc.), lot numbers, production date, expiry date, source, the name and location of distributor or distributors, production methods, the name and location of the licensee or licensees, critical quality parameters, critical process parameters, manufacture or growth conditions, geographical origin/provenance, climate information, environmental information, the use of pesticides and other agricultural practices, other grower metadata, the allergen-free status, the halal/kosher/organic status, the GMO-free status, the fair trade status, the regulatory approval status (e.g., USDA or FDA approval status), other customer information, and combinations thereof. lot codes, origin of samples, manufacture or growth conditions of the sample, shipment information (origin, itinerary, destination information), shipment metadata (temperature, packaging, etc.), other sample metadata, and customer information. The database may also track assay results before, during and after shipment, that aid in determining product authenticity and integrity.

In some of these embodiments, the computer database and/or database of tags is stored on a blockchain. The blockchain provides a tamper proof, cryptographically signed data structure that provides a high degree of data integrity, security, and trust.

In various embodiments, the microorganisms containing the target nucleotide sequence or sequences selected to serve as a tag may be cultured by conventional means to ensure that there are enough cells to serve as a tag. Culturing of bacteria and other microorganisms is well known in the art and one of ordinary skill in the art will be able to select a suitable method and medium for culturing the bacterial or other microorganisms containing the target nucleotide sequence or sequences selected to serve as tags without undue experimentation. The number of tags and, therefore, the number of cells necessary will depend upon the specific application. About 100 copies of the bacterial tags are minimally required in a given sample to allow detection, but this number may depend on the exact composition and volume (i.e., the tag concentration) of the matrix, and has to be established for each matrix and tag. One of ordinary skill in the art will be able to determine number of tags and, therefore, the number of cells necessary for a particular application, without undue experimentation. In some embodiments, the probiotic microorganisms containing the target nucleotide sequence or sequences selected to serve as a tag may be grown in a suitable medium to a desired optical density at a wavelength 600 nm ($OD_{600}$) and either used at that concentration or diluted to a desired concentration. In some of these embodiments, the probiotic microorganisms containing the target nucleotide sequence or sequences selected to serve as a tag is either grown or diluted to an $OD_{600}$ of 0.1, which is then diluted to a volume that will provide a desired tag concentration in the product or material being tagged.

As set forth above and shown in the step 2 of FIG. 1, the microorganisms containing the target nucleotide sequence or sequences are killed to form the tags. The cells are not simply metabolically inactive as described in US Patent Application Publication Number 2014/0356858. A cell is considered "killed" when it cannot be reactivated, revived or regrown. The microorganisms are preferably killed in a manner that leaves the cell wall of the microorganism substantially intact to further protect the DNA serving as the tag, but this need not be the case. The cell wall will be understood to be "substantially intact" if 50% or more of the cell wall remains in place after the cell has been killed. In some embodiments, the killing of the cells may be confirmed by placing some of the "killed" cells in a growth medium. As will be apparent, if the cells have been completely killed, there will be no growth of the bacteria cells in the growth medium at optimal temperature and oxygenation conditions for said microorganism after 96 hours. (See, e.g., FIG. 5)

In some embodiments, the cells are killed using methods commonly used with foods and known to be safe for use with foods. In various embodiments, these will be methods classified by governmental agencies responsible for food safety as generally regarded as safe ("GRAS"). Moreover, the methods for killing the cells may vary to some degree with the specific strain of probiotic microorganism being used. Some small degree of experimentation may be required to arrive at the best method for a particular organism and application.

In one or more embodiments, the microorganisms are killed by incubation at a temperature of from about 63° C. to about 138° C. for from about 0.01 to 30 min. The specific temperature and time required to kill the cells may vary depending upon the microorganism used. In some of these embodiments, the microorganisms are killed by incubation at 70° C. for 10 minutes, 80° C. for 5 minutes, or 95° C. for 2 minutes. In one or more of these embodiments, the cells may be killed by incubation for 10 minutes at 90° C. In one or more of these embodiments, the cells may be killed by incubation for about 20 minutes at 80° C. In some other embodiments, the cells may be killed by incubation for about 10 minutes at 95° C. The kill protocol will be tested on each strain to ensure that it is effective on the given strain. One of ordinary skill in the art will be able to determine an incubation time and temperature time sufficient to kill specific strains of microorganisms without undue experimentation.

In some embodiments, the probiotic bacteria or other microorganisms used are killed by irradiation. The microorganisms are irradiated at an energy and for a period of time sufficient to kill the cells, such that growth in in vitro culture is undetectable using standard methods. In some embodiments, the irradiation used to kill the microorganisms is ionizing radiation, such as Gamma radiation, as set forth in U.S. Application Publication No. 2005/0180962, the disclosure of which is incorporated herein by reference in its entirety. In one or more of these embodiments, for example, the bacteria are irradiated using gamma irradiation in an amount of from about 5 kiloGray (kGy) to about 50 kGy, from about 10 kGy to about 20 kGy, from about 20 kGy to about 40 kGy, or from about 25 kGy to about 35 kGy. Bacteria are irradiated for a period of time from about 15 seconds to about 48 hours, e.g., from about 15 seconds to about 1 minute, from about 1 minute to about 15 minutes, from about 15 minutes to about 30 minutes, from about 60 minutes to about 90 minutes, from about 90 minutes to about 2 hours, from about 2 hours to about 4 hours, from about 4 hours to about 8 hours, from about 8 hours to about 12 hours, from about 12 hours to about 16 hours, from about 16 hours to about 24 hours, from about 24 hours to about 36 hours, or from about 36 hours to about 48 hours. The total amount of irradiation and the duration of irradiation can be adjusted, depending on various factors, e.g., the number of bacteria being irradiated. It is believed that killing the cells by ionizing radiation, as set forth above, maintains the structural integrity of the cell (e.g., of the cell wall and/or cytosolic components) in to a degree not seen with the heat-based methods.

In some other embodiments, the step of killing comprises irradiation the microorganisms with x-rays at an absorbed dose of 20-40 kilogray from a Co (60) source.

In some other embodiments, the step of killing comprises sonication of the microorganisms at frequencies between 20 kHz and 1 GHz for from about 30 seconds to about 180 seconds. In some embodiments, the step of killing comprises sonication of the microorganisms at frequencies from about 50 kHz to about 1 GHz, in other embodiments, from about 100 kHz and 1 GHz, in other embodiments, from about 200 kHz and 1 GHz, in other embodiments, from about 300 kHz and 1 GHz, in other embodiments, from about 500 kHz and 1 GHz, in other embodiments, from about 600 kHz and 1 GHz, in other embodiments, from about 800 kHz and 1 GHz, in other embodiments, from about 50 kHz and 800 kHz, in other embodiments, from about 50 kHz and 700 kHz, in other embodiments, from about 50 kHz and 600 kHz, in other embodiments, from about 50 kHz and 500 kHz, in other embodiments, from about 50 kHz and 400 kHz, and in other embodiments, from about 50 kHz and 200 kHz. In some embodiments, the step of killing comprises sonication of the microorganisms for from about 45 seconds to about 180 seconds, in other embodiments, from about 60 seconds to about 180 seconds, in other embodiments, from about 75 seconds to about 180 seconds, in other embodiments, from about 90 seconds to about 180 seconds, in other embodiments, from about 120 seconds to about 180 seconds, in other embodiments, from about 145 seconds to about 180 seconds, in other embodiments, from about 30 seconds to about 145 seconds, in other embodiments, from about 30 seconds to about 120 seconds, in other embodiments, from about 30 seconds to about 90 seconds, in other embodiments, from about 30 seconds to about 60 seconds, and in other embodiments, from about 30 seconds to about 45 seconds.

As will be apparent, microorganisms that cannot be killed using the methods and protocols set forth herein, should not be used as tags, particularly for food-grade applications.

Once the cells have been killed to form the tags of the present invention, they are collected. In some embodiments, the tags may be dried to a powder using conventional DNA safe methods. In some embodiments, the tags may be dried to a powder by lyophilization. In some other embodiments, the tags may be suspended in a suitable liquid such as TE or PBS buffer.

In various embodiments, a small quantity of the tags is added to the item or product being tagged as shown in step 3 of FIG. 1. As set forth above, the tags are added to the item or product in an amount that does not change or in any way alter the appearance or properties of the item or product tagged. In one or more embodiments, the tags will be added at a concentration of from about 0.001 to about 100 ppm, but the invention is not to be so limited and the tag concentration may be outside this range depending upon the nature of the tag and the product in which it will be used. In some embodiments, the tags will be added at a concentration of from about 0.05 to about 10 ppm. In some embodiments, the tags will be added at a concentration of from about 0.1 to about 5 ppm, in other embodiments, from about 0.5 ppm to about 5 ppm, in other embodiments, from about 1 ppm to about 5 ppm, in other embodiments, from about 2 ppm to about 5 ppm, in other embodiments, from about 3 ppm to about 5 ppm, in other embodiments, from about 0.05 ppm to about 4 ppm, in other embodiments, from about 0.05 ppm to about 3 ppm, in other embodiments, from about 0.05 ppm to about 2 ppm, and in other embodiments, from about 0.05 ppm to about 1 ppm. In some embodiments, the tags will be added at a concentration of about 1 ppm. In some other embodiments, the tags will be added at a concentration of about 10 ppm. The number of tags necessary will depend upon the item tagged and the quantity of other DNA in the item making recovery of the tags more difficult. A PCR step will be necessary in most cases to amplify the specific tag DNA to identify PCR products of the correct size or to obtain sufficient material for sequencing.

As set forth above, the item or product will be capable of receiving and containing the microbial tag of the present invention, but is not otherwise limited. As will be apparent, however, to be able to "contain" tags, the item or product should not be so acidic or caustic that it breaks down the tags.

The tags may be applied to the item or product in any suitable manner. Preferably, however, the tag will be mixed into and distributed throughout the item being tagged. In this way, the tags cannot easily be removed and are more likely be present in significant numbers in the sample when it is later tested. In some embodiments, the item being tagged will comprise a consumer product or ingredient to a consumer product in powder form (i.e., flour, ground pepper, snack seasonings, etc.), a consumer product or ingredient to a consumer product in liquid (i.e. mineral water, alcoholic beverages, perfumes, oils, plant extracts, plant distillates, etc.), a consumer product or ingredient to a consumer product in gel (i.e. yogurt, face creams, cosmetics, etc.) and/or in a paste (i.e., ground beef, miso, bean paste, etc.) and a small amount of the tags can simply be mixed into the item or product. In some other embodiments, the tags may be used in fuel, oil, and lubricants and similar materials. In some embodiments, raw extracts, such as high value flavor extracts, such as vanilla extracts, can be tagged and tracked.

As will also be apparent, where the product or material to be tagged is dry (i.e., a dry powder like ground pepper or cinnamon), it is preferable that the tags be added as a dry powder, since addition of a small amount of liquid containing the tag to a dry ingredient will effectively prevent proper mixing of the tag throughout the product. As set forth above, to the extent possible, the tags should be thoroughly mixed into the product to ensure that they cannot easily be removed and are more likely be present in significant numbers in the sample (or portion thereof) later tested. In some embodiments, dry tags can be added to liquid or gel products, provided that they can be sufficiently blended or mixed into the product being tagged. In some embodiments, the tags will be dried by lyophilization (although other known methods are also possible) and added to the product to be tagged as a fine powder.

In some embodiments, the bacteria or other microorganism that will form the tags may be provided suspended in a suitable liquid medium or may be grown in a suitable medium to a desired concentration, as is known in the art and discussed above. As set forth above, in some these embodiments, the liquid bacteria or microorganism culture or suspension that will form the tags are concentrated in a centrifuge and then lyophilized to form a dry powder as is known in the art. In some embodiments, a quantity of the liquid bacteria or microorganism culture or suspension having a known concentration of bacteria or other microorganism cells that will form the tags may be concentrated in a centrifuge, lyophilized to form a dry powder, and an amount (weight) of dry powder expected to produce a desired number of tags (based upon the concentration of cells in the liquid media) is removed and added to the material being tagged. In some other embodiments, the liquid bacteria or microorganism culture or suspension is divided or diluted to form one or more samples having a desired number of tags based upon the known cell concentration of liquid bacteria or microorganism culture or suspension. Each of these samples is then concentrated by centrifuge, lyophilized, and added to the product or material to be tagged.

In some other embodiments, however, the item to be tagged is a solid and it is not possible to simply mix the tags into the product. In these embodiments, the tags are preferably added to a component of the item prior to its formation into the solid item to be tagged. For example, tags could be added to chocolate prior to its hardening While not preferred, the tags can also be applied to the surface of a solid item or product by any conventional means, including, but not limited to dip coating, spin coating, spray coating or brush (or roller) coating. In these embodiments, the tags will be mixed with a coating material, such as wax or varnish, and applied to all or just a portion of the object. In these embodiments, care must be taken to ensure that the coating (and with it the tags) is not removed to disguise the product or just wear off the portion of the product sampled to find the tags. In these embodiments, the database must also to record where on the item the tags have been applied, so that the correct portion of the item is sampled.

In pharmaceutical applications, the tags can simply be added into liquid preparations for oral administration or, alternatively, lyophilized, mixed with dry ingredients and formed into capsules or tablets. In these embodiments, the tags would preferably be formed from food grade probiotic bacteria, as described above.

In agricultural applications, the tags may be applied to homogeneous batches of bulk commodities through continuous dosing, addition in processing step such as milling, distillation or extraction. In various embodiments, the tags may be added to alcoholic beverages after fermentation. In some embodiments, the tags may be added to high fructose corn syrup after the enzymatic conversion step. In other embodiments, the tags may be added to such things as commodity grains, fruit juices, flavor extracts, or milk-based products.

To later confirm the identity of a tagged product, the DNA is extracted from the product using conventional methods as shown in step 4 of FIG. 1. In some embodiments, the DNA may be extracted using the techniques set forth in Sepp, et al., "Rapid techniques for DNA extraction from routinely processed archival tissue for use in PCR" *J Clin Pathol.* 1994 April; 47 (4): 318-323 (doi: 10.1136/jcp.47.4.318), the disclosure of which is incorporated herein by reference in its entirety. In one or more embodiments, the step of extracting the DNA from tags in the product may be performed by subjecting a sample of the item to ethanol precipitation and dissolution in Tris-EDTA (TE) or similar buffer. In some other embodiments, the step of extracting the DNA from tags in the product may be performed by using a spin column (for example, Qiagen, Hilden, Germany) and eluting the DNA in elution buffer. Suitable elution buffers may include, without limitation, TE or PBS buffer, or a combination thereof.

In some other embodiments, the step of extracting the DNA from tags in the product may be performed by boiling or sonication of the sample. In some embodiments, the step of extracting the DNA from tags in the product may be performed by boiling the sample for from about 1 minute to about 30 minutes. In some of these embodiments, the step of extracting the DNA from tags in the product may be performed by boiling the sample for 20 minutes. In some other embodiments, the step of extracting the DNA from tags in the product may be performed by sonication of the sample for from about 15 seconds to about 90 seconds. In some of these embodiments, the step of extracting the DNA from tags in the product may be performed by sonication of the sample for about 10 seconds. In some of these embodiments, the sample is sonicated on ice using three 10-second bursts at high intensity with a 30 second cool down on the ice between bursts. In embodiments, where the concentration of tags in the sample is high, the sample may be used without the extraction step.

Once the DNA has been extracted, primers for the target nucleotide sequences corresponding to the tag or tags being sought are added to the extracted DNA and the target nucleotide sequence amplified by PCR. One of ordinary skill in the art will be able to create suitable primers for the target nucleotide sequences without undue experimentation. In some embodiments, these primers may be formed using known solid phase oligonucleotide synthesis methods. Some primers and PCR conditions for amplification target nucleotide sequences are shown in Table 1, below.

TABLE 1

Primers and PCR conditions for a selection of appropriate microorganisms

| Target species | Primers | PCR protocol | No of cycles | Product length | References* |
|---|---|---|---|---|---|
| Bifido-bacterium animalis subsp. lactis | BflactF: 5'-CCCTTTCCACGGGTCCC-3' (SEQ ID No. 1) BflactR: 5'-AAGGGAAACCGTGTCTCCAC-3' (SEQ ID No. 2) | 95° C./3 min 95° C./15 s 62° C./20 s 72° C./30 s 72° C./5 min | 1 30 1 | 194 bp | Malinen et al., 2003 |
| Bifido-bacterium bifidum | BiBIF-1: 5'-CCACATGATCGCATGTGATTG-3' (SEQ ID No. 3) BiBIF-2: 5'-CCGAAGGCTTGCTCCCAAA-3' (SEQ ID No. 4) | 95° C./3 min 95° C./30 s 55° C./30 s 72° C./30 s 72° C./5 min | 1 30 1 | 278 bp | Matsuki et al., 1999 |
| Bifido-bacterium longum | F: 5'-CAGTTGATCGCATGGTCTT-3' (SEQ ID No. 5) R: 5'-TACCCGTCGAAGCCAC-3' (SEQ ID No. 6) | 95° C./3 min 95° C./15 s 60° C./20 s 72° C./30 s 72° C./5 min | 1 35 1 | 106 bp | Malinen et al., 2003 |
| Bifido-bacterium longum subsp. infantis | BiINF-1: 5'-TTCCAGTTGATCGCATGGTC-3' (SEQ ID No. 7) BiINF-2: 5'-GGAAACCCCATCTCTGGGAT-3' (SEQ ID No. 8) | 95° C./3 min 95° C./30 s 55° C./30 s 72° C./30 s 72° C./5 min | 1 35 1 | 828 bp | Matsuki et al., 1999 |
| Entero-coccus faecium | ddl F1: 5'-GCAAGGCTTCTTAGAGA-3' (SEQ ID No. 9) ddl F2: 5'-CATCGTGTAAGCTAACTTC-3' (SEQ ID No. 10) | 95° C./3 min 95° C./30 s 55° C./30 s 72° C./30 s 72° C./5 min | 1 30 1 | 550 bp | Dutka-Malen et al., 1995 |
| Lacto-bacillus acido-philus | LacI: 5'-AGCTGAACCAACAGATTCAC-3' (SEQ ID No. 11) LacII: 5'-ACTACCAGGGTATCTAATCC-3' (SEQ ID No. 12) | 95° C./3 min 95° C./30 s 62° C./30 s 72° C./30 s 72° C./5 min | 1 30 1 | 759 bp | Walter et al., 2000 |
| Lactocasei-bacillus casei | Cas1: 5'-TGCACTGAGATTCGACTTAA-3' (SEQ ID No. 13) Y2: 5'-CCCACTGCTGCCTCCCGTAGGAGT-3' (SEQ ID No. 14) | 95° C./3 min 95° C./30 s 62° C./30 s 72° C./30 s 72° C./5 min | 1 30 5 | ~300 bp | Ward et al., 1999 |
| Lb. delbrueckii subsp. bulgaricus | LB1: 5'-AAAAATGAAGTTGTTTAAAGTAGGTA-3' (SEQ ID No. 15) LLB1: 5'-AAGTCTGTCCTCTGGCTGG-3' (SEQ ID No. 16) | 95° C./3 min 95° C./30 s 58° C./30 s 72° C./30 s 72° C./5 min | 1 30 1 | 1065 bp | Torriani et al., 1999 |
| Lactocasei-bacillus paracasei | Para1: 5'-CACCGAGATTCAACATGG-3' (SEQ ID No. 17) Y2: 5'-CCCACTGCTGCCTCCCGTAGGAGT-3' (SEQ ID No. 18) | 95° C./3 min 95° C./30 s 55° C./30 s 72° C./30 s 72° C./5 min | 1 30 1 | 290 bp | Ward et al., 1999 |
| Lactiplanti-bacillus plantarum | Plant 1: 5'-ATCATGATTTACATTTGAGTG-3' (SEQ ID No. 19) LOWLAC: 5'-CGACGACCATGAACCACCTGT-3' (SEQ ID No. 20) | 95° C./3 min 95° C./30 s 58° C./30 s 72° C./30 s 72° C/5 min | 1 30 1 | 996 bp | Chagnaud in sod., 2001 |

TABLE 1-continued

| Target species | Primers | PCR protocol | No of cycles | Product length | References* |
|---|---|---|---|---|---|
| *Limosilacto-bacillus reuteri* | Lfpr: 5'-GCCGCCTAAGGTGGGACAGAT-3' (SEQ ID No. 21) Reu: 5'-AACACTCAAGGATTGTCTGA-3' (SEQ ID No. 22) | 95° C./2 min 95° C./30 s 55° C./30 s 72° C./30 s 72° C./5 min | 1 30 1 | 200-300 bp | Walter et al., 2000 |
| *Lactocasei-bacillus rhamnosus* | PrI: 5'-CAGACTGAAAGTCTGACGG-3' (SEQ ID No. 23) RhaII: 5'-GCGATGCGAATTTCTATTATT-3' (SEQ ID No. 24) | 95° C./3 min 95° C./30 s 58° C./30 s 72° C./30 s 72° C./5 min | 1 30 1 | 186 bp | Walter et al., 2000 |
| *Ligilacto-bacillus salivarius* | Sal1: 5'-ATTCACTCGTAAGAAGT-3' (SEQ ID No. 25) LOWLAC: 5'-CGACGACCATGAACCACCTGT-3' (SEQ ID No. 26) | 95° C./3 min 95° C./30 s 50° C./30 s 72° C./1 min 72° C./5 min | 1 30 1 | 993 bp | Chagnaud in sod., 2001 |
| *Lactococcus lactis* | 27f: 5'-AGAGTTTGATCMTGGCTCAG-3' (SEQ ID No. 27) LIa: 5'-CAGTCGGTACAAGTACCAAC-3' (SEQ ID No. 28) | 95° C./2 min 95° C./30 s 55° C./30 s 72° C./30 s 72° C./5 min | 1 30 1 | 87 bp | Barakat et al., 2000 |
| *Strepto-coccus salivarius subsp. thermophilus* | ThI: 5'-ACGGAATGTACTTGAGTTTC-3' (SEQ ID No. 29) ThII: 5'-TTTGGCCTTTCGACCTAAC-3' (SEQ ID No. 30) | 95° C./3 min 95° C./30 s 58° C./30 s 72° C./30 s 72° C./5 min | 1 30 1 | 205-304 bp | Tilsala-Timisjärvi in Alatossava, 1997 |

*The references in Table 1 are all incorporated herein by reference in their entirety.

In some embodiments, for example, the tag may be a unique portion of the genome of *Bifidobacterium longum* (IM 937) having the sequence acgeggegttgctccatca-gacttgcgtccatt gtggaagattccctactgctgcctcccgtag-gagtttgggccgtgtctcagtcccaatgtggccgatcaacctctcagttcggc-tacgtatcat cgccttggtgagccattacctcaccaactagctaatacgccgegggtccatc-caaaagcgatagcttacgccatctttcagccaagaaccat gcggttcttggatc-tatgcggtattagcatctgtttccaaatgttatcccc (SEQ. ID. No. 31) and is amplified by the primers identified as SEQ. ID NOS. 5 and 6.

As shown in step 5 of FIG. 1, the amplified DNA is then sequenced and compared to target nucleotide sequences stored in the database to determine whether the tag was present in the item or product. The amplified DNA sequence may be sequenced using any suitable method, including but not limited to Sanger sequencing or targeted next generation sequencing (tNGS) techniques, or using deep NGS sequencing of the entire sample. The amplified DNA sequence is then compared to the sequences saved in the database as tags, using BLAST or similar techniques. PCR amplification sometimes introduces errors in the PCR product. To avoid such errors, PCR amplifications will be done in replicates, and all the products sequenced separately. As errors are assumed to be introduced randomly, the real sequence should be easily recovered from the replicates. Near perfect sequence (>99.9%) matches would be expected for a positive result.

In other embodiments, the tags will be detected using specially crafted microarrays, gene chips, and related technologies. To detect tags using a microarray, a microarray needs to be constructed containing the appropriate DNA sequences to detect all the tags in use. There are numerous microarray and related technologies in existence that those skilled in the art can design and employ for the detection step.

In some other embodiments, the PCR amplification step may be omitted. In these embodiments, all of the DNA in the product or sample being tested is sequenced using NGS techniques and the resulting sequences are compared to the target nucleotide sequence saved in the database using BLAST or a comparable technique.

EXAMPLES

The following examples are offered to more fully illustrate the invention but are not to be construed as limiting the scope thereof. Further, while some of the examples may include conclusions about the way the invention may function, the inventors do not intend to be bound by those conclusions but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Materials and Methods

The bacterial library was stored as glycerol stocks at −80C. Bacterial strains were grown in suitable media: MRS for lactobacilli and bifidobacteria and M17 (Sigma, St Louis, MI) for lactococci and streptococci. Bacterial cultures (10 ml) were centrifuged at 3300 g. Supernatant was removed and the pellet was resuspended in 1 ml of water.

Unless otherwise indicated, species-specific PCR Reaction mixes for species/subspecies (see, Table, 1) specific PCR (20 μL) contained MyTaq™ buffer (Meridian Biosciences, Cincinnati, OH) with 3-7 mM MgCl₂ and 0.1 mM deoxynucleoside triphosphate (dNTP), 0.5 μM oligonucleotide primers, 0.1 μl MyTaq™ Red DNA polymerase (Meridian Biosciences, Cincinnati, OH) and 2 μL DNA. Unless otherwise indicated, the PCR reactions were performed using the specific primers and reaction conditions for each strain as described in Table 1 above. Unless otherwise indicated, the bacteria used to form tags was killed by heating at 95° C. for 10 min.

Example 1

DNA Extraction
(General Procedure)

30 mg/μl of a DNA containing sample was transferred to a microtube and resuspended in 0.4 mL of TE buffer containing 4 mg of lysozyme (Sigma Chemical, St. Louis, USA) and 4 μL of mutanolysine (2500 U/mL) (Sigma Chemical, St. Louis, USA). After 1 h incubation at 37° C., DNA was isolated using Maxwell 16 Tissue DNA Purification Kit (Promega, Madison, USA) according to the manufacturer's protocols.

Example 2

Detection

To detect the tags, the sample containing the tags was heated to 95° C. for 10 min and then sonicated for 30-300 seconds to free the bacterial DNA from the remains of the cell. The extracted DNA was then purified using the Promega DNA purification kit (Promega Corporation, Madison, WI). The real time PCR was performed for each strain using the primers and conditions set forth above in Table 1. The PCR products were then sequenced using Sanger or NGS sequencing (Illumina) to confirm the presence of the tags.

Example 3

UV-Induced Nucleotide Variation for Tags

To further demonstrate to induce additional nucleotide variability into the genome of the microorganisms to be used in the preparation of tags according to the present invention, a bacterium for use in forming these tags was subjected to UV-induced natural sequence variation and analyzed.
1. Induction of Natural Sequence Variation and DNA Isolation Bacterial strain Lacticaseibacillus *paracasei* IM 932 was inoculated (1% v/v) in 10 ml of MRS broth and incubated at 37° C. for 72 hours. Afterwards, 100 μl of strain culture was spread on the surface of MRS agar. Agar plates were exposed to UV light for 0, 3, 6, 9, 12, 15, 30, 45 and 60 seconds. Plates were incubated at 37° C. for 72 hours in anacrobic conditions. From the plate exposed to UV light for 15 s where only a few colonies grew (comparing to control plate without UV exposure), five colonies were selected for further analyses.

Selected colonies were inoculated in 10 ml of MRS broth and incubated at 37° C. for 72 hours. Bacterial cultures (1 ml) were centrifuged at 12000 g for 3 minutes. Supernatant was removed and pellet was resuspended in 0.4 mL of TE buffer containing 4 mg of lysozyme (Sigma Chemical. St. Louis, USA) and 4 μL of mutanolysine (2500 U/mL) (Sigma Chemical, St. Louis, USA) was added to the samples. After 2 h incubation at 37° C., DNA was isolated using Maxwell 16 Tissue DNA Purification Kit (Promega, Madison, USA) according to the manufacturer's protocols.
2. Sequencing and Bioinformatic Analysis of the Mutants Sequencing and bioinformatic analyses were performed by the National Laboratory of Health, Environment and Food in Ljubliana, Croatia. The genomic DNA was isolated and the libraries were prepared for sequencing with the NEBNext Ultra II FS DNA library Prep Kit (NEB). The protocol is available at https://www.neb.com/protocols/2017/10/25/protocol-for-fs-dna-library-prep-kit-e7805-e6177-with-inputs-less-than-or-equal-to-100-ng.

The DNA was sequenced in a NexSeq P2 sequencer (Illumina, San Diego), using a paired end sequencing method, sequencing two reads from both ends to a length of 150 base pairs.

The resulting sequence files were then quality checked and filtered using the generally available open source tools such as Trimmomatic (available at http://www.usadel-lab.org/cms/?page=trimmomatic), Fast QC (available at https://www.bioinformatics.babraham.ac.uk/projects/fastqc/), Kraken 2 (available at https://ccb.jhu.edu/software/kraken2/), KronaTools (available at https https://ccb.jhu.edu/software/kraken2/), and Spades (available at https https://home.cc.umanitoba.ca/~psgendb/doc/spades/manual.html). The cleaned reads were aligned to the reference genome available from Genbank (Lacticaseibacillus *paracasei* subsp. *paracasei* isolate IM932 genome assembly, accession #: CAKMAL010000001.1) using the open source tools Bowtie and the Samtools suite.

The mutation analysis was performed with the BioNumerics program (bioMerieux, https://www.bionumerics.com/). To detect Single Nucleotide polymorphisms (SNPs) the following parameters where used: SNP coverage: at least 5×, of which at least 1× with Forward and 1× with Reverse reading; sites with N and non-A, -T, -C and -G bases were excluded from the analysis.

Results

An overview of the sequencing and quality control (QC) analyzes of the genomic sequences are given in Table 2, below. An overview of the mutations in the sequenced genomes (MUT 1-MUT 5), compared to the reference genome (IM 932), is given in Appendix 1.

TABLE 2

| | | | | | | | | |
|---|---|---|---|---|---|---|---|---|
| | Overview of sequenced genomes and analysis (QC). | | | | | | | |
| ID | Read counts (after trimming) | Genome size - Assembled (Mb) | N50 | # of contigs | # of contigs >=1000 bases | Median coverage | GC-content | % Reference genome covered |
| MUT1 | 1913664 | 3.0 | 97227 | 84 | 73 | L85.0 | 46.3 | 94.0 |
| MUT2 | 1736624 | 3.0 | 96869 | 81 | 72 | L68.0 | 46.3 | 94.1 |
| MUT3 | 1523718 | 3.0 | 96863 | 81 | 72 | L47.9 | 46.3 | 94.8 |

TABLE 2-continued

| | | | | | | | | |
|---|---|---|---|---|---|---|---|---|
| | | | | | Overview of sequenced genomes and analysis (QC). | | | |
| ID | Read counts (after trimming) | Genome size - Assembled (Mb) | N50 | # of contigs | # of contigs >=1000 bases | Median coverage | GC-content | % Reference genome covered |
| MUT4 | 1942851 | 3.0 | 96869 | 86 | 73 | L88.2 | 46.3 | 94.2 |
| MUT5 | 1438286 | 3.0 | 89932 | 85 | 74 | L39.2 | 46.3 | 94.0 |

Example 4

Generation of Additional Sequence Diversity by ethyl meth-anesulfonate (EMS)

(Prophetic)

Overnight cultures of potential tag strains produced by UV treatment were washed three times with sterile saline solution and diluted until the O.D. 600 nm was 0.2. Ninety microliters of EMS was mixed with 810 µL of sterile 0.1 M phosphate buffer (pH 7) and 100 µL of bacterial suspension. Samples obtained after 2 and 2.5 h were plated on MRS agar plates with 10 mM 2-deoxy-D-glucose (DOG) and 10 g/L of lactose. Grown colonies were replated on the same medium and stored in MRS broth with 30% glycerol at –80° C. One parallel of dilution was inoculated in MRS broth with 10 g/L lactose and 10 mM 2-deoxy-D-glucose and every 24 h plated on MRS agar plates and inoculated into the same fresh medium (10% v/v). Single colonies of survived bac-teria were stored in MRS broth with 30% glycerol. Growth of each mutant was tested in microtiter plates in modified MRS broth (1% lactose, 10 mM DOG), with absorbance measurement at 600 nm each hour for 8 h.

Example 5

Heat Killing of the *Bifidobacterium* strain *Bifidobacterium longum* (IM 937)

Figure 2A:
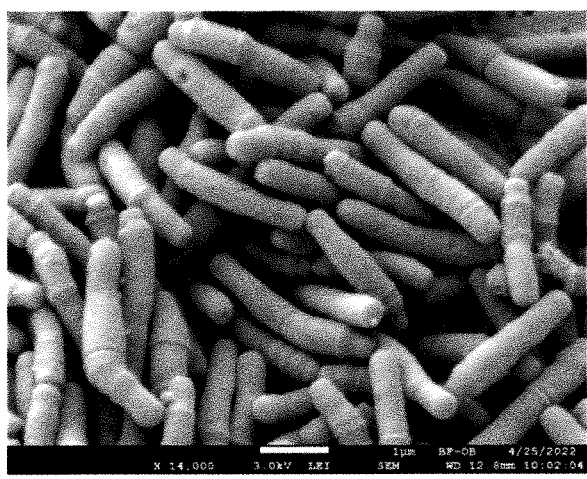
FIGS. 2A-C are micrographs showing heat inactivation of the *Bifidobacterium* strain *Bifidobacterium longum* IM 937 where

Bacterial strain *Bifidobacterium longum* (IM 937) (ATTC 15708) was cultivated in MRS broth at 37C in anaerobic conditions and divided into 3 samples. Two of these samples were killed by heating at 80° C. for 20 minutes. To confirm death of the bacterial cells in these samples a dilution series in a petri dish assay was performed, which resulted in zero colonies (See, FIG. 5). To evaluate the structure of the dead cells, all three samples were evaluated by scanning electron microscopy (SEM): an SEM micrograph showing the bac-terial taken before the heat-killing step is shown in FIG. 2A, an SEM micrograph taken immediately after the heat killing step is shown in FIG. 2B (note that the cell structures are still intact); and an SEM micrograph showing the bacterial taken 4 months after the killing step is shown in FIG. 2C.

Each sample was prepared for microscopy as follows. Bacterial culture was centrifuged at 3300 g for 5 min. The supernatant was discarded and the pellet was resuspended in ¼ strength Ringers solution. After centrifugation at 3300 g for 5 min the pellet was resuspended in 0.5 ml of Ringer solution and fixed in a mix of 0.5% glutaraldehyde and 1% formaldehyde in phosphate buffer at room temperature for up to 2 h. After washing in phosphate buffer samples were post-fixed in 1% OsO4 for 30 min. After washing in Milli-Q water, the samples were dehydrated in ethanol series of ascending concentrations (50%, 70%, 90% and 100%) for 3 min in each. 100% ethanol was gradually replaced by hexamethyldisilazane and allowed to air-dry overnight. Dried samples were attached to metal holders, covered with platinum and observed with a JEOL JSM-7500F field-emission scanning electron microscope.

Figure 2B:
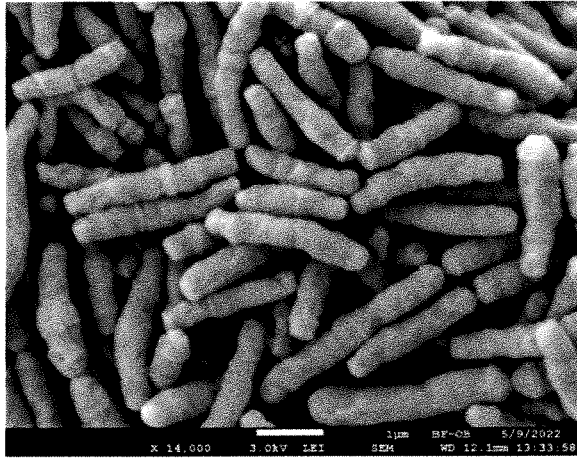
Figure 2C:
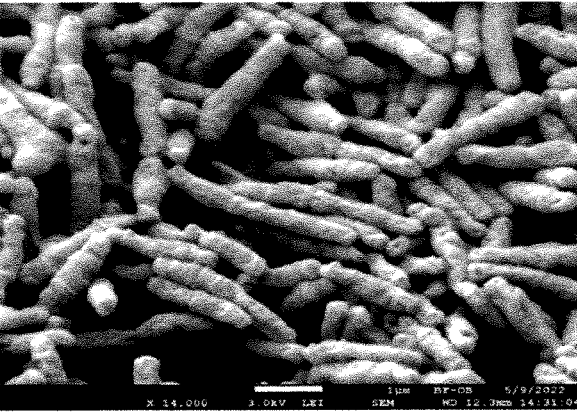

As can be seen in FIGS. 2B-C, the cell wall structures are not destroyed during the killing step. Instead, they are substantially intact after the killing step and remain even after the four months aging period.

Example 6

Evaluation of Tag Signals for Detection at Various Concen-trations Using Realtime PCR Experiments were conducted using a dilution series to determine and evaluate the concentrations at which the tags can still be detected. The experiments were performed with a number of different matrices and bacterial tags, and all experiments showed similar results. (See, FIG. 3). A dilution series of tags was generated at various concentrations from 100 ppm to 0.001 ppm (specifically, 100 ppm, 10 ppm, 1 ppm, 0.1 ppm, 0.01 ppm and 0.001 ppm). For simplicity, a sequence known to be unique to *Lactobacter acidophilus* bacteria with published primers was used as the tag sequence. (See, Walter et al., 2000, the disclosure of which is incorporated herein by reference in its entirety).

Figure 3:
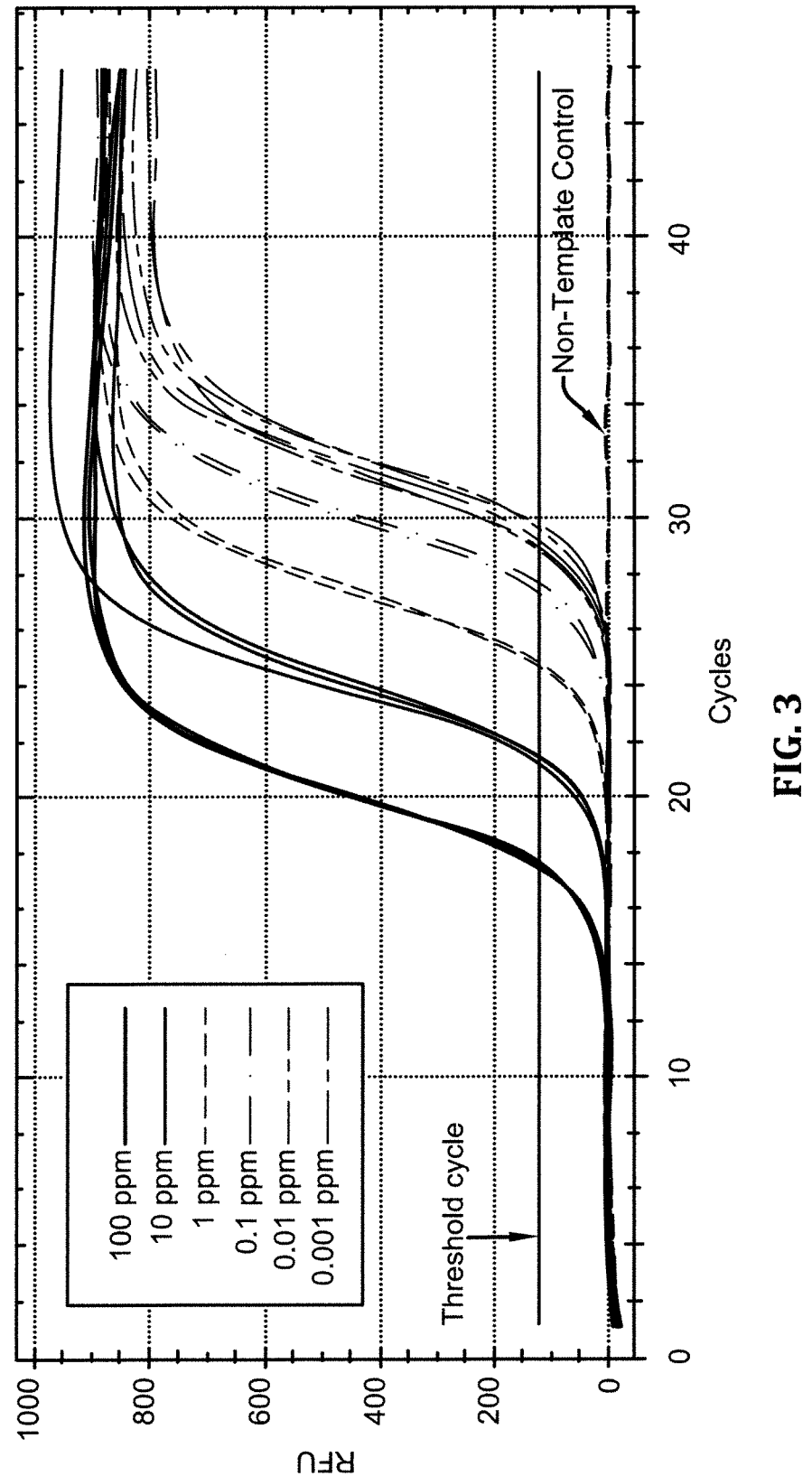
FIG. 3 are real time PCR readouts (Relative Fluorescence Units (RFU) v. Cycles) for PCR signals generated right after addition of tag containing samples at tag concentrations of from 100 ppm to 0.001 ppm to the real time PCT device measured over a range of from about 0 to about 50 cycles. As can be seen, tags can readily be detected at all reported concentrations. The highest concentration is detected after less than 20 cycles of PCR, whereas the lowest concentration took more than 30 cycles. These variations are expected given the relative initial concentrations. Note that the non-template control does not exceed the cycle threshold for a positive result.
Figure 5:
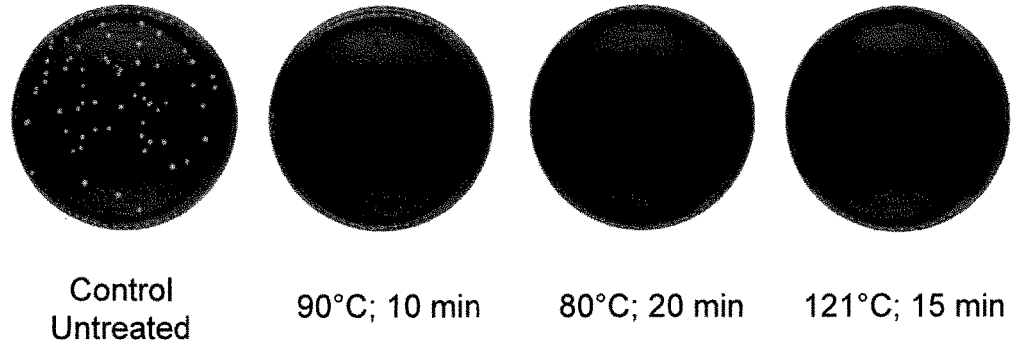
FIG. 5 is a comparison of images taken of bacterial growth at 37° C. in Petri dishes of the untreated control and heat killed bacteria (90° C. for 10 min; 80° C. for 20 min; and 121° C. for 15 min).
Figure 6A:
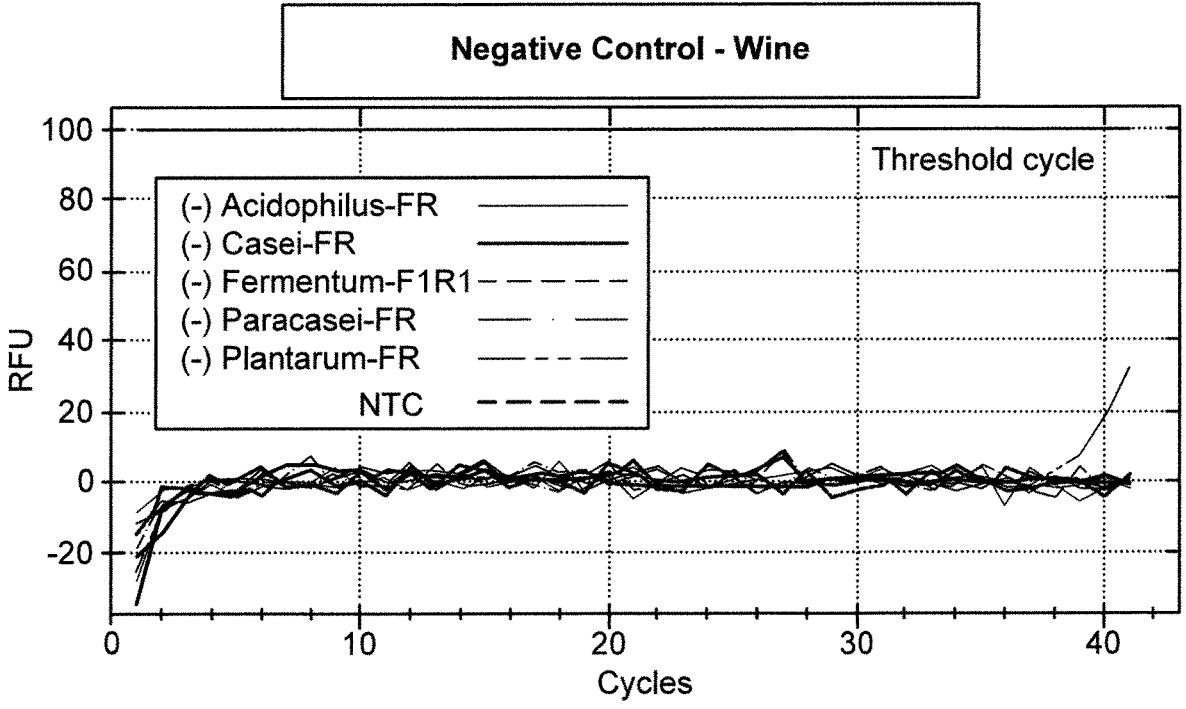
FIGS. 6A-E are real time PCR readouts (Relative Fluorescence Units (RFU) v. Cycles) of tag containing samples with tag concentrations of 10 ppm, 1 ppm, and 0.1 ppm in wine including a negative control for *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014); and *Limosilactobacillus fermentum* (ATCC 23271) in wine (FIG. 6A); *L. acidophilus* tags in concentrations of 10 ppm, 1 ppm, and 0.1 ppm in wine (FIG. 6B); *L. casei* tags in concentrations of 10 ppm, 1 ppm, and 0.1 ppm in wine (FIG. 6C); *L. paracasei* tags in concentrations of 10 ppm, 1 ppm, and 0.1 ppm in wine (FIG. 6D); and *L. plantarum* tags in concentrations of 10 ppm, 1 ppm, and 0.1 ppm in wine (FIG. 6E). The x-axis represents the number of cycles, and the y-axis represents the RFUs, or Relative Fluorescence Units, which are proportional to double stranded DNA concentration.
Figure 6B:
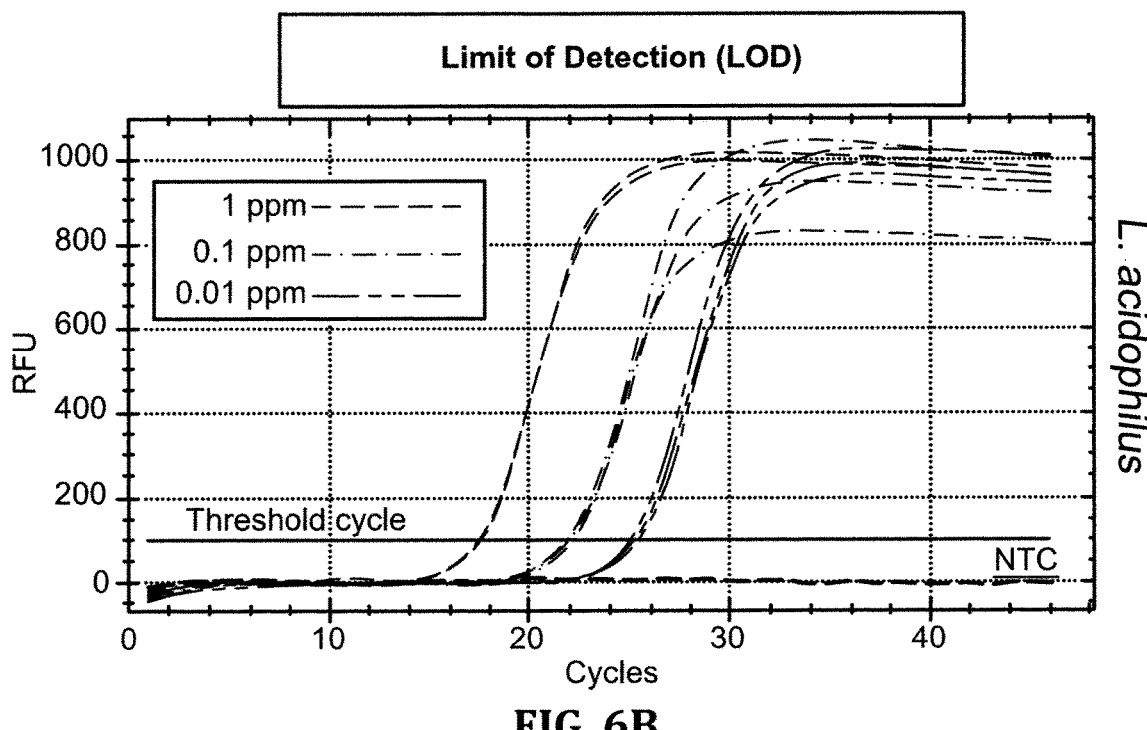
Figure 6C:
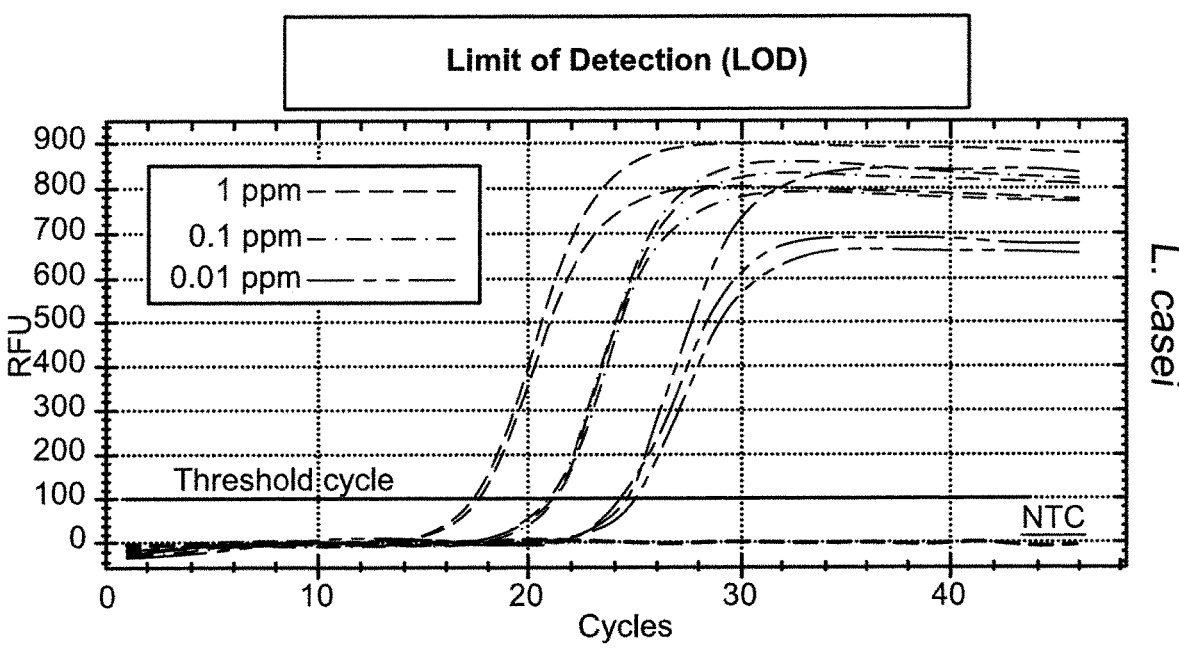
Figure 6D:
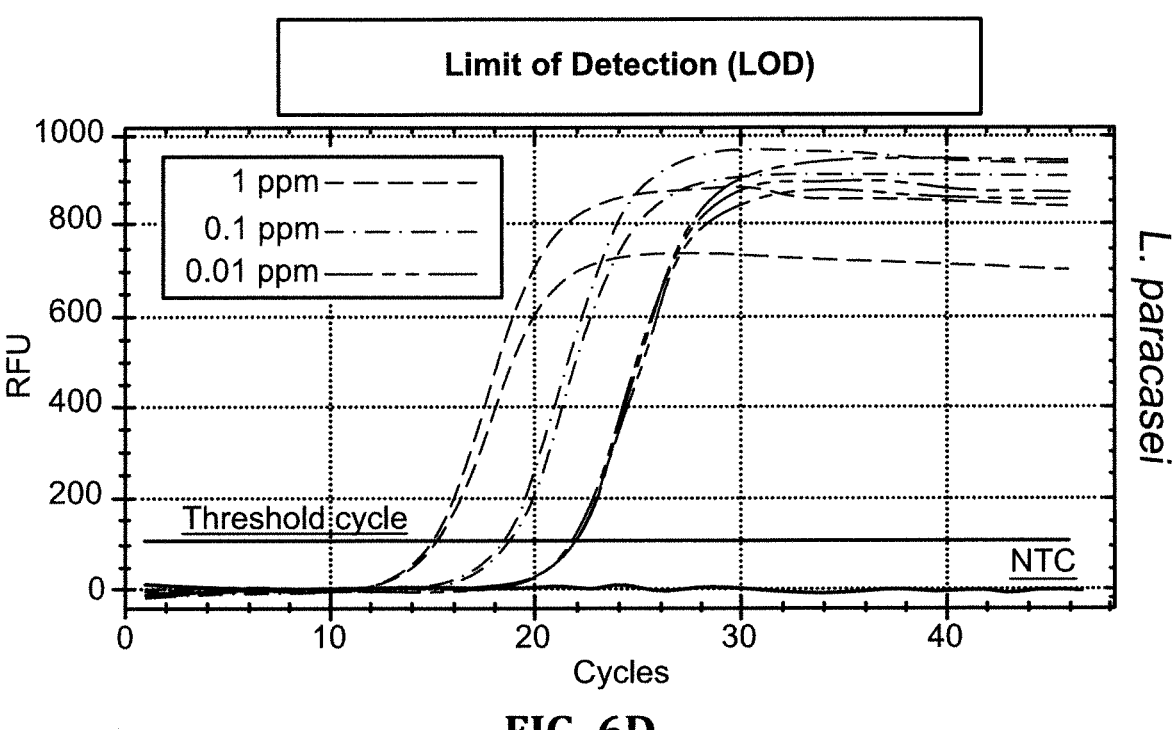
Figure 6E:
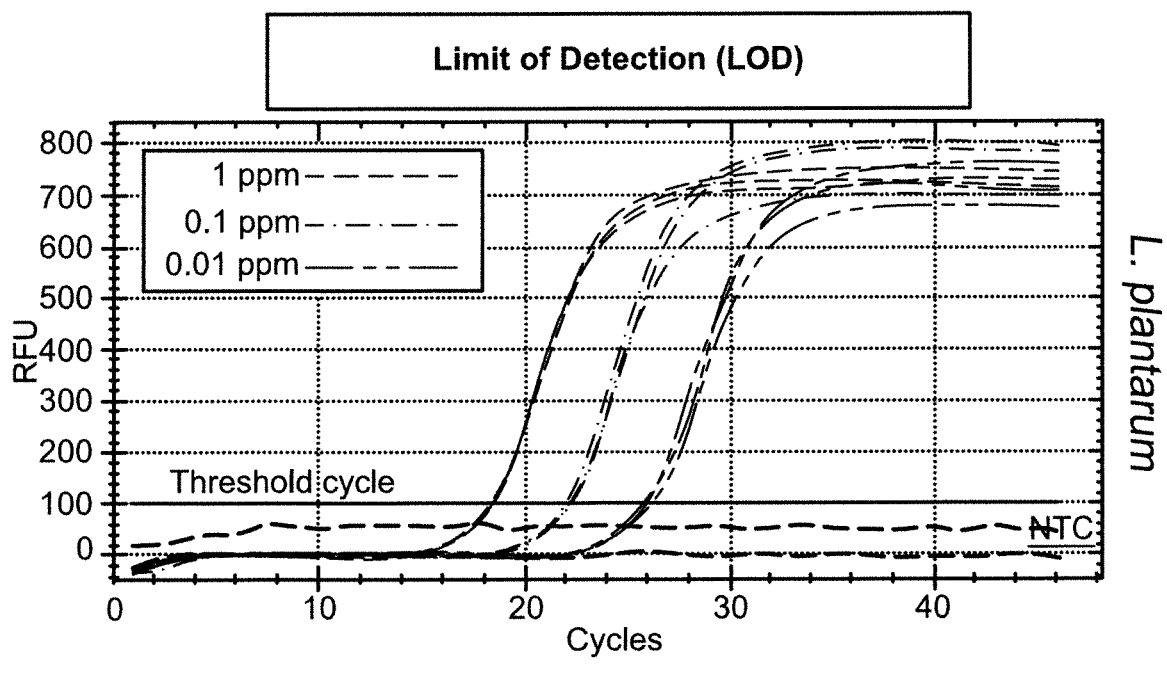

*Lactobacter acidophilus* bacteria containing the tag were heat killed as described in Example 5 above, and sampled at concentrations of 100 ppm, 10 ppm, 1 ppm, 0.1 ppm and 0.01 ppm in a dilution series (see FIG. 5). The samples were briefly boiled before PCR to free the DNA from the bacteria walls and then tested for detection using Realtime PCR (Bio Rad CFX96, BioRad Corporation, Hercules, CA), measured over a range of from about 0 to about 42 cycles. FIG. 3 shows the real time PCR readouts of the signals generated right after their addition to the Realtime PCT device. The x-axis represents the number of cycles, and the y-axis represents the RFUs, or Relative Fluorescence Units, which are proportional to double stranded DNA concentration.

As can be seen in FIG. 3 (See also, FIGS. 6B, 7B, 8B, 9B, 10B, 11B, 12B, 13B, 14B and 15B, the bacterial DNA tags could readily be detected in all cases, as evidenced by the increasing RFU as a function of the PCR cycle for each sample. The highest tag concentration was detected after less than 20 cycles of PCR, whereas the lowest tag concentration took more than 30 cycles. These variations are expected given the relative initial concentrations. A negative control (non-template control) did not yield a positive signal, as it does not exceed the cycle threshold for a positive result. Non-specific amplification can occur after more than forty cycles, so the amplification is routinely stopped at 42 cycles. The following primers were used to amplify the tag for detection: LacI: 5'-AGCTGAACCAACAGATTCAC-3' (SEQ ID No. 11) and LacII: 5'-ACTACCAGGGT-ATCTAATCC-3' (SEQ ID No. 12). (See, Table 1).

Example 7

Evaluation of Tag Stability at 4° C. and 40° C. Using Realtime PCR

Figure 4:
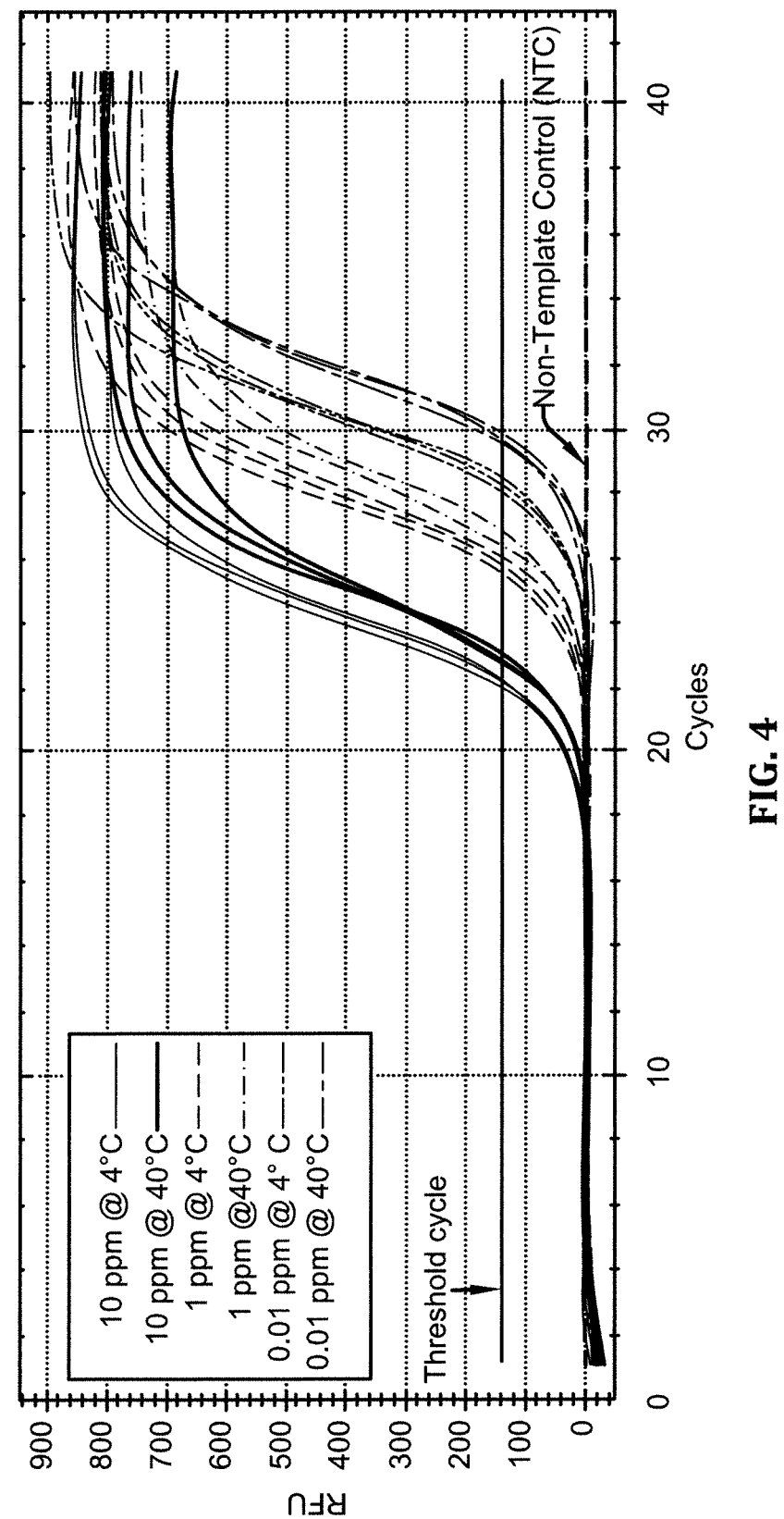
FIG. 4 are real time PCR readouts (Relative Fluorescence Units (RFU) v. Cycles) of tag containing samples with tag concentrations of 10 ppm, 1 ppm, and 0.1 ppm performed after 6 weeks of incubation at 4° C. and at 40° C., to demonstrate the stability of the tags. The presence of the tags were measured over a range of from about 0 to about 50 cycles and all tags were detected. And while some degradation occurred and more cycles were necessary to detect a signal, the detection time (in cycles) still ranged between about 20 and about 32 cycles. Note that the non-template control does not exceed the cycle threshold for a positive result.

As set forth above, the tags have to be stable over many months or even years in diverse matrices. To demonstrate the stability of the tags, real time PCR was performed using heat-killed *L. acidophilus* (ATCC 4356) preparations incubated at 4° C. and at 40° C. for a maximum of 6 weeks, for concentrations varying from 10 ppm to 0.1 ppm, in a matrix of maltodextrin as a test sample to be tagged. The results are shown in FIG. 4 which shows real time PCR readouts (Relative Fluorescence Units (RFU) v. Cycles) of tag containing samples with tag concentrations of 10 ppm, 1 ppm, and 0.1 ppm performed after 6 weeks of incubation at 4° C. and at 40° C., to demonstrate the stability of the tags. (See, FIG. 4) The presence of the tags were measured over a range of from about 0 to about 50 cycles and all tags were detected As can be seen, all tags could be detected after the incubation period at both temperatures. (See, FIG. 4). The higher temperature, 40° C., was used to simulate a longer incubation period at a lower temperature; at a temperature of 40° C., a six-week incubation was thought to correspond to an approximately 6-month incubation at room temperature. As some degradation of DNA occurred in the sample throughout the incubation, more cycles were necessary to detect a signal as compared to the analysis described in FIG. 3, but the cycles required were still in the range of approximately 20 and 32 cycles, significantly lower than the 42 cycles where unspecific amplification can occur. (See, FIG. 4). Note that the non-template control in FIG. 4 does not exceed the cycle threshold for a positive result. The same primers were used as in the experiment described in Example 8. (See also, FIG. 3). These experiments show that the tags are stable and are still detectable after long incubations.

Example 8

Evaluation of Microorganism Strains

To evaluate prospective microorganisms for use tags in the present invention, 15 different bacteria strains were cultivated and analyzed. Bacterial strains were grown, heat killed, and added to a sample matrix. After an incubation period at different temperatures, the detection protocol was applied to verify that the tags were detectable.

1. Bacterial Strains

Bacterial strains were grown in suitable media: MRS for lactobacilli and bifidobacteria and M17 for lactococci and streptococci. Bacterial cultures (10 ml) were centrifuged at 3300 g for 5 minutes. Supernatant was removed and pellet was resuspended in 1 ml of water. The bacterial strains used for these experiments are listed in Table 3.

TABLE 3

| List of bacterial strains used for analysis | |
| --- | --- |
| Internal number | Bacterial strain |
| IM 116 | *L. acidophilus* ATCC 4356 |
| IM 308 | *L. plantarum* ATCC 8014 |
| IM 33 | *L. casei* ATCC 393 |
| IM 242 | *L. paracasei* subsp. *paracasei* DSM 5622 |
| IM 419 | *B. bifidum* LMG 11041 |
| IM 545 | *B. longum* subsp. *infantis* LMG 8811 |
| IM 275 | *B. longum* ATCC 15708 |
| IM 245 | *Lc. lactis* subsp. *lactis* ATCC 19435 |

Enumeration of live cultivable bacteria was performed with inoculation of serially diluted suspension in MRS agar (Merck) for lactobacilli and bifidobacteria or M17 agar (Merck) for *Lactococcus lactis*, Str. *thermophilus* and *Enterococcus faecium*. MRS plates were incubated anaerobically at 37° C. for 72 hours, plates for enumeration of *Lactococcus lactis* were incubated aerobically at 30° C. for 72 hours while plates for enumeration of Str. *thermophilus* and *Enterococcus faecium* were incubated aerobically at 37° C. for 72 hours. After incubation, grown colonies were counted and number of CFU/5 μl was calculated.

2. Experiment 1: Positive Controls, Live Cultures

5 μl of each strain was mixed with 45 μl of water and DNA was extracted as described above. Moreover, 5 μl of each strain was added to 45 mg of maltodextrin and DNA was extracted. For negative controls DNA was extracted also from 45 μl of water and 45 mg of maltodextrin. Species specific PCR was performed for species added to the matrix.

3. Experiment 2: Positive Controls, Killed Cultures

500 μl of each strain was killed with heating at 95° C. for 10 min. 5 μl of each killed strain was mixed with 45 μl of water and DNA was extracted as described above. Moreover, 5 μl of each killed strain was added to 45 mg of maltodextrin and DNA was extracted. Species specific PCR was performed for species added to the matrix.

4. Experiment 3: Cross Reactivity, Live Cultures

Mixes of 14 different strains (5 μl of each strain) were prepared and the DNA was extracted as described above. Species specific PCR was performed for species that were not included in bacterial mix to test if there was any cross-reactivity with the primers and any of the non-target species.

5. Results

The results positive and negative control tests are collected in Table 4, below.

TABLE 4

| Bacterial strain | Amount of initial CFU/ sample | Positive control, live culture in water | Positive control, live culture in maltodextrin | Positive control, killed culture in water | Positive control, killed culture in maltodextrin | Negative control, live cultures (cross reactivity) |
| --- | --- | --- | --- | --- | --- | --- |
| *L. acidophilus* ATCC 4356 | $1.5 \times 10^5$ | + | + | − | − | − |
| *L. plantarum* ATCC 8014 | $3.4 \times 10^6$ | + | + | − | − | − |
| *L. casei* ATCC 393 | $2.4 \times 10^7$ | + | + | + | + | − |
| *B. bifidum* MG 11041 | $5.5 \times 10^6$ | + | + | + | + | − |

TABLE 4-continued

| Bacterial strain | Amount of initial CFU/ sample | Positive control, live culture in water | Positive control, live culture in maltodextrin | Positive control, killed culture in water | Positive control, killed culture in maltodextrin | Negative control, live cultures (cross reactivity) |
|---|---|---|---|---|---|---|
| *Lc. lactis* subsp. *lactis* ATCC 19435 | $4.2 \times 10^7$ | + | + | + | + | − |

These results show that the tags added to the samples could still be detected after incubation in most matrices, indicating a successful tagging experiment, and that the tags can be used for tracking purposes. No tag exhibited any cross reactivity with any other tags, enabling, for example, several tags to be used to label and later track different ingredients of a product independently.

Example 9

Detection of Lactobacteria Based Tags in Various Substances

In these experiments, four species of Lactobacteria, namely, *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014) were evaluated for use in forming tags for use in a variety of different products, including, water, maltodextrin, wine (see, FIGS. 6A-E), green coffee (see, FIGS. 7A-C), peanut butter (see, FIGS. 8A-E), vegan chicken, (see, FIGS. 9A-B), palm oil (see, FIGS. 10A-E), milk powder, (see, FIGS. 11A-D), vanilla extract (see, FIG. 12A-D, rose oil (see, FIGS. 13A-E), ground pepper (see, FIGS. 14A-D), and cinnamon (see, FIGS. 15A-E).

Negative Controls

As set forth above, the bacteria or other microorganisms to be used as a tag, should not be present in the material or product being tagged and as a negative control, real time PCR (Bio Rad CFX96, BioRad Corporation, Hercules, CA) was used to determine whether any of the above lactobacteria were present in the products and materials to be tagged. The results are shown in FIGS. 6A, 7A, 8A, 9A, 10A, 11A, 12A, 13A, 14A and 15A and in Table 5, below.

TABLE 5

| | Negative Controls | | | |
|---|---|---|---|---|
| | *L. acidophilus* | *L. casei* | *L. paracasei* | *L. plantarum* |
| Water | | | | |
| Maltodextrin | | | | Detected |
| Wine | | | | |
| Green Coffee | | | Detected | Detected |
| Peanut Butter | | | | |
| Vegan Chicken | Detected | Detected | | Detected |
| Palm oil | | | | |
| Milk powder | | | | Detected |
| Vanilla Extract | | | | Detected |
| Rose Oil | | | | |
| Ground Pepper | | | | Detected |
| Cinnamon | | | | |

Where a bacterium was detected in a product or material being tested, it was not used to form a tag for that material. For example, because *L. casei, L. paracasei,* and *L. plantarum* were all detected in the vegan chicken in the negative controls (see, Table 5 and FIG. 9A), only *L. acidophilus* was used to prepare tags for use with the vegan chicken (see, FIG. 9B). Similarly, green coffee was not evaluated with respect to tags made from *L. paracasei* and *L. plantarum* (see, Table 5 and FIG. 7A), and green coffee, vegan chicken, milk powder, vanilla extract and ground pepper were not evaluated with respect to tags made from *L. plantarum* (see, Table 5 and FIG. 7A).

Limit of Detection

Limit of Detection experiments were performed as set forth above in Example 2 above using tags made from one or more of *L. acidophilus, L. casei, L. paracasei,* and *L. plantarum* mixed with various substrates. The results are shown in Tables 6A-B and 6A-B and in FIGS. 6A-E, 7A-C, 8A-E, 9A-B, 10A-E, 11A-D, 12A-D, 13A-E, 14A-D, and 15A-E.

For each bacterium, the tags were generated by growing each bacterial culture in a suitable substrate and heat killing them at a temperature of 90° C. for 10-20 minutes. The tags were added to each material to form samples having concentrations of 10 ppm, 1 ppm and 0.1 ppm.

Real time PCR (Bio Rad CFX96, BioRad Corporation, Hercules, CA) was used to detect the tags using a threshold value of about 100 RFU over a period of from about 1 to about 42 cycles, depending upon the concentration of tags in the sample. As will be understood by those of ordinary skill in the art, a high number of cycles can result in a false positive reading and the number of cycles before this occurs will depend upon the particular tag being detected. Care should be taken to avoid a high number of cycles. The threshold value for detection will be the threshold value set by PCR manufacturer, which is generally about 100. For these experiments, a tag was deemed to be present if it is detected by PCR at a threshold value of about 100 RFU, in less than about 40 cycles.

As set forth above, *L. casei* tags were not evaluated with respect to vegan chicken; *L. paracasei* tags were not evaluated with respect to green coffee and vegan chicken; and *L. plantarum* tags were not evaluated with respect to green coffee, vegan chicken, vanilla extract, and ground pepper, since these bacteria were found to be present in these materials during the negative control testing. Since *L. acidophilus* was not found to be present in any of the tested materials during the negative controls, the *L. acidophilus* tags were tested in all of the materials. (See, Tables 6A-B, below)

TABLE 6A

| | | Malto- | | Green | Peanut | Vegan | Palm |
|---|---|---|---|---|---|---|---|
| Species | Water | dextrin | Wine | Coffee | Butter | Chicken | Oil |
| *L. acidophilus* | X | X | X | X | X | X | X |
| *L. casei* | X | X | X | X | X | — | X |
| *L. paracasei* | X | X | X | — | X | — | X |
| *L. plantarum* | X | X | X | — | X | — | X |

X = detection of species tags at concentrations of 10 ppm, 1 ppm and 0.1 ppm

TABLE 6B

Limit of Detection Results for Lactobacteria
in Various Products(2 of 2)

| | Milk | Vanilla | | Ground | |
|---|---|---|---|---|---|
| Species | Powder | Extract | Rose Oil | Pepper | Cinnamon |
| *L. acidophilus* | X | X | X | X | X |
| *L. casei* | X | X | X | X | X |
| *L. paracasei* | X | X | X | X | X |
| *L. plantarum* | X | — | X | — | X |

"X": detection of species tag at concentrations of 10 ppm, 1 ppm and 0.1 ppm
"—": not tested As can be seen in FIGS. 6-15 and Tables 7A-B, below, all of the tags tested were detected at all concentrations (1 ppm, 0.1 ppm, and 0.01 ppm).

TABLE 7A

Limit of Detection Values (in Cycles) for Various Products(1 of 2)

| Species | | Water | Malto-dextrin | Wine | Green Coffee | Peanut Butter | Vegan Chicken | Palm Oil |
|---|---|---|---|---|---|---|---|---|
| *L. acidophilus* | 10 ppm | 18.06 | 21.32 | 17.38 | 27.39 | 27.49 | 21.29 | 21.61 |
| | 1 ppm | 21.15 | 24.74 | 21.95 | 31.76 | 30.33 | 24.12 | 22.89 |
| | 0.1 ppm | 26.17 | 27.46 | 25.15 | 32.52 | 34.15 | 26.94 | 27.92 |
| *L. casei* | 10 ppm | 17.12 | 18.82 | 17.42 | 22.87 | 23.38 | — | 22.43 |
| | 1 ppm | 20.23 | 21.57 | 20.94 | 26.20 | 25.85 | — | 25.22 |
| | 0.1 ppm | 23.02 | 25.10 | 24.61 | 26.11 | 30.04 | — | 28.86 |
| *L. paracasei* | 10 ppm | 15.24 | 17.87 | 15.15 | — | 21.76 | — | 17.15 |
| | 1 ppm | 18.53 | 21.44 | 18.66 | — | 24.04 | — | 22.05 |
| | 0.1 ppm | 21.86 | 24.28 | 21.93 | — | 25.13 | — | 24.10 |
| *L. plantarum* ATCC | 10 ppm | 18.35 | 20.31 | 18.37 | — | 27.33 | — | 19.43 |
| | 1 ppm | 22.70 | 25.50 | 22.09 | — | 24.68 | — | 22.54 |
| | 0.1 ppm | 25.97 | 27.05 | 26.06 | — | 33.07 | — | 24.17 |

"—": not tested

TABLE 7B

Limit of Detection Values (in Cycles) for Various Products(2 of 2)

| Species/Concentration | | Milk Powder | Vanilla Extract | Rose Oil | Ground Pepper | Cin-namon |
|---|---|---|---|---|---|---|
| *L. acidophilus* | 10 ppm | 29.60 | 16.59 | 26.21 | 30.26 | 30.24 |
| | 1 ppm | 34.12 | 19.34 | 30.46 | 31.62 | 34.05 |
| | 0.1 ppm | 35.30 | 21.07 | 34.56 | 34.19 | 34.88 |
| *L. casei* | 10 ppm | 25.59 | 18.19 | 20.41 | 21.11 | 22.02 |
| | 1 ppm | 29.73 | 21.12 | 24.67 | 24.53 | 25.04 |
| | 0.1 ppm | 31.88 | 24.45 | 27.52 | 27.70 | 27.65 |
| *L. paracasei* | 10 ppm | 25.86 | 15.54 | 21.98 | 20.56 | 21.01 |
| | 1 ppm | 29.09 | 19.05 | 27.38 | 24.19 | 24.25 |
| | 0.1 ppm | 31.96 | 22.19 | 30.07 | 27.05 | 26.40 |
| *L. plantarum* | 10 ppm | — | — | 23.09 | — | 24.28 |
| | 1 ppm | — | — | 25.88 | — | 27.61 |
| | 0.1 ppm | — | — | 29.19 | — | 30.22 |

"—": not tested

As will be apparent, the detection values in Tables 7A and 7B represent the number of cycles required to reach 100 RFU.

Example 10

Evaluation of Tags formed from *Lactocaseibacillus paracasei* (IM 932), *Bifidobacterium longum* (IM 937), *Lactococcus lactis* (IM 145), and *Streptococcus thermophilus* (IM 1629) in Various Substances In these experiments, tags were formed *Lactocaseibacillus paracasei* (IM 932), *Bifidobacterium longum* (IM 937), *Lactococcus lactis* (IM 145), and *Streptococcus thermophilus* (IM 1629).

Methods and Materials

1. Bacterial Strains

Preparation of bacterial suspension: The selected bacterial strains were grown in suitable media, Specifically, the *Lactocaseibacillus paracasei* (IM 932) was grown in De Man, Rogosa and Sharpe agar (MRS) broth (anacrobic incubation at 37° C.), the *Bifidobacterium longum* IM 937 was grown in MRS broth (anaerobic incubation at 37° C.), the *Lactococcus lactis* IM 145 in M17 broth (aerobic incubation at 30° C.) and the *Streptococcus thermophilus* IM 1629 in M17 broth (acrobic incubation at 37° C.). The bacterial cultures (10 ml) were centrifuged at 3300 g for 5 minutes. Supernatant was removed and pellet was resuspended in 1 ml of water.

Killing of the bacterial strains: 500 μl of bacterial suspension was killed with heating above 90° C. for 5 min, followed by cooling on ice.

Enumeration of bacteria in bacterial suspension: Enumeration was performed by flow cytometry. using the "BD™ Cell Viability with counting beads" kit by Becton Dickinson (Franklin Lakes, NJ) which enables fast and reliable calculation of viable and non-viable cells. Since there was high number of bacterial cells in the suspensions, prior to analysis bacterial suspensions were serially diluted in sterile ¼ strength Ringer solution.

2. Phase 2: Experiments with Different Dilutions in Different Matrices

Heat killed bacterial suspensions were serially diluted in water. Two consecutive decimal dilutions were used for DNA isolation: 5 μl of each strain dilution was added to 45 mg/µl of matrix and the DNA was extracted. The matrices used were ground pepper, cinnamon, milk powder, vanilla extract (in 35% EtOH), rose oil, and red wine.

Positive controls: As positive control, live bacterial suspension was used. The suspension was diluted (the same way as killed suspensions). 5 µl of the lowest dilution was added to 45 mg of each matrix and DNA was extracted.

Negative control: DNA was extracted from matrix without addition of the strains and this DNA was used as negative control.

DNA extraction: 0.4 mL of TE buffer containing 4 mg of lysozyme (Sigma Chemical, St. Louis, USA) and 4 µL of mutanolysine (2500 U/mL) (Sigma Chemical, St. Louis, USA) was added to the samples. After 2 h incubation at 37° C., DNA was isolated using Maxwell 16 Tissue DNA Purification Kit (Promega, Madison, USA) according to the manufacturer's protocols.

Species-specific PCR: Reaction mixes for species specific PCR (20 µL) contained MyTax buffer (Bioline) with 3 mM $MgCl_2$ and 0.1 mM dNTP, 0.5 µM oligonucleotide primers, 0.1 µl My Taq Red DNA polymerase and 2 µL DNA. Real time PCR reactions (Bio Rad CFX96, BioRad Corporation, Hercules, CA) were performed using specific primers and reaction conditions described in Table 8, below.

TABLE 8

Used primers and PCR conditions

| Target species | Primers | PCR protocol | No of cycles | Product length | References |
|---|---|---|---|---|---|
| Bifido-bacterium longum | F: 5'-CAGTTGATCGCATGGTCTT-3' (SEQ ID NO. 5) R: 5'-TACCCGTCGAAGCCAC-3' (SEQ ID NO. 6) | 95° C./3 min 95° C./15 s 60° C./20 s 72° C./30 s 72° C./5 min | 1 30 1 | 106 bp | Malinen et al., 2003 |
| Lactocasei-bacillus paracasei | Para1: 5'-CACCGAGATTCAACATGG-3' (SEQ ID NO. 17) Y2: 5'-CCCACTGCTGCCTCCCGTAGGAGT-3' (SEQ ID NO. 18) | 95° C./3 min 95° C./30 s 55° C./30 s 72° C./30 s 72° C./5 min | 1 30 1 | 290 bp | Ward et al., 1999 |
| Lactococcus lactis | 27f: 5'-AGAGTTTGATCMTGGCTCAG-3' (SEQ ID NO. 27) LIa: 5'-CAGTCGGTACAAGTACCAAC-3' (SEQ ID NO. 28) | 95° C/3 min 95° C./30 s 55° C./30 s 72° C./30 s 72° C./5 min | 1 30 1 | 87 bp | Barakat et al., 2000 |
| Strepto-coccus salivarius subsp. thermophilus | ThI: 5'-ACGGAATGTACTTGAGTTTC-3' (SEQ ID NO. 29) ThII: 5'-TTTGGCCTTTCGACCTAAC-3' (SEQ ID NO. 30) | 95° C/3 min 95° C./30 s 58° C./30 s 72° C./30 s 72° C./5 min | 1 30 1 | 205-304 bp | Tilsala-Timisjärvi in Alatossava, 1997 |

3. Comparison of Live Bacteria Vs. Heat Killed Bacteria
Serial dilutions of all four live bacteria and heat killed bacteria. The dilutions were added to milk powder. The DNA was extracted and isolated, and PCR was performed as described in phase 2, above.

Results

A). Limit of Detection of Heat Killed Bacteria in Different Matrices
Limit of detectability of heat killed selected bacterial strains in different matrices is shown in Table 9.

TABLE 9

PCR detection of serial diluted heat killed bacterial strains and control strains in different matrices

| Strain | Number of bacteria in sample/ Matrix | Heat killed strain | | | Live strain | | | Neg. control | Control strain |
|---|---|---|---|---|---|---|---|---|---|
| | | $1^{st}$ dilution | $2^{nd}$ dilution | $3^{rd}$ dilution | $1^{st}$ dilution | $2^{nd}$ dilution | $3^{rd}$ dilution | | |
| Lb. | CFU/sample | $3*10^6$ | $3*10^5$ | $3*10^4$ | $3*10^6$ | $3*10^5$ | $3*10^4$ | / | n.d. |
| paracasei | Ground pepper | – | – | / | – | / | / | – | + |
| IM 932 | Cinnamon | – | – | / | – | / | / | – | |
| | Milk powder | + | + | + | + | + | + | – | |
| | Vanilla extract | + | + | / | + | / | / | – | |
| | Rose oil | + | + | / | + | / | / | – | |
| | Red wine | + | + | / | + | / | / | – | |

TABLE 9-continued

| | | PCR detection of serial diluted heat killed bacterial strains and control strains in different matrices | | | | | | | |
|---|---|---|---|---|---|---|---|---|---|
| | Number of bacteria in | Heat killed strain | | | Live strain | | | | |
| Strain | sample/ Matrix | $1^{st}$ dilution | $2^{nd}$ dilution | $3^{rd}$ dilution | $1^{st}$ dilution | $2^{nd}$ dilution | $3^{rd}$ dilution | Neg. control | Control strain |
| *Bif.* | CFU/sample | $2*10^6$ | $2*10^5$ | $2*10^4$ | $2*10^6$ | $2*10^5$ | $2*10^4$ | / | n.d. |
| *longum* | Ground pepper | – | – | / | – | / | / | – | + |
| IM 937 | Cinnamon | – | – | / | – | / | / | – | |
| | Milk powder | + | – | – | + | + | – | – | |
| | Vanilla extract | + | – | / | + | / | / | – | |
| | Rose oil | + | + | / | + | / | / | – | |
| | Red wine | + | + | / | + | / | / | – | |
| *Lc.* | CFU/sample | $2*10^7$ | $2*10^6$ | $2*10^5$ | $2*10^7$ | $2*10^6$ | $2*10^5$ | / | |
| *lactis* | Ground pepper | + | + | / | + | / | / | – | + |
| IM 145 | Cinnamon | – | – | / | – | | | – | |
| | Milk powder | + | + | + | + | + | + | – | |
| | Vanilla extract | + | + | / | + | / | / | – | |
| | Rose oil | + | + | / | + | / | / | – | |
| | Red wine | + | + | / | + | / | / | – | |
| *Str.* | CFU/sample | $4*10^6$ | $4*10^5$ | $4*10^4$ | $6*10^6$ | $6*10^5$ | $6*10^4$ | / | n.d. |
| *thermo-* | Ground pepper | + | – | / | + | / | / | – | + |
| *philus* | Cinnamon | – | – | / | – | / | / | – | |
| IM 1629 | Milk powder | + | + | + | + | + | + | – | |
| | Vanilla extract | + | + | / | + | / | / | – | |
| | Rose oil | + | + | / | + | / | / | – | |
| | Red wine | + | + | / | + | / | / | – | |

Legend:
+: PCR product was present;
–: PCR product was not present;
/, n.d.: not determined B). Comparison of Detection Limit of Live Bacteria Vs. Heat Killed Bacteria Comparison was performed in milk powder samples, results are shown in table 2. For *Bif. longum* IM 397 the detection limit of live bacteria is 10 times lower than detection of heat killed strain Example 12

Stability of Lactobacterial Tags in Various Substances

Tags were generated from four species of *Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014) as set forth above, and their stability evaluated in various media. As can be seen in Tables 10A-B, below, the stability of tags from the species of lactobacteria tested (*Lactobacillus acidophilus* (ATCC 4356), *Lactocaseibacillus casei* (ATCC 393), *Lactocaseibacillus paracasei* (DSM 5622), *Lactiplantibacillus plantarum* (ATCC 8014)) was evaluated at 6 months in the maltodextrin medium. The stability of the *Lactobacillus acidophilus* and *Lactocaseibacillus casei* tags was evaluated at 3 and 6 months in the milk powder and rose oil, and the *Lactobacillus acidophilus* tags were evaluated at 6 months in maltodextrin and wine (10 ppm) and at both 3 and 6 months in green coffee, peanut butter, vegan chicken, palm oil (10 and 1 ppm), milk powder (10 and 1 ppm), vanilla extract, rose oil (10 and 1 ppm), ground pepper (10 and 1 ppm), and cinnamon. The results are shown in Tables 10A-B and 11A-B below.

The stability of the tags was evaluated by detection via PCR as set forth above, at the time frames and concentrations indicated of (10 ppm, 1 ppm and 0.1 ppm), as shown in Tables 10A-B.

TABLE 10A

| | Stability Results for Lactobacteria in Various Products 1 of 2) | | | | | | | | | |
|---|---|---|---|---|---|---|---|---|---|---|
| | Malto-dextrin | Wine | Green Coffee | | Peanut Butter | | Vegan Chicken | | Palm Oil | |
| Species | 6 wk | 6 wk | 3 wk | 6 wk | 3 wk | 6 wk | 3 wk | 6 wk | 3 wk | 6 wk |
| *L. acidophilus* | X | X | X | X | X | X | X | X | X | X |
| *L. casei* | X | — | — | — | — | — | — | — | — | — |
| *L. paracasei* | X | — | — | — | — | — | — | — | — | — |
| *L. plantarum* ATCC | X | — | — | — | — | — | — | — | — | — |

"X": detection at concentrations of 10 ppm, 1 ppm and 0.1 ppm

"—": not tested

TABLE 10B

Stability Results for Lactobacteria in Various Products (2 of 2)

| Species | Milk Powder | | Vanilla Extract | | Rose Oil | | Ground Pepper | | Cinnamon | |
|---|---|---|---|---|---|---|---|---|---|---|
| | 3 wk | 6 wk | 3 wk | 6 wk | 3 wk | 6 wk | 3 wk | 6 wk | 3 wk | 6 wk |
| *L. acidophilus* | X | X | X | X | X | X | X | X | X | X |
| *L. casei* | X | X | — | — | X | X | — | — | — | — |
| *L. paracasei* | — | — | — | — | — | — | — | — | — | — |
| *L. plantarum* ATCC | — | — | — | — | — | — | — | — | — | — |

"X": detection at concentrations of 10 ppm, 1 ppm and 0.1 ppm
"—": not tested

TABLE 11A

Stability Results (in cycles) for Lactobacteria in Various Products (1 of 2)

| Species/Concentration | | Malto-dextrin | Wine | Green Coffee | | Peanut Butter | | Vegan Chicken | | Palm Oil | |
|---|---|---|---|---|---|---|---|---|---|---|---|
| | | 6 wk | 6 wk | 3 wk | 6 wk | 3 wk | 6 wk | 3 wk | 6 wk | 3 wk | 6 wk |
| *L. acidophilus* | 10 ppm | 22.99 | 34.84 | 28.31 | 29.01 | 28.93 | 28.98 | 23.04 | 24.41 | 27.41 | 29.74 |
| | 1 ppm | 26.51 | n.d. | 31.09 | 31.51 | 31.43 | 32.01 | 26.18 | 27.37 | 29.21 | 33.48 |
| | 0.1 ppm | 29.67 | n.d. | 33.44 | 35.55 | 34.18 | 35.53 | 28.83 | 29.19 | n.d | n.d. |
| *L. casei* | 10 ppm | — | — | — | — | — | — | — | — | — | — |
| | 1 ppm | — | — | — | — | — | — | — | — | — | — |
| | 0.1 ppm | — | — | — | — | — | — | — | — | — | — |

"X": detection at concentrations of 10 ppm, 1 ppm and 0.1 ppm
"—": not tested

TABLE 11B

Stability Results (in cycles for Lactobacteria tags in Various Products (2 of 2)

| Species/Concentration | | Milk Powder | | Vanilla Extract | | Rose Oil | | Ground Pepper | | Cinnamon | |
|---|---|---|---|---|---|---|---|---|---|---|---|
| | | 3 wk | 6 wk | 3 wk | 6 wk | 3 wk | 6 wk | 3 wk | 6 wk | 3 wk | 6 wk |
| *L. acidophilus* | 10 ppm | 32.67 | 35.69 | 18.93 | 20.06 | 28.36 | 30.54 | 32.25 | 32.03 | 29.29 | 31.06 |
| | 1 ppm | 35.01 | n.d. | 22.68 | 24.23 | 30.69 | n.d. | 33.10 | 33.45 | 33.73 | 34.45 |
| | 0.1 ppm | n.d | n.d. | 26.29 | 26.64 | n.d | n.d. | n.d | n.d. | 35.65 | 35.25 |
| *L. casei* | 10 ppm | 25.55 | 25.45 | — | — | 21.82 | 22.07 | — | — | — | — |
| | 1 ppm | 31.42 | 31.63 | — | — | 26.04 | 26.46 | — | — | — | — |
| | 0.1 ppm | 34.41 | 36.13 | — | — | 34.19 | n.d. | — | — | — | — |

"X": detection at concentrations of 10 ppm, 1 ppm and 0.1 ppm
"—": not tested

In light of the foregoing, it should be appreciated that the present invention significantly advances the art by providing a method for confirming the identity of an item or product by means of a bacterial tag that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

APPENDIX 1

TABLE 12

| Position in reference genome (IM 932) | IM 932 | MUT1 |
|---|---|---|
| 109619 | G | A |
| 111163 | C | T |
| 418710 | C | T |
| 748176 | G | T |
| 1040862 | G | A |
| 1682241 | T | C |

TABLE 12-continued

| Position in reference genome (IM 932) | IM 932 | MUT1 |
|---|---|---|
| 1975988 | T | C |
| 2491917 | A | G |
| 2491938 | A | G |
| 2492029 | A | G |
| 2492043 | T | C |
| 2492070 | G | A |
| 2492073 | C | T |
| 2492140 | G | A |
| 2492143 | A | G |
| 2492153 | G | A |
| 2492164 | T | C |
| 2686432 | T | A |
| 2707221 | G | T |
| 2709888 | G | T |
| 2710327 | C | T |
| 2810983 | C | A |
| 2832948 | T | C |
| 2897362 | C | T |
| 3025089 | G | T |
| 3028722 | T | C |
| 3029158 | G | A |
| 3029271 | G | T |
| 3029400 | C | T |
| 3031543 | T | G |
| 3033323 | G | A |
| 3033324 | C | G |
| 3034146 | T | G |
| 3036759 | A | C |
| 3038707 | C | T |
| 3038709 | C | T |
| 3038710 | T | G |
| 3038711 | G | A |
| 3038712 | G | A |
| 3041803 | G | T |
| 3041804 | A | G |

TABLE 13

| Position in reference genome (IM 932) | IM 932 | MUT2 |
|---|---|---|
| 4457 | T | C |
| 689620 | A | G |
| 871700 | G | A |
| 1104636 | G | A |
| 1208971 | A | T |
| 1460443 | T | C |
| 1609618 | A | C |
| 1682241 | T | C |
| 1916093 | A | G |
| 2006074 | T | C |
| 2127675 | A | T |
| 2159286 | G | A |
| 2204665 | C | T |
| 2491917 | A | G |
| 2491938 | A | G |
| 2492029 | A | G |
| 2492043 | T | C |
| 2492070 | G | A |
| 2492073 | C | T |
| 2492140 | G | A |
| 2492143 | A | G |
| 2492153 | G | A |
| 2492164 | T | C |
| 2735719 | C | T |
| 2741745 | T | C |
| 2835044 | G | A |
| 3028722 | T | C |
| 3029271 | G | T |
| 3029400 | C | T |
| 3029401 | G | T |
| 3029402 | A | G |

TABLE 13-continued

| Position in reference genome (IM 932) | IM 932 | MUT2 |
|---|---|---|
| 3031543 | T | G |
| 3032024 | T | A |
| 3033323 | G | A |
| 3033324 | C | G |
| 3033736 | G | C |
| 3034140 | A | G |
| 3034141 | G | A |
| 3034142 | A | T |
| 3034144 | C | G |
| 3034145 | A | C |
| 3034146 | T | G |
| 3034674 | G | T |
| 3034703 | T | C |
| 3035347 | A | C |
| 3035414 | G | A |
| 3035740 | C | T |
| 3035982 | T | C |
| 3036632 | A | G |

TABLE 14

| Position in reference genome (IM 932) | IM 932 | MUT3 |
|---|---|---|
| 557960 | C | T |
| 557980 | C | T |
| 1465351 | A | G |
| 1609618 | A | C |
| 1673528 | G | A |
| 1682241 | T | C |
| 2223167 | C | T |
| 2297590 | T | C |
| 2383535 | G | A |
| 2491788 | G | A |
| 2491917 | A | G |
| 2491938 | A | G |
| 2492029 | A | G |
| 2492043 | T | C |
| 2492070 | G | A |
| 2492073 | C | T |
| 2492140 | G | A |
| 2492143 | A | G |
| 2492153 | G | A |
| 2492164 | T | C |
| 2587029 | C | T |
| 2600808 | T | A |
| 2731699 | C | T |
| 3026699 | A | G |
| 3028722 | T | C |
| 3029400 | C | T |
| 3029986 | A | C |
| 3029987 | G | A |
| 3031543 | T | G |
| 3033323 | G | A |
| 3033324 | C | G |
| 3033736 | G | C |
| 3034140 | A | G |
| 3034141 | G | A |
| 3034142 | A | T |
| 3034146 | T | G |
| 3034703 | T | C |
| 3035347 | A | C |
| 3035740 | C | T |
| 3036632 | A | G |
| 3037903 | G | A |
| 3039106 | T | C |
| 3039115 | T | C |
| 3044610 | A | C |
| 3044611 | A | C |
| 3044613 | T | A |

TABLE 14-continued

| Position in reference genome (IM 932) | IM 932 | MUT3 |
|---|---|---|
| 3044614 | A | T |
| 3044615 | T | G |

TABLE 15

| Position in reference genome (IM 932) | IM 932 | MUT4 |
|---|---|---|
| 69726 | G | A |
| 124603 | G | T |
| 972036 | A | T |
| 1478907 | C | T |
| 1481278 | C | T |
| 1682241 | T | C |
| 1948012 | T | C |
| 2429993 | G | A |
| 2430314 | G | T |
| 2430315 | G | A |
| 2431932 | G | A |
| 2491917 | A | G |
| 2491938 | A | G |
| 2492029 | A | G |
| 2492043 | T | C |
| 2492070 | G | A |
| 2492073 | C | T |
| 2492140 | G | A |
| 2492143 | A | G |
| 2492153 | G | A |
| 2492164 | T | C |
| 2647603 | G | T |
| 2834640 | T | C |
| 2971884 | C | G |
| 3028722 | T | C |
| 3029271 | G | T |
| 3029400 | C | T |
| 3031052 | C | G |
| 3031055 | T | G |
| 3031056 | A | G |
| 3031543 | T | G |
| 3033323 | G | A |
| 3034145 | A | C |
| 3034146 | T | G |
| 3035740 | C | T |
| 3036054 | T | C |

TABLE 15-continued

| Position in reference genome (IM 932) | IM 932 | MUT4 |
|---|---|---|
| 3036632 | A | G |
| 3044615 | T | G |

TABLE 16

| Position in reference genome (IM 932) | IM 932 | MUT5 |
|---|---|---|
| 967039 | G | A |
| 981484 | C | A |
| 983663 | T | C |
| 986740 | T | C |
| 997457 | T | C |
| 1609618 | A | C |
| 1609620 | A | G |
| 1682241 | T | C |
| 1725519 | G | A |
| 1833559 | G | A |
| 2204665 | C | T |
| 2245892 | G | A |
| 2380075 | A | G |
| 2491917 | A | G |
| 2491938 | A | G |
| 2492029 | A | G |
| 2492043 | T | C |
| 2492070 | G | A |
| 2492073 | C | T |
| 2492140 | G | A |
| 2492143 | A | G |
| 2492153 | G | A |
| 2492164 | T | C |
| 3017902 | C | T |
| 3018662 | C | T |
| 3028722 | T | C |
| 3029271 | G | T |
| 3029400 | C | T |
| 3031052 | C | G |
| 3033735 | T | G |
| 3033736 | G | C |
| 3034146 | T | G |
| 3034703 | T | C |
| 3035740 | C | T |
| 3036632 | A | G |
| 3036759 | A | C |

What is claimed is:

1. A method for confirming the identity of an item or product by means of a food compatible microbial tag comprising:

A identifying a food compatible microorganism having a cell wall and genomic DNA or plasmid DNA, wherein said genomic or plasmid DNA comprises one or more target nucleotide sequence of at least 10 base pairs in length, said target nucleotide sequence not being present in the item or product to be tagged;

B selecting at least one of said one or more target nucleotide sequence to serve as a tag, and saving the target nucleotide sequence or sequences selected to serve as a tag and the identity of the item or product to be tagged in a database;

C killing said food compatible microorganism to create at least one tag comprising the target nucleotide sequence or sequences selected to serve as a tag;

D adding one or more of said at least one tag to an item;

E later confirming the identity of the tagged item by:

E.1 extracting the nucleotide sequence or sequences from said item and adding primers for each target nucleotide sequence or sequences as recorded in the database;

E.2 amplifying each of said target nucleotide sequence or sequences using polymerase chain reaction (PCR) techniques;

E.3 sequencing each amplified target nucleotide sequence; and

E.4 comparing each amplified target nucleotide sequence generated in step E3 to the nucleotide sequence saved for the target nucleotide sequence in step B and confirming that they match, thereby confirming the identity of the product.

2. The method of claim 1 wherein, the food compatible microorganism is a probiotic bacterium.

3. The method of claim 1 wherein, the food compatible microorganism is a bacterium selected from the group consisting of Firmicutes (*lactobacillus*), actinobacteria (bifidobacterial), and combinations thereof.

4. The method of claim 1 wherein, the food compatible microorganism is a bacterium selected from the group consisting of *Bifidobacterium animalis* subsp. *Lactis* (BB12), *Bifidobacterium bifidum* (LMG 11041), *Bifidobacterium longum* (ATCC 15708), *Bifidobacterium longum* subsp. *Infantis* (LMG 8811), *Enterococcus faecium* (ATCC 6057), *Lactobacillus acidophilus* ATCC 4356), *Lactocaseibacillus casei* (ATCC 393), Lb *delbrueckii* subsp. *Bulgaricus* (ATCC 11842), *Lactocaseibacillus paracasei* DSM 5622), *Lactiplantibacillus plantarum* (ATCC 8014), *Lactocaseibacillus rhamnosus* (ATCC 53103), Ligilactobacillus *salivarius* (ATCC 11741), *Lactococcus lactis* (ATCC 19435), *Lactobacillus reuteri* (LMG 9213), *Lactobacillus helveticus* (ATCC 15807), and combinations thereof.

5. The method of claim 1 wherein, said one or more target nucleotide sequence is a nucleotide sequence of from about 20 to 5000 base pairs in length.

6. The method of claim 1 wherein, the step of saving (step B) comprises saving the target nucleotide sequence or sequences selected to serve as a tag and the identity of the item to be tagged in a local or cloud-based database saved in non-transitory computer memory and the step of comparing (step E4) is performed using a basic local alignment search tools (BLAST) algorithm running on a computer or other microprocessor.

7. The method of claim 6 wherein said database is stored on a blockchain.

8. The method of claim 1, wherein, the step of killing (step B) comprises incubation of said food compatible microorganism at temperature of from about 60° C. to about 138° C. for from about 0.01 to about 30 minutes.

9. The method of claim 1, wherein, the step of killing (step B) comprises irradiation of said food compatible microorganism with gamma radiation.

10. The method of claim 1, wherein, the step of killing (step B) comprises irradiation of said food compatible microorganism with x-rays.

11. The method of claim 1, wherein, the cell wall of food compatible microorganism is substantially intact after the step of killing (step B).

12. The method of claim 1 wherein the step of adding (step D) comprises adding two or more different tags to the item.

13. The method of claim 1 wherein, the step of sequencing the amplified target nucleotide sequence (step E.3) is performed using Sanger sequencing or targeted next generation sequencing (tNGS) techniques.

14. The method of claim 1 wherein, the step of comparing (step E.4) is performed using BLAST or a similar algorithm.

15. The method of claim 1 wherein, said product is a food product, agricultural product, personal care, cosmetics, or pharmaceutical product.

16. The method of claim 1 further comprising irradiating said food compatible microorganism to induce mutations in said genomic DNA.

17. The method of claim 1 wherein the step of sequencing (step E.3) or the step of comparing each amplified target nucleotide sequence generated in step E.3 to the nucleotide sequence saved for the target nucleotide sequence in step B and confirming that they match (step E.4) is performed using a microarray.

18. A method for confirming the identity of an item or product by means of a bacterial tag comprising:

A adding one or more tags to a product, each of said one or more tags comprising dead bacteria cells having at least one nucleotide sequence comprising a target sequence not otherwise present in said product;

B recording the identity of the product and the target sequence for later reference; and C confirming the identity of the tagged product by:

C.1 extracting the nucleotide sequence from said product; and adding primers for said target sequence;

C.2 amplifying said target sequence using polymerase chain reaction (PCR) techniques;

C.3 sequencing the amplified target sequence; and

C.4 comparing that sequence to the target nucleotide sequence recorded for the product in step B to confirm the identity of the product.

19. The method of claim 18 wherein, the step of adding (step A) comprises:

A.1 obtaining a plurality of food-compatible bacteria cells for use as a tag, said food-compatible bacteria cells comprising a target nucleotide sequence not otherwise present in the product;

A.2 killing said bacteria cells while leaving the food-compatible bacteria cell walls and DNA substantially intact; and A.3 placing the dead food-compatible bacteria cells on or in said product, thereby producing a tagged product.

20. The method of claim 18 wherein, the step of recording (step B) comprises saving the identity of the product and the target nucleotide sequence in non-transitory computer memory and the step of comparing (step B) is performed using a computer or microprocessor running a sequence analysis algorithm.

21. The method of claim 18 wherein, the step of recording (step B) comprises saving the identity of the product and the target nucleotide sequence to a database stored on a block-chain.

22. The method of claim 18 wherein, the plurality of bacteria cells comprise bacteria selected from the group consisting of Firmicutes (*lactobacillus*), actinobacteria (bifidobacteria), and combinations thereof.

23. The method of claim 19 wherein, the step of killing (step A.2) is performed by at least one of heat treatment, x-ray treatment, and sonication.

24. The method of claim 18 wherein, the step of sequencing the amplified target sequence (step 3) is performed using Sanger sequencing or targeted next generation sequencing (INGS) techniques.

25. The method of claim 18 wherein two or more different tags are added to a product.

26. The method of claim 18 wherein said step of recording further comprises tracking the origins of different components of a mixture, with each component individually tagged and distinguishable.

27. A method for confirming the identity of an item or product by means of a bacterial tag comprising:

A adding one or more tags to a product, each of said one or more tags comprising dead bacteria cells having at least one nucleotide sequence comprising a target sequence not otherwise present in said product;

B recording the identity of the product and the target sequence in a database for later reference; and C confirming the identity of the tagged product by:

C.1 extracting and then sequencing the DNA found in the tagged product using NGS techniques; and C.2 comparing the DNA sequences generated in step C.1 to the target nucleotide sequence recorded in step B for the product to confirm the identity of the product.

* * * * *

SEQUENCE LISTING

```
Sequence total quantity: 31
SEQ ID NO: 1              moltype = DNA  length = 17
FEATURE                   Location/Qualifiers
misc_feature              1..17
                          note = Primer sequence (BflactF) for use with
                          Bifidobacterium animalis subsp. lactis
primer_bind               1..17
source                    1..17
                          mol_type = other DNA
                          organism = synthetic construct
SEQUENCE: 1
ccctttccac gggtccc                                                      17

SEQ ID NO: 2              moltype = DNA  length = 20
FEATURE                   Location/Qualifiers
misc_feature              1..20
                          note = Primer sequence (BflactR) for use with
                          Bifidobacterium animalis subsp. lactis
source                    1..20
                          mol_type = other DNA
                          organism = synthetic construct
```

```
SEQUENCE: 2
aagggaaacc gtgtctccac                                                      20

SEQ ID NO: 3                   moltype = DNA  length = 21
FEATURE                        Location/Qualifiers
misc_feature                   1..21
                               note = Primer sequence (BiBIF-1) for use with
                               Bifidobacterium bifidum bacteria
source                         1..21
                               mol_type = other DNA
                               organism = synthetic construct
SEQUENCE: 3
ccacatgatc gcatgtgatt g                                                    21

SEQ ID NO: 4                   moltype = DNA  length = 19
FEATURE                        Location/Qualifiers
misc_feature                   1..19
                               note = Primer sequence (BiBIF-2) for use with
                               Bifidobacterium bifidum
source                         1..19
                               mol_type = other DNA
                               organism = synthetic construct
SEQUENCE: 4
ccgaaggctt gctcccaaa                                                       19

SEQ ID NO: 5                   moltype = DNA  length = 19
FEATURE                        Location/Qualifiers
misc_feature                   1..19
                               note = Primer sequence (F) for use with Bifidobacterium
                               longum bacteria
source                         1..19
                               mol_type = other DNA
                               organism = synthetic construct
SEQUENCE: 5
cagttgatcg catggtctt                                                       19

SEQ ID NO: 6                   moltype = DNA  length = 16
FEATURE                        Location/Qualifiers
misc_feature                   1..16
                               note = Primer sequence (R) for use with Bifidobacterium
                               longum bacteria
source                         1..16
                               mol_type = other DNA
                               organism = synthetic construct
SEQUENCE: 6
tacccgtcga agccac                                                          16

SEQ ID NO: 7                   moltype = DNA  length = 20
FEATURE                        Location/Qualifiers
misc_feature                   1..20
                               note = Primer sequence (BiINF-1) for use with
                               Bifidobacterium longum subsp. infantis
source                         1..20
                               mol_type = other DNA
                               organism = synthetic construct
SEQUENCE: 7
ttccagttga tcgcatggtc                                                      20

SEQ ID NO: 8                   moltype = DNA  length = 20
FEATURE                        Location/Qualifiers
misc_feature                   1..20
                               note = Primer sequence (BiINF-2) for use with
                               Bifidobacterium longum subsp. infantis bacterial
source                         1..20
                               mol_type = other DNA
                               organism = synthetic construct
SEQUENCE: 8
ggaaacccca tctctgggat                                                      20

SEQ ID NO: 9                   moltype = DNA  length = 17
FEATURE                        Location/Qualifiers
misc_feature                   1..17
                               note = Primer sequence (ddl F1) for use with Enterococcus
                               faecium
source                         1..17
                               mol_type = other DNA
                               organism = synthetic construct
SEQUENCE: 9
gcaaggcttc ttagaga                                                         17
```

```
SEQ ID NO: 10            moltype = DNA   length = 19
FEATURE                  Location/Qualifiers
misc_feature             1..19
                         note = Primer sequence (ddl F2) for Enterococcus faecium
source                   1..19
                         mol_type = other DNA
                         organism = synthetic construct
SEQUENCE: 10
catcgtgtaa gctaacttc                                                       19

SEQ ID NO: 11            moltype = DNA   length = 20
FEATURE                  Location/Qualifiers
misc_feature             1..20
                         note = Primer sequence (LacI) for use with Lactobacillus
                          acidophilus
source                   1..20
                         mol_type = other DNA
                         organism = synthetic construct
SEQUENCE: 11
agctgaacca acagattcac                                                      20

SEQ ID NO: 12            moltype = DNA   length = 20
FEATURE                  Location/Qualifiers
misc_feature             1..20
                         note = Primer sequence (LacII) for use with Lactobacillus
                          acidophilus
source                   1..20
                         mol_type = other DNA
                         organism = synthetic construct
SEQUENCE: 12
actaccaggg tatctaatcc                                                      20

SEQ ID NO: 13            moltype = DNA   length = 20
FEATURE                  Location/Qualifiers
misc_feature             1..20
                         note = Primer sequence (Cas1) for use with
                          Lactocaseibacillus casei
source                   1..20
                         mol_type = other DNA
                         organism = synthetic construct
SEQUENCE: 13
tgcactgaga ttcgacttaa                                                      20

SEQ ID NO: 14            moltype = DNA   length = 24
FEATURE                  Location/Qualifiers
misc_feature             1..24
                         note = Primer sequence (Y2) for use with Lactocaseibacillus
                          casei
source                   1..24
                         mol_type = other DNA
                         organism = synthetic construct
SEQUENCE: 14
cccactgctg cctcccgtag gagt                                                 24

SEQ ID NO: 15            moltype = DNA   length = 26
FEATURE                  Location/Qualifiers
misc_feature             1..26
                         note = Primer Sequence (LB1) for use with Lb. delbrueckii
                          subsp. bulgaricus
source                   1..26
                         mol_type = other DNA
                         organism = synthetic construct
SEQUENCE: 15
aaaaatgaag ttgtttaaag taggta                                               26

SEQ ID NO: 16            moltype = DNA   length = 19
FEATURE                  Location/Qualifiers
misc_feature             1..19
                         note = Primer Sequence (LLB1) for use with Lb. delbrueckii
                          subsp. bulgaricus
source                   1..19
                         mol_type = other DNA
                         organism = synthetic construct
SEQUENCE: 16
aagtctgtcc tctggctgg                                                       19

SEQ ID NO: 17            moltype = DNA   length = 18
FEATURE                  Location/Qualifiers
```

```
misc_feature           1..18
                       note = Primer sequence (Para1) for use with
                       Lactocaseibacillus paracasei
source                 1..18
                       mol_type = other DNA
                       organism = synthetic construct
SEQUENCE: 17
caccgagatt caacatgg                                                         18

SEQ ID NO: 18          moltype = DNA   length = 24
FEATURE                Location/Qualifiers
misc_feature           1..24
                       note = Primer sequence (Y2) for use with Lactocaseibacillus
                       paracasei
source                 1..24
                       mol_type = other DNA
                       organism = synthetic construct
SEQUENCE: 18
cccactgctg cctcccgtag gagt                                                  24

SEQ ID NO: 19          moltype = DNA   length = 21
FEATURE                Location/Qualifiers
misc_feature           1..21
                       note = Primer sequence (Plant 1) for use with
                       Lactiplantibacillus plantarum
source                 1..21
                       mol_type = other DNA
                       organism = synthetic construct
SEQUENCE: 19
atcatggattt acatttgagt g                                                    21

SEQ ID NO: 20          moltype = DNA   length = 21
FEATURE                Location/Qualifiers
misc_feature           1..21
                       note = Primer sequence (LOWLAC) for use with
                       Lactiplantibacillus plantarum
source                 1..21
                       mol_type = other DNA
                       organism = synthetic construct
SEQUENCE: 20
cgacgaccat gaaccacctg t                                                     21

SEQ ID NO: 21          moltype = DNA   length = 21
FEATURE                Location/Qualifiers
misc_feature           1..21
                       note = Primer sequence (Lfpr) for use with
                       Limosilactobacillus reuteri
source                 1..21
                       mol_type = other DNA
                       organism = synthetic construct
SEQUENCE: 21
gccgcctaag gtgggacaga t                                                     21

SEQ ID NO: 22          moltype = DNA   length = 20
FEATURE                Location/Qualifiers
misc_feature           1..20
                       note = Primer sequence (Reu) for use with
                       Limosilactobacillus reuteri
source                 1..20
                       mol_type = other DNA
                       organism = synthetic construct
SEQUENCE: 22
aacactcaag gattgtctga                                                       20

SEQ ID NO: 23          moltype = DNA   length = 19
FEATURE                Location/Qualifiers
misc_feature           1..19
                       note = Primer sequence (Prl) for use with
                       Lactocaseibacillus rhamnosus
source                 1..19
                       mol_type = other DNA
                       organism = synthetic construct
SEQUENCE: 23
cagactgaaa gtctgacgg                                                        19

SEQ ID NO: 24          moltype = DNA   length = 21
FEATURE                Location/Qualifiers
misc_feature           1..21
                       note = Primer sequence (RhaII) for use with
```

-continued

```
                          Lactocaseibacillus rhamnosus
source                    1..21
                          mol_type = other DNA
                          organism = synthetic construct
SEQUENCE: 24
gcgatgcgaa tttctattat t                                          21

SEQ ID NO: 25             moltype = DNA   length = 17
FEATURE                   Location/Qualifiers
misc_feature              1..17
                          note = Primer sequence (Sal1) for use with
                          Ligilactobacillus salivarius
source                    1..17
                          mol_type = other DNA
                          organism = synthetic construct
SEQUENCE: 25
attcactcgt aagaagt                                               17

SEQ ID NO: 26             moltype = DNA   length = 21
FEATURE                   Location/Qualifiers
misc_feature              1..21
                          note = Primer sequence (LOWLAC) for use with
                          Ligilactobacillus salivarius
source                    1..21
                          mol_type = other DNA
                          organism = synthetic construct
SEQUENCE: 26
cgacgaccat gaaccacctg t                                          21

SEQ ID NO: 27             moltype = DNA   length = 21
FEATURE                   Location/Qualifiers
misc_feature              1..21
                          note = Primer sequence (27f) for use with Lactococcus lactis
source                    1..21
                          mol_type = other DNA
                          organism = synthetic construct
SEQUENCE: 27
cgacgaccat gaaccacctg t                                          21

SEQ ID NO: 28             moltype = DNA   length = 20
FEATURE                   Location/Qualifiers
misc_feature              1..20
                          note = Primer sequence (Lla) for use with Lactococcus lactis
source                    1..20
                          mol_type = other DNA
                          organism = synthetic construct
SEQUENCE: 28
cagtcggtac aagtaccaac                                            20

SEQ ID NO: 29             moltype = DNA   length = 20
FEATURE                   Location/Qualifiers
misc_feature              1..20
                          note = Primer sequence (ThI) for use with Streptococcus
                          salivarius subsp. thermophilus
source                    1..20
                          mol_type = other DNA
                          organism = synthetic construct
SEQUENCE: 29
acggaatgta cttgagtttc                                            20

SEQ ID NO: 30             moltype = DNA   length = 19
FEATURE                   Location/Qualifiers
misc_feature              1..19
                          note = Primer sequence (ThII) for use with Streptococcus
                          salivarius subsp. thermophilus
source                    1..19
                          mol_type = other DNA
                          organism = synthetic construct
SEQUENCE: 30
tttggccttt cgacctaac                                             19

SEQ ID NO: 31             moltype = DNA   length = 270
FEATURE                   Location/Qualifiers
source                    1..270
                          mol_type = genomic DNA
                          organism = Lactocaseibacillus paracasei
SEQUENCE: 31
acgcggcgtt gctccatcag acttgcgtcc attgtggaag attccctact gctgcctccc   60
gtaggagttt gggccgtgtc tcagtcccaa tgtggccgat caacctctca gttcggctac  120
```

-continued

```
gtatcatcgc cttggtgagc cattacctca ccaactagct aatacgccgc gggtccatcc   180
aaaagcgata gcttacgcca tctttcagcc aagaaccatg cggttcttgg atctatgcgg   240
tattagcatc tgtttccaaa tgttatcccc                                     270
```